United States Patent
Caille et al.

(10) Patent No.: US 11,753,386 B2
(45) Date of Patent: Sep. 12, 2023

(54) PROCESSES FOR PREPARING A MDM2 INHIBITOR

(71) Applicant: Amgen, Inc., Thousand Oaks, CA (US)

(72) Inventors: Sebastien Caille, Thousand Oaks, CA (US); Michael Corbett, Thousand Oaks, CA (US); Austin Smith, Thousand Oaks, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 17/272,031

(22) PCT Filed: Aug. 30, 2019

(86) PCT No.: PCT/US2019/049087
§ 371 (c)(1),
(2) Date: Feb. 26, 2021

(87) PCT Pub. No.: WO2020/047424
PCT Pub. Date: Mar. 5, 2020

(65) Prior Publication Data
US 2021/0347743 A1    Nov. 11, 2021

Related U.S. Application Data

(60) Provisional application No. 62/725,574, filed on Aug. 31, 2018.

(51) Int. Cl.
*C07D 263/14* (2006.01)
*C07D 211/76* (2006.01)

(52) U.S. Cl.
CPC .......... *C07D 263/14* (2013.01); *C07D 211/76* (2013.01); *C07B 2200/13* (2013.01)

(58) Field of Classification Search
None
See application file for complete search history.

(56) References Cited

U.S. PATENT DOCUMENTS

| 2014/0011796 A1 | 1/2014 | Bartberger et al. |
| 2017/0144971 A1 | 5/2017 | Bartberger et al. |
| 2018/0092898 A1 | 4/2018 | Bio et al. |

OTHER PUBLICATIONS

International Preliminary Report on Patentability dated Mar. 11, 2021 for International Patent Application No. PCT/US2019/049087, 6 pages.
Corbett et al. A Bench-Stable Vilsrneier Reagent for in situ Alcohol Activation: Synthetic Application in the Synthesis of 2-Amino-2-Thiazolines; Synlett 2017, vol. 28, 2845-2850.
Pubchem 117752007 deposited Feb. 23, 2016.
International Search Report and Written Opinion dated Jan. 6, 2020 for International Patent Application No. PCT/US2019/049087, 9 pages.
Wuts, P. G. M. et al., The Synthesis of Oxazolines Using the Vilsmeier Reagent. J. Org. Chem., Nov. 28, 2000, vol. 65, No. 26, pp. 9223-9225.
Cochran, B. M. et al., Development of a Commercial Process to Prepare AMG 232 Using A Green Ozonolysis-Pinnick Tandem Transformation. J. Org. Chem., Dec. 17, 2018, vol. 84, No. 8, pp. 4763-4779.
Search Report dated Jun. 6, 2022 for Singapore Patent Application No. 11202101886V, 5 pages.

*Primary Examiner* — Samantha L Shterengarts
(74) *Attorney, Agent, or Firm* — Morgan, Lewis & Bockius LLP

(57) ABSTRACT

The present invention provides commercial processes for preparing 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid as well as intermediates thereof.

6 Claims, 19 Drawing Sheets

PROCESSES FOR PREPARING A MDM2 INHIBITOR

FIELD OF THE INVENTION

The present invention provides processes for preparing 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid ("Compound A") and intermediates thereof.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which infrequently have a cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in $p53^{WT}$ tumors. In support of this concept, some $p53^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are $p53^{WT}$, and studies with small molecule MDM2 inhibitors have yielded promising reductions in tumor growth both in vitro and in vivo. Further, in patients with p53-inactivated tumors, stabilization of wildtype p53 in normal tissues by MDM2 inhibition might allow selective protection of normal tissues from mitotic poisons.

The present invention relates to a compound capable of inhibiting the interaction between p53 and MDM2 and activating p53 downstream effector genes. As such, the compound of the present invention would be useful in the treatment of cancers, bacterial infections, viral infections, ulcers and inflammation. In particular, the compound of the present invention is useful to treat solid tumors such as: breast, colon, lung and prostate tumors; and liquid tumors such as lymphomas and leukemias. As used herein, MDM2 refers to a human MDM2 protein and p53 refers to a human p53 protein. Human MDM2 can also be referred to as HDM2 or hMDM2.

The compound, 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (also referred to herein as Compound A) is a MDM2 inhibitor and has the following chemical structure. Compound A is disclosed in published PCT Application No.

Compound A

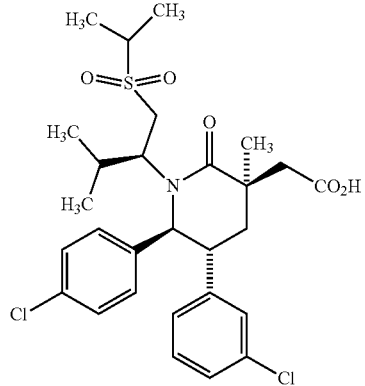

WO 2011/153509 (Example No. 362) and is being investigated in human clinical trials for the treatment of various cancers. The present invention provides improved processes for preparing Compound A as well as intermediate compounds thereof.

SUMMARY OF THE INVENTION

In one embodiment, the present invention provides a process of preparing the following compound (DHO)

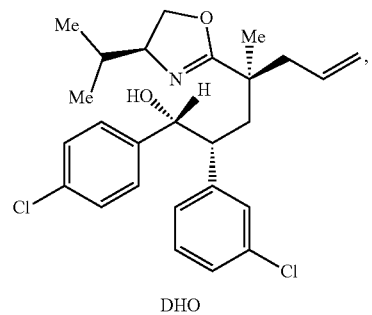 [SMILES: C=CC[C@@](C)(C[C@H](c1cccc(Cl)c1)[C@@H](O)c1ccc(Cl)cc1)C1=N[C@@H](C(C)C)CO1 ; "DHO"]

DHO the process comprising: reacting compound (ABA)

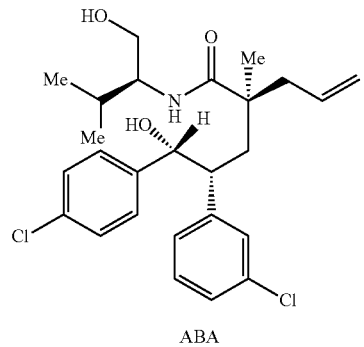 [SMILES: C=CC[C@@](C)(C[C@H](c1cccc(Cl)c1)[C@@H](O)c1ccc(Cl)cc1)C(=O)N[C@H](CO)C(C)C]

ABA with methoxymethylene-N,N-dimethyliminium methyl sulfate. In an embodiment, this reaction is carried out in the presence of a base. In a particular embodiment, the base is an alkali metal salt or an alkaline earth metal salt, such as, for example, KOAc, NaOAc, LiOAc, $CaCO_3$ and $K_2CO_3$. In an embodiment, the reaction is carried out in a solvent. In a particular embodiment, the solvent is benzene, toluene, o-xylene, m-xylene, p-xylene, hexane, tetrahydrofuran, ethyl acetate, HMPA, HMPT, DMSO, ethylene glycol, DME, DMF, diethyl ether, acetonitrile, methanol, ethanol, acetone or mixtures thereof.

In one embodiment, the present invention provides a process of preparing compound (SUL)

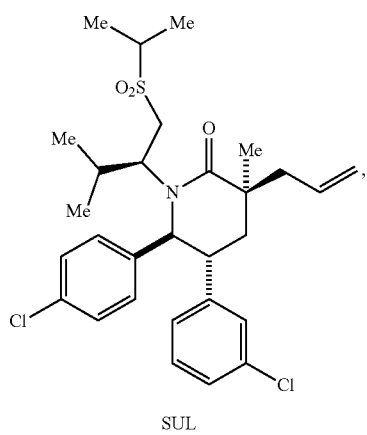

SUL the process comprising: reacting compound

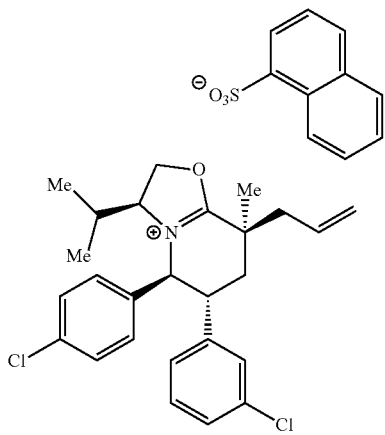

with an isopropylation agent such as, but not limited to, isopropylsulfinate zinc chloride. In an embodiment, the reaction is carried out in presence of an alkaline earth metal salt. In a particular embodiment, the alkaline earth metal salt is a magnesium salt, such as, but not limited to, $MgBr_2$ or $MgCl_2$. In a particular embodiment, the isopropylation agent is generated in situ from isopropyl magnesium chloride. In an embodiment, the reaction is carried out at a temperature between 100° C. and 200° C., such as between 100° C. and 150° C., such as at 120° C. or between 150° C. and 200° C., such as at 180° C.

In one embodiment, the present invention provides a crystalline form of (1R,2R,4S)-2-(3-chlorophenyl)-1-(4-chlorophenyl)-4-((S)-4-isopropyl-4,5-dihydrooxazol-2-yl)-4-methylhept-6-en-1-ol (DHO) characterized by a reflection X-ray powder diffraction pattern comprising peaks at 7.3°±0.2° 2θ, 14.5°±0.2° 2θ, 15.8°±0.2° 2θ, 15.9°±0.2° 2θ, and 23.1°±0.2° 2θ. In an embodiment, the reflection X-ray powder diffraction pattern of the DHO crystalline further comprises peaks at 8.5°±0.2° 2θ, 10.0°±0.2° 2θ, 11.0°±0.2° 2θ, 13.4°±0.2° 2θ, 18.8°±0.2° 2θ, and 22.0°±0.2° 2θ. In an embodiment, the reflection X-ray powder diffraction pattern of the DHO crystalline further comprises one or more peaks at 6.3°±0.2° 2θ, 10.5°±0.2° 2θ, 11.5°±0.2° 2θ, 12.8°±0.2° 2θ, 14.8°±0.2° 2θ, 15.2°±0.2° 2θ, 17.0°±0.2° 2θ, 17.5°±0.2° 2θ, 17.8°±0.2° 2θ, 18.4°±0.2° 2θ, 19.0°±0.2° 2θ, 19.7°±0.2° 2θ, 19.9°±0.2° 2θ, 20.7°±0.2° 2θ, 21.2°±0.2° 2θ, 21.3°±0.2° 2θ, 22.4°±0.2° 2θ, 23.6°±0.2° 2θ, 24.2°±0.2° 2θ, 24.9°±0.2° 2θ, 25.7°±0.2° 2θ, 26.3°±0.2° 2θ, 27.0°±0.2° 2θ, 28.3°±0.2° 2θ, 28.7°±0.2° 2θ, 29.3°±0.2° 2θ, 29.7°±0.2° 2θ, 30.8°±0.2° 2θ, 31.4°±0.2° 2θ, 31.8°±0.2° 2θ, 33.0°±0.2° 2θ, 34.2°±0.2° 2θ, 35.8°±0.2° 2θ, 37.0°±0.2° 2θ, and 37.5°±0.2° 2θ. In an embodiment, the crystalline form of DHO is a crystalline anhydrate. In an embodiment, the reflection x-ray powder diffraction of the crystalline DHO is carried out using Cu—Kα radiation.

BRIEF DESCRIPTION OF THE DRAWINGS

The following figures represent specific embodiments of the invention as described and are not intended to otherwise limit the invention.

DETAILED DESCRIPTION OF THE INVENTION

Figure 1:
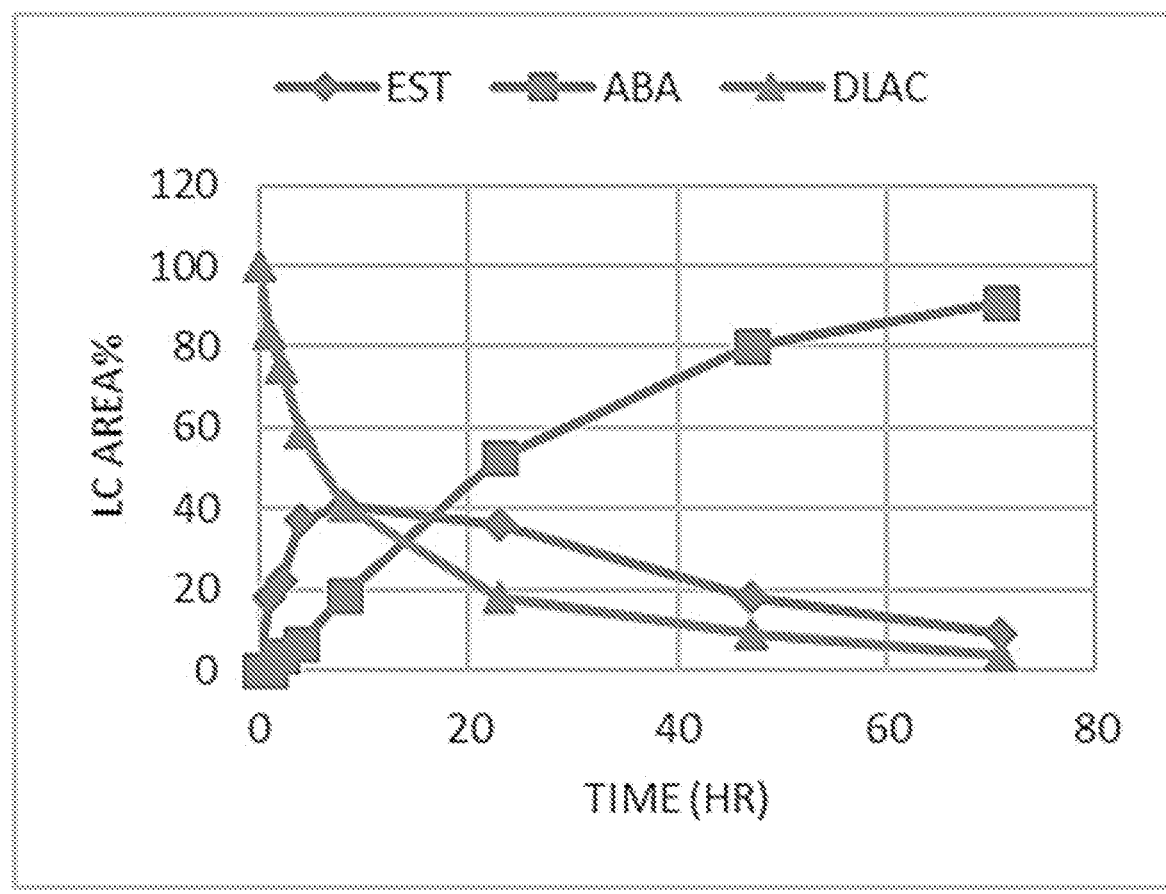
FIG. 1 illustrates the conversion rate of (3S,5R,6R)-3-Allyl-5-(3-chlorophenyl)-6-(4-chlorophenyl)-3-methyltetrahydro-2H-pyran-2-one (DLAC) to (S)-2-((2R,3R)-2-(3-chlorophenyl)-3-(4-chlorophenyl)-3-hydroxypropyl)-N—((S)-1-hydroxy-3-methylbutan-2-yl)-2-methylpent-4-enamide (ABA) over time at 60° C.

The present invention provides processes for preparing 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid ("Compound A") as well as intermediates thereof and processes for preparing these intermediates.

In one aspect, the present invention provides a process for the manufacture of Compound A in high purity.

In another aspect, the present invention employs a bench-stable Vilsmeier reagent, methoxymethylene-N,N-dimethyliminium methyl sulfate (Corbett, M. T.; Caille, S., *Synlett* 2007, 28, 2845), to achieve the selective in situ activation of a primary alcohol intermediate in the preparation of Compound A.

In another aspect, the present disclosure employs a bench-stable crystalline isopropylation agent, isopropyl calcium sulfinate, to achieve the high-yielding preparation of a sulfone intermediate in the preparation of Compound A.

In another aspect, the present disclosure employs a safe ozonolysis reaction conducted in an aqueous solvent mixture in either a batch or continuous manufacturing mode in the process of preparing Compound A.

In another aspect, the present invention provides a crystalline form of (1R,2R,4S)-2-(3-chlorophenyl)-1-(4-chlorophenyl)-4-((S)-4-isopropyl-4,5-dihydrooxazol-2-yl)-4-methylhept-6-en-1-ol (DHO) characterized by a reflection X-ray powder diffraction pattern comprising peaks at 7.3°±0.2° 2θ, 14.5°±0.2° 2θ, 15.8°±0.2° 2θ, 15.9°±0.2° 2θ, and 23.1°±0.2° 2θ. In an embodiment, the reflection X-ray powder diffraction pattern of the DHO crystalline further comprises peaks at 8.5°±0.2° 2θ, 10.0°±0.2° 2θ, 11.0°±0.2° 2θ, 13.4°±0.2° 2θ, 18.8°±0.2° 2θ, and 22.0°±0.2° 2θ. In an embodiment, the reflection X-ray powder diffraction pattern of the DHO crystalline further comprises one or more peaks at 6.3°±0.2° 2θ, 10.5°±0.2° 2θ, 11.5°±0.2° 2θ, 12.8°±0.2° 2θ, 14.8°±0.2° 2θ, 15.2°±0.2° 2θ, 17.0°±0.2° 2θ, 17.5°±0.2° 2θ, 17.8°±0.2° 2θ, 18.4°±0.2° 2θ, 19.0°±0.2° 2θ, 19.7°±0.2° 2θ, 19.9°±0.2° 2θ, 20.7°±0.2° 2θ, 21.2°±0.2° 2θ, 21.3°±0.2° 2θ, 22.4°±0.2° 2θ, 23.6°±0.2° 2θ, 24.2°±0.2° 2θ, 24.9°±0.2° 2θ, 25.7°±0.2° 2θ, 26.3°±0.2° 2θ, 27.0°±0.2° 2θ, 28.3°±0.2° 2θ, 28.7°±0.2° 2θ, 29.3°±0.2° 2θ, 29.7°±0.2° 2θ, 30.8°±0.2° 2θ, 31.4°±0.2° 2θ, 31.8°±0.2° 2θ, 33.0°±0.2° 2θ, 34.2°±0.2° 2θ, 35.8°±0.2° 2θ, 37.0°±0.2° 2θ, and 37.5°±0.2° 2θ. In an embodiment, the crystalline form of DHO is a crystalline anhydrate. In an embodiment, the reflection x-ray powder diffraction of the crystalline DHO is carried out using Cu—Kα radiation.

In another aspect, the present disclosure provides control of the purity of Compound A by crystallization of a 1,4-diazabicyclo[2.2.2]octane (DABCO) salt thereof, which can be effectively purified.

In one embodiment, the present invention provides a process suitable for scale-up of preparing Compound A (99.9 LC area %) in 49.8% overall yield from the starting material DLAC.

The term "comprising" is intended to be open ended, including the indicated component but not excluding other elements.

The term "therapeutically effective amount" refers to an amount of a compound or combination of therapeutically active compounds that ameliorates, attenuates or eliminates one or more symptoms of a particular disease or condition, or prevents or delays the onset of one of more symptoms of a particular disease or condition.

The terms "patient" and "subject" may be used interchangeably and refer to animals, such as dogs, cats, cows, horses, sheep and humans. Particular patients are mammals. The term patient includes males and females.

The term "pharmaceutically acceptable" means that the referenced substance, such as a compound of the present invention, or a salt of the compound, or a formulation containing the compound, or a particular excipient, is suitable for administration to a patient.

The terms "treating", "treat" or "treatment" and the like include preventative (e.g., prophylactic) and palliative treatments.

The term "excipient" refers to any pharmaceutically acceptable additive, carrier, diluent, adjuvant, or other ingredient, other than the active pharmaceutical ingredient (API), which is typically included for formulation and/or administration to a patient.

The compound(s) of the present invention can be administered to a patient in a therapeutically effective amount. The compound(s) can be administered alone or as part of a pharmaceutically acceptable composition or formulation. In addition, the compound(s) or compositions can be administered all at once, as for example, by a bolus injection, multiple times, such as by a series of tablets, or delivered substantially uniformly over a period of time, as for example, using transdermal delivery. It is also noted that the dose of the compound(s) can be varied over time.

The compound(s) of the present invention, or the pharmaceutically acceptable salts thereof, may also be administered in combination with one or more additional pharmaceutically active compounds/agents. It is noted that the additional pharmaceutically active compounds/agents may be a traditional small organic chemical molecule or can be a macromolecule such as proteins, antibodies, peptibodies, DNA, RNA or fragments of such macromolecules.

When a patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compounds may be delivered via a tablet, while another may be administered via injection or orally as a syrup. All combinations, delivery methods and administration sequences are contemplated.

The term "cancer" refers to a physiological condition in mammals that is characterized by unregulated cell growth. General classes of cancers include carcinomas, lymphomas, sarcomas, and blastomas.

The compound(s) of the present invention can be used to treat cancer. The methods of treating a cancer comprise administering to a patient in need thereof a therapeutically effective amount of the compound, or a pharmaceutically acceptable salt thereof.

The compound(s) of the present invention can be used to treat tumors. The methods of treating a tumor comprise administering to a patient in need thereof a therapeutically effective amount of the compound, or a pharmaceutically acceptable salt thereof.

The invention also relates to the use of the compound(s) of the present invention in the manufacture of a medicament for the treatment of a condition such as a cancer.

Cancers which may be treated with the compound(s) of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with the compound(s) of the present invention include endometrial cancer, head and neck cancer, glioblastoma, malignant ascites, and hematopoietic cancers.

Particular cancers that can be treated by the compound(s) of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myelogenous leukemia (AML).

In a particular embodiment of the invention that relates to the treatment of cancers, the cancer is identified as p53wildtype ($p53^{WT}$). In another particular embodiment, the cancer is identified as $p53^{WT}$ and a CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is $p53^{WT}$ will be selected for treatment over patients having a cancer that is mutated with respect to p53. In another aspect, a patient having a cancer that is both $p53^{WT}$ and has a mutant CDNK2A protein is selected over a patient that does not have these characteristics. The taking of a cancer cells for analyses is well known to those skilled in the art. The term "$p53^{WT}$" refers to a protein encoded by genomic DNA sequence no. NC_000017 version 9 (7512445 . . . 7531642)(GenBank); a protein encoded by cDNA sequence no. NM_000546 (GenBank); or a protein having the GenBank sequence no. NP_000537.3. The term "CDNK2A mutant" means a CDNK2A protein that is not wildtype. The term "CDKN2A wildtype" refers to a protein encoded by genomic DNA sequence no. 9:21957751-21984490 (Ensembl ID); a protein encoded by cDNA sequence no. NM_000077 (GenBank) or NM_058195 9GenBank) or; or a protein having the GenBank sequence no. NP_000068 or NP_478102.

In another aspect, the present invention relates to the use of the compound(s) of the present invention in combination with one or more pharmaceutical agents that is an inhibitor of a protein in the phosphatidylinositol 3-kinase (PI3K) pathway. Combinations of the compound(s) of the present invention with inhibitors of proteins in the PI3K pathway have shown synergy in cancer cell growth assays, including enhanced apoptosis and cell killing. Examples of proteins in the PI3K pathway include PI3K, mTOR and PKB (also known as Akt). The PI3K protein exists in several isoforms including α, β, δ, or γ. It is contemplated that a PI3K inhibitor that can be used in combination with a compound of the present invention can be selective for one or more isoform. By selective it is meant that the compound(s) inhibit one or more isoforms more than other isoforms. Selectivity is a concept well known to those in the art and can be measured with well-known activity in in vitro or cell-based assays. Preferred selectivity includes greater than 2-fold, preferably 10-fold, or more preferably 100-fold greater selectivity for one or more isoforms over the other isoforms. In one aspect, the PI3K inhibitors that can be used in combination with compound(s) of the present invention is a PI3K α selective inhibitor. In another aspect the compound is a PI3K δ selective inhibitor.

Examples of PI3K inhibitors that can be used in combination with the compound(s) of the present invention include those disclosed in, for example, WO 2010/151791; WO 2010/151737; WO 2010/151735; WO 2010/151740; WO 2008/118455; WO 2008/118454; WO 2008/118468; US 20100331293; US 20100331306; US 20090023761; US 20090030002; US 20090137581; US 20090054405; US 20090163489; US 20100273764; US 20110092504; or WO 2010/108074.

Compounds that inhibit both PI3K and mTOR (dual inhibitors) are known. In still another aspect, the present invention provides the use of dual PI3K and mTOR inhibitors for use in combination with the compound(s) of the present invention.

mTOR is a protein in the PI3K pathway. It is another aspect of the present invention to use an mTOR inhibitor in combination with the compound(s) of the present invention. Suitable mTOR inhibitors that can be used in combination with the compound(s) of the present invention include those disclosed in, for example, WO 2010/132598 and WO 2010/096314.

PKB (Akt) is also a protein in the PI3K pathway. It is another aspect of the present invention to use an mTOR inhibitor in combination with the compound(s) of the present invention. PKB inhibitors that can be used in combination with the compound(s) of the present invention include those disclosed in, for example, U.S. Pat. Nos. 7,354,944; 7,700,636; 7,919,514; 7,514,566; US 20090270445 A1; U.S. Pat. Nos. 7,919,504; 7,897,619; and WO 2010/083246.

The combinations of the present invention may also be used in conjunction with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compound(s) of the present invention and other pharmaceutically active compounds, if desired, can be administered to a patient either orally, rectally, parenterally (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound(s), may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of the compound(s) of the present invention include ointments, powders, sprays and inhalants. The active compound or compounds are admixed under sterile condition with a physiologically acceptable carrier, and any preservatives, buffers, or propellants that may be required. Ophthalmic formulations, eye ointments, powders, and solutions are also contemplated as being within the scope of this invention.

The compound(s) of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compound(s) of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed.

Examples of pharmaceutically acceptable esters of the compound(s) of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of the compound(s) of the present invention may be prepared according to methods that are well known in the art.

Examples of pharmaceutically acceptable amides of the compound(s) of the present invention include amides derived from ammonia, primary $C_1$-$C_8$ alkyl amines, and secondary $C_1$-$C_8$ dialkyl amines. In the case of secondary amines, the amine may also be in the form of a 5- or 6-membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compound(s) of the present invention may be prepared according to methods well known to those skilled in the art.

The term "prodrug" refers to compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, because the compound(s) of the invention contain a carboxylic acid functional group, a prodrug can comprise an ester formed by the replacement of the hydrogen atom of the carboxylic acid group with a group such as $C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

The compound(s) of the present invention may contain asymmetric or chiral centers, and therefore, exist in different stereoisomeric forms. It is contemplated that all stereoisomeric forms of the compound(s) as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures thereof, are contemplated.

Mixtures of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the resulting diastereomers and then converting (e.g., hydrolyzing) the individual diastereomers to the corresponding pure enantiomers.

The compound(s) of the present invention may exist in unsolvated as well as solvated forms with pharmaceutically acceptable solvents such as water (hydrate), ethanol, and the like. The present invention contemplates and encompasses both the solvated and unsolvated forms as set forth herein.

It is also possible that the compound(s) of the present invention may exist in different tautomeric forms. All tautomers of the compound(s) of the present invention are contemplated. For example, all of the tautomeric forms of the tetrazole moiety are included in this invention. Also, for example, all keto-enol or imine-enamine forms of the compound(s) are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompasses compounds that are synthesized in vitro using laboratory techniques, such as those well known to synthetic chemists; or synthesized using in vivo techniques, such as through metabolism, fermentation, digestion, and the like. It is also contemplated that the compound(s) of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compound(s) of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{18}O$, $^{31}P$, $^{32}P$, $^{35}S$, $^{18}F$, and $^{36}Cl$. In one aspect, the present invention relates to compounds wherein one or more hydrogen atom is replaced with deuterium ($^2H$) atoms.

The compound(s) of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

The compound(s) of the present invention may exist in various solid states including crystalline states and as an amorphous state. The different crystalline states (also called polymorphs) and the amorphous state of the present compound(s) are contemplated as part of this invention as set forth herein.

In synthesizing the compound(s) of the present invention, it may be desirable to employ certain leaving groups. The term "leaving groups" ("LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, published patent applications and other publications recited herein are hereby incorporated by reference.

The specific experimental examples presented in this application illustrate specific embodiments of the present invention. These examples are meant to be representative and are not intended to limit the scope of the claims in any manner.

$^1$H-NMR spectra were typically acquired on a Bruker Avance III 500 spectrometer system (Bruker, Billerica, Mass.) operating at a $^1$H frequency of 500.13 MHz, equipped with a Bruker 5 mm PABBI probe with a z-axis gradient; or on a Bruker Avance II or Avance III 400 spectrometer operating at a $^1$H frequency of 400.23 MHz, equipped with a Bruker 5 mm PABBO probe with a z-axis gradient. Samples were typically dissolved in 500 μL of either DMSO-$d_6$ or $CD_3OD$ for NMR analysis. $^1$H chemical shifts are referenced to the residual solvent signals from DMSO-$d_6$ at δ 2.50 and $CD_3OD$ at δ 3.30.

Significant peaks are tabulated and typically include the number of protons, multiplicity (s, singlet; d, doublet; dd, doublet of doublets; t, triplet; q, quartet; m, multiplet; br s, broad singlet) and coupling constant(s) in Hertz (Hz). Electron Ionization (EI) mass spectra were typically recorded on an Agilent Technologies 6140 Quadrupole LC/MS mass spectrometer (Agilent Technologies, Englewood, Colo.). Mass spectrometry results are reported as the ratio of mass over charge, sometimes followed by the relative abundance of each ion (in parentheses). Starting materials in the Examples below are typically either available from commercial sources such as Sigma-Aldrich, St. Louis, Mo., or via published literature procedures.

X-Ray powder diffraction data (XRPD) were obtained using a Bruker D8 Discover X-ray diffraction system (Bruker, Billerica, Mass.) equipped with a Braun detector and a Cu—Kα radiation source operating in Bragg-Brentano reflection geometry. 2θ values are generally accurate to within an error of ±0.2°. The samples were generally prepared without any special treatment other than the application of slight pressure to get a flat surface. Samples were measured uncovered unless otherwise noted. Operating conditions included a tube voltage of 40 kV and current of 40 mA. A variable divergence slit was used with a 3° window. The step size was 0.019° 2θ with a step time of 35.2 seconds, and the scanning range is: 3-40.4°.

Figure 19:
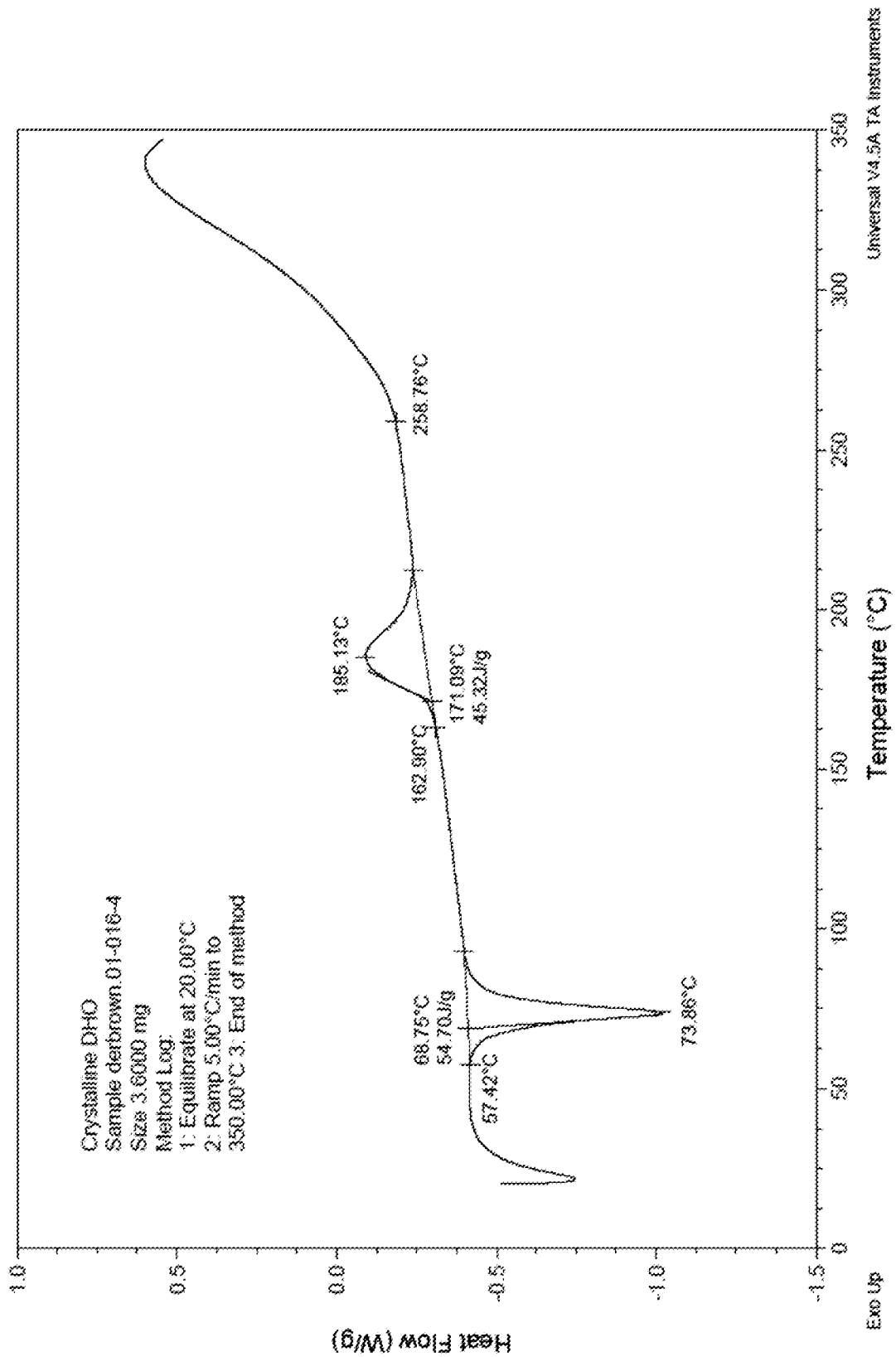
FIG. 19 illustrates a thermogram from differential scanning calorimetry (DSC) analysis of crystalline DHO.

Differential scanning calorimetry (DSC) was carried out with a Perkin Elmer DSC-7 or with a TA Instruments Q2000 instrument. Samples were prepared in a closed gold sample pan at temperature ramp rates of 5° C./minute from 20° C. up to approximately 350° C. The DSC thermogram of crystalline DHO is shown in FIG. 19 with a melting point at 73.86°.

EXAMPLES

Example 1: Method for Preparing Selected Intermediates

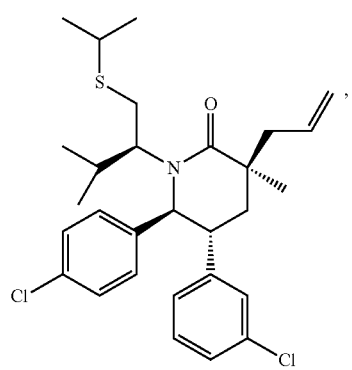

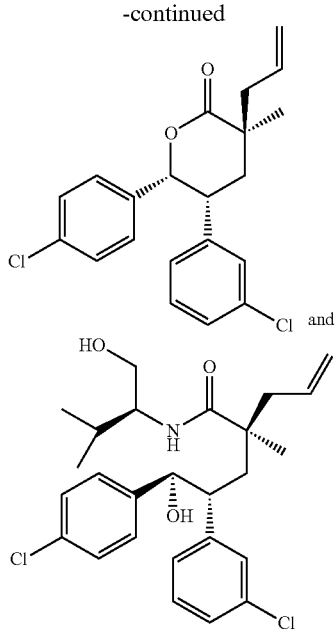

Step A.
2-(3-Chlorophenyl)-1-(4-chlorophenyl)ethanone

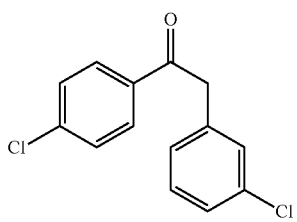 [SMILES: O=C(Cc1cccc(Cl)c1)c1ccc(Cl)cc1]

Sodium bis(trimethylsilyl)amide (1 M in tetrahydrofuran, 117 mL) was slowly added to a −78° C. solution of 2-(3-chlorophenyl) acetic acid (10 g, 58.6 mmol) in tetrahydrofuran (58 mL) over 1 hour. After stirring at −78° C. for 40 minutes, a solution of methyl 4-chlorobenzoate (10 g, 58.6 mmol) in tetrahydrofuran (35 mL) was added over a period of 10 minutes. The reaction was stirred at −78° C. for 3 hours and then allowed to warm to 25° C. After two hours at 25° C., the reaction was quenched with saturated aqueous ammonium chloride solution, and most of the tetrahydrofuran was removed under reduced pressure. The residue was extracted with ethyl acetate (2×100 mL). The combined organic layers were washed with a saturated sodium chloride solution, dried over sodium sulfate, filtered and the filtrate was concentrated. The product was recrystallized from ether/pentane to provide the 2-(3-chlorophenyl)-1-(4-chlorophenyl)ethanone as a white solid.

Alternative Procedure for Preparing 2-(3-Chlorophenyl)-1-(4-chlorophenyl)ethanone To a mixture of chlorobenzene (170 L, 1684 mol), 3-chlorophenylacetic acid (50 Kg, 293 mol), and dimethylformamide (0.7 L, 9 mol) at 0° C. was added thionyl chloride (39.1 Kg, 329 mol) over the course of 30 min. The mixture was warmed to 15° C. and agitated for 6 h. The mixture was cooled to 0° C. and aluminum chloride (43 Kg, 322 mol) was added over the course of 1.5 h. The mixture was warmed to 20° C. and agitated for 15 h. Water (200 L) and ethanol (200 L) were added to the mixture and the biphasic mixture was agitated for 2 h. The phases were separated and the organic phase was washed twice with aqueous ethylenediaminetetraacetic acid tetrasodium salt (3 wt %, 200 L), and once with water (200 L). Heptane (1600 L) was added to the organic phase over the course of 15 minutes. The suspension was agitated for 30 minutes, cooled to −5° C., and filtered. The filtered material was dried at 40° C. for 20 h. 2-(3-Chlorophenyl)-1-(4-chlorophenyl)ethanone was isolated in 83.6% yield (67.4 Kg). $^1$H NMR (500 MHz, DMSO-$d_6$, δ ppm): 8.05 (m, 2H), 7.62 (m, 2H), 7.33 (m, 3H), 7.21 (br d, J=7.3 Hz, 1H), 4.45 (s, 2H). MS (ESI)=265.1 [M+H]$^+$.

Step B: Methyl 4-(3-chlorophenyl)-5-(4-chlorophenyl)-2-methyl-5-oxopentanoate

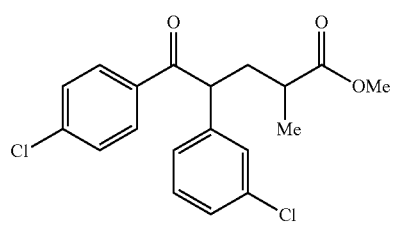 [SMILES: COC(=O)C(C)CC(C(=O)c1ccc(Cl)cc1)c1cccc(Cl)c1]

Methyl methacrylate (12.65 mL, 119 mmol) was added to a solution of 2-(3-chlorophenyl)-1-(4-chlorophenyl)ethanone (30 g, 113 mmol) (from Step A) in tetrahydrofuran (283 mL). Potassium tert-butoxide (1.27 g, 11.3 mmol) was then added and the reaction was stirred at room temperature for 2 days. The solvent was then removed under vacuum and replaced with 300 mL of ethyl acetate. The organic phase was washed with brine (50 mL), water (3×50 mL), and brine (50 mL). The organic phase was dried over magnesium sulfate, filtered and concentrated under vacuum to afford methyl 4-(3-chlorophenyl)-5-(4-chlorophenyl)-2-methyl-5-oxopentanoate as an approximately 1:1 mixture of diastereomers. $^1$H NMR (400 MHz, CDCl$_3$, δ ppm): 7.87 (m, 2H), 7.38 (m, 2H), 7.27-7.14 (series of m, 4H), 4.61 (m, 1H), 3.69 (s, 1.5H), 3.60 (s, 1.5H), 2.45 (m, 1H), 2.34 (m, 1H), 2.10 (ddd, J=13.9, 9.4, 5.5 Hz, 0.5H), 1.96 (ddd, J=13.7, 9.0, 4.3 Hz, 0.5H), 1.22 (d, J=7.0 Hz, 1.5H), 1.16 (d, J=7.0, 1.5H). MS (ESI)=387.0 [M+23]$^+$.

Step C: (3S,5R,6R)-5-(3-Chlorophenyl)-6-(4-chlorophenyl)-3-methyltetrahydro-2H-pyran-2-one and (3R,5R,6R)-5-(3-chlorophenyl)-6-(4-chlorophenyl)-3-methyltetrahydro-2H-pyran-2-one

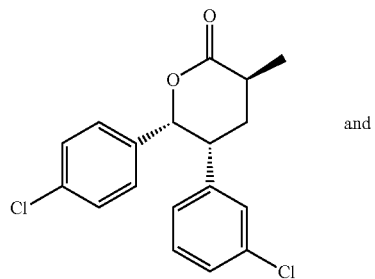

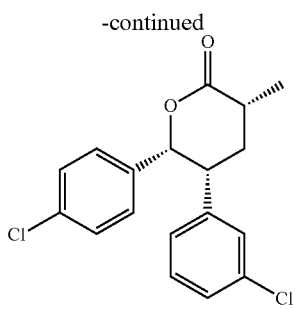

Methyl 4-(3-chlorophenyl)-5-(4-chlorophenyl)-2-methyl-5-oxopentanoate (40 g, 104.0 mmol) (from Step B) was dissolved in 200 mL of anhydrous toluene and concentrated under vacuum. The residue was placed under high vacuum for 2 hours before use. The compound was split into 2×20 g batches and processed as follows: methyl 4-(3-chlorophenyl)-5-(4-chlorophenyl)-2-methyl-5-oxopentanoate (20 g, 52.0 mmol) in anhydrous 2-propanol (104 mL) was treated with potassium tert-butoxide (2.33 g, 20.8 mmol) in a 250 mL glass hydrogenation vessel. $RuCl_2$(S-xylbinap)(S-DAIPEN) (0.191 g, 0.156 mmol, Strem Chemicals, Inc., Newburyport, Mass.) in 3.8 mL of toluene was added. After 1.5 hours, the vessel was pressurized to 50 psi (344.7 kPa) and purged with hydrogen five times and allowed to stir at room temperature. The reaction was recharged with additional hydrogen as needed. After 3 days, the reactions were combined and partitioned between 50% saturated ammonium chloride solution and ethyl acetate. The aqueous layer was extracted with ethyl acetate. The combined organic phases were washed with brine, dried over magnesium sulfate, filtered, and concentrated.

The crude product (predominantly, (4R,5R)-isopropyl 4-(3-chlorophenyl)-5-(4-chlorophenyl)-5-hydroxy-2-methylpentanoate) was dissolved in tetrahydrofuran (450 mL) and methanol (150 mL). Lithium hydroxide (1.4 M, 149 mL, 208 mmol) was added, and the solution was stirred at room temperature for 24 hours. The mixture was concentrated under vacuum and the residue was redissolved in ethyl acetate. Aqueous 1N hydrochloric acid was added with stirring until the aqueous layer had a pH of about 1. The layers were separated and the organic phase was washed with brine, dried over magnesium sulfate, filtered and concentrated. The material was then dissolved in 200 mL of anhydrous toluene and treated with pyridiniump-toluenesulfonate (PPTS, 0.784 g, 3.12 mmol). The reaction was heated to reflux under Dean-Stark conditions until the seco-acid was consumed (about 2 hours). The reaction was cooled to room temperature and washed with saturated sodium bicarbonate (50 mL) and brine (50 mL). The solution was dried over sodium sulfate, filtered and concentrated. The crude material was purified by flash chromatography on silica gel (120 g column; eluting with 100% dichloromethane). The (3S,5R,6R)-5-(3-chlorophenyl)-6-(4-chlorophenyl)-3-methyltetrahydro-2H-pyran-2-one and (3R,5R,6R)-5-(3-chlorophenyl)-6-(4-chlorophenyl)-3-methyltetrahydro-2H-pyran-2-one were obtained as a white solid with an approximate 94:6 enantiomeric ratio and a 7:3 mixture of methyl diastereomers. $^1$H NMR (400 MHz, $CDCl_3$, δ ppm): 7.22-6.98 (series of m, 5H), 6.91 (dt, J=7.4, 1.2 Hz, 0.3H), 6.81 (m, 2H), 6.73 (dt, J=7.6, 1.4 Hz, 0.7H), 5.76 (d, J=4.1 Hz, 0.3H), 5.69 (d, J=4.7 Hz, 0.7H), 3.67 (dt, J=6.6, 4.3 Hz, 0.3H), 3.55 (td, J=7.8, 4.7 Hz, 0.7H), 2.96 (d of quintets, J=13.5, 6.7 Hz, 0.7H), 2.81 (m, 0.3H), 2.56 (dt, J=14.3, 8.0 Hz, 0.7H), 2.32 (dt, J=13.69, 7.0 Hz, 0.3H), 2.06 (ddd, J=13.7, 8.4, 4.1, 0.3H), 1.85 (ddd, J=14.1, 12.5, 7.4, 0.7H), 1.42 (d, J=7.0 Hz, 0.9H), 1.41 (d, J=6.7 Hz, 2.1H). MS (ESI)=357.0 [M+23]$^+$. [α]$_D$ (22° C., c=1.0, $CH_2Cl_2$)=−31.9°; m.p. 98-99° C.

Step D. (3S,5R,6R)-3-Allyl-5-(3-chlorophenyl)-6-(4-chlorophenyl)-3-methyltetrahydro-2H-pyran-2-one

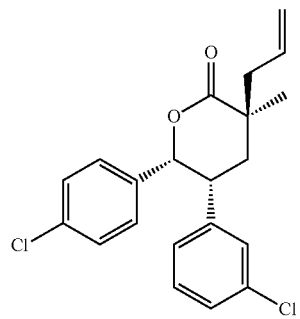 [SMILES: C=CC[C@@]1(C)C[C@H](c2cccc(Cl)c2)[C@H](c2ccc(Cl)cc2)OC1=O]

A solution of (3S,5R,6R)-5-(3-chlorophenyl)-6-(4-chlorophenyl)-3-methyltetrahydro-2H-pyran-2-one and (3R,5S,6S)-5-(3-chlorophenyl)-6-(4-chlorophenyl)-3-methyltetrahydro-2H-pyran-2-one (4.5 g, 13.4 mmol) (from Step C) and allyl bromide (3.48 mL, 40.3 mmol) in tetrahydrofuran (22 mL) at −35° C. (acetonitrile/dry ice bath) was treated with a solution of lithium bis(trimethylsilyl)amide in tetrahydrofuran (1.0 M, 17.45 mL, 17.45 mmol). The reaction was allowed to warm to −5° C. over 1 hour and then was quenched with 50% saturated ammonium chloride. The reaction was diluted with 100 mL of ethyl acetate and the layers were separated. The organic phase was washed with brine, dried over magnesium sulfate, filtered and concentrated under vacuum to afford the title compound as a white solid upon standing under vacuum. Chiral SFC (92% $CO_2$, 8% methanol (20 mM ammonia), 5 mL/min, Phenomenex Lux-2 column (Phenomenex, Torrance, Calif.), 100 bar (10,000 kPa), 40° C., 5 minute method) was used to determine that the compound had an enantiomeric ratio of 96:4. (Major enantiomer: title compound, retention time=2.45 minutes, 96%; minor enantiomer (structure not shown, retention time=2.12 min, 4%). The (3S,5R,6R)-3-allyl-5-(3-chlorophenyl)-6-(4-chlorophenyl)-3-methyltetrahydro-2H-pyran-2-one was recrystallized by addition to heptane (4.7 g slurried in 40 mL) at reflux followed by dropwise addition of 1.5 mL of toluene to solubilize. The solution was cooled to 0° C. The resulting white solid was filtered and rinsed with 20 mL of cold heptane to afford a white powder. Chiral SFC (92% $CO_2$, 8% methanol, Phenomenex Lux-2 column, same method as above) indicated an enantiomeric ratio of 99.2:0.8. (major enantiomer, 2.45 min, 99.2%; minor enantiomer: 2.12 min, 0.8%). $^1$H NMR (400 MHz, $CDCl_3$, δ ppm): 7.24 (ddd, J=8.0, 2.0, 1.2 Hz, 1H), 7.20-7.15 (series of m, 3H), 6.91 (t, J=2.0 Hz, 1H), 6.78 (br d, J=7.6 Hz, 1H), 6.60 (m, 2H), 5.84 (ddt, J=17.6, 10.2, 7.4 Hz, 1H), 5.70 (d, J=5.3 Hz, 1H), 5.21-5.13 (series of m, 2H), 3.82 (dt, J=11.7, 4.5 Hz, 1H), 2.62 (A<u>B</u>X $J_{AB}$=13.7 Hz, $J_{AX}$=7.6 Hz, 1H), 2.53 (AB<u>X</u>, $J_{AB}$=13.9 Hz, $J_{BX}$=7.2 Hz, 1H). 1.99 (dd, J=14.1, 11.9 Hz, 1H), 1.92 (ddd, J=13.9, 3.9, 1.2 Hz, 1H). $^{13}$C NMR ($CDCl_3$, 100 MHz, δ ppm): 175.9, 140.2, 134.5, 134.3, 134.0, 132.2, 129.8, 128.6, 128.0, 127.9, 127.8, 126.4, 119.9, 83.9, 44.5, 42.4, 40.7, 31.8, 26.1. MS (ESI)=375.2 [M+H]$^+$. IR=1730 cm$^{-1}$. [α]$_D$ (24° C., c=1.0, CH$_2$Cl$_2$)=−191°. m.p. 111-114° C.

Alternative Procedure for Preparing (3S,5R,6R)-3-allyl-5-(3-chlorophenyl)-6-(4-chlorophenyl)-3-methyltetrahydro-2H-pyran-2-one

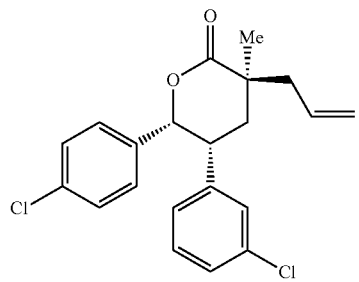 [SMILES: C=CC[C@@]1(C)C[C@H](c2cccc(Cl)c2)[C@H](c2ccc(Cl)cc2)OC1=O]

Step 1: Isopropyl 4-(3-chlorophenyl)-5-(4-chlorophenyl)-2-methyl-5-oxopentanoate

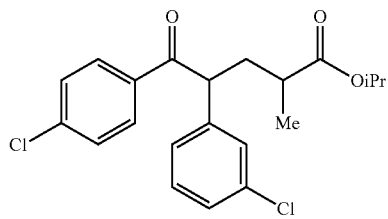 [SMILES: CC(C)OC(=O)C(C)CC(C(=O)c1ccc(Cl)cc1)c1cccc(Cl)c1]

A solution of 2-(3-chlorophenyl)-1-(4-chlorophenyl)ethanone (Step A) (67.4 Kg, 255 mol) in THF (325 L) was dried azeotropically to achieve a water content by Karl Fisher of 0.05 wt %. Methyl methacrylate (25.8 Kg, 257 mol) was added to the solution and the mixture was heated to 45° C. A solution of potassium tert-butoxide (20 wt % in THF, 14.3 Kg, 25 mol) was added over the course of 30 minutes and the mixture was agitated for 6 h. The mixture was then cooled to 10° C. and an aqueous solution of citric acid monohydrate (20 wt %, 35 L) was added in less than 5 minutes. Isopropyl acetate (400 L) and an aqueous sodium chloride solution (20 wt %, 300 L) were added. The mixture was agitated for 15 minutes and the phases were separated. The organic phase was distilled under reduced pressure to generate a distillate volume of 560 L while simultaneously adding isopropanol (350 L) to produce a solution of methyl 4-(3-chlorophenyl)-5-(4-chlorophenyl)-2-methyl-5-oxopentanoate in isopropanol (54 wt %, 140 kg total solution mass). The solution had a water content of 0.01 wt % by Karl Fisher. Additional isopropanol (420 L) and sulfuric acid (53 Kg, 535 mol) were added to the solution. The mixture was warmed to reflux and agitated for 12 h, during which time 200 L of solvent were distilled and 200 L of fresh isopropanol were added to the mixture. The mixture was then cooled to 20° C. and water (180 L) was added over the course of 30 minutes. Isopropyl acetate (270 L) was added and the mixture was agitated for 30 minutes. The phases were separated and the aqueous phase was extracted using isopropyl acetate (100 L). The combined organic phases were washed with water (200 L) four times. The organic phase was distilled under reduced pressure to generate a distillate volume of 500 L while simultaneously adding isopropanol (50 L) to provide a solution of isopropyl 4-(3-chlorophenyl)-5-(4-chlorophenyl)-2-methyl-5-oxopentanoate in isopropanol (60 wt %, 134 kg total solution mass). The solution had a water content of 0.02 wt % by Karl Fisher. The isopropyl 4-(3-chlorophenyl)-5-(4-chlorophenyl)-2-methyl-5-oxopentanoate was obtained in 81% overall yield as a roughly 1:1 mixture of diastereoisomers. $^1$H NMR (400 MHz, CDCl$_3$, δ ppm): 7.70-7.80 (m, 2H), 7.22-7.28 (m, 2H), 7.00-7.18 (series of m, 4H), 4.78-4.96 (m, 1H), 4.42-4.50 (m, 1H), 2.02-2.30 (m, 2H), 1.80-1.95 (m, 1H), 0.99-1.19 (m, 15H).

Step 2. (3S,5R,6R)-3-Allyl-5-(3-chlorophenyl)-6-(4-chlorophenyl)-3-methyltetrahydro-2H-pyran-2-one

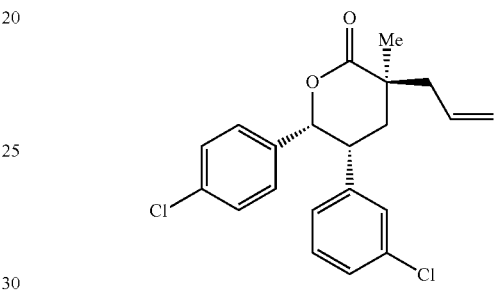

To a degassed solution of isopropyl 4-(3-chlorophenyl)-5-(4-chlorophenyl)-2-methyl-5-oxopentanoate (from Step 1) in isopropanol (60 wt %, 252 kg total solution mass, 151 Kg of isopropyl ester starting material, 385 mol) was added degassed isopropanol (900 L) and potassium tert-butoxide (13 Kg, 116 mol). A separately prepared degassed solution of (S)-RUCY®-XylBINAP (also known as RuCl[(S)-diapena][(S)-xylbinap] (230 g, 0.2 mol, catalyst, Takasago International Corporation, Rockleigh, N.J.) in isopropanol (25 L). The mixture was purged four times with hydrogen at 5 bars (500 kPa) and agitated at 20° C. for 5.5 h. The hydrogen pressurization was discontinued and the mixture was degassed with nitrogen. Tetrahydrofuran (460 L) was added to the mixture. A solution of lithium hydroxide (24 Kg, 576 mol) in water (305 L) was added to the reaction mixture over the course of 40 minutes and the resultant mixture was agitated at 20° C. for 24 h. A solution of concentrated hydrochloric acid (79.3 Kg, 11.4 M, 740 mol) in water (690 L) was added to the mixture over the course of 2 h. Toluene (580 L) was added, the mixture was then agitated for 30 minutes, and the phases were separated. The aqueous phase was extracted using toluene (700 L). The combined organic layers were washed with an aqueous solution of sodium chloride (25 wt %, 700 Kg). The organic phase was distilled at atmospheric pressure and 100° C. to generate a distillate volume of 2700 L while simultaneously adding toluene (800 L). Less than 0.05 wt % isopropanol or water (by Karl Fisher) remained in the mixture after this solvent exchange. Carbonyl diimidazole (59 Kg, 365 mol) was added to the toluene solution over the course of 2 h and the mixture was agitated at 20° C. for two additional hours. The mixture was then cooled to 10° C. and a solution of orthophosphoric acid (72 Kg, 545 mol) in water (400 L) was added over the course of 1 h, while maintaining the temperature of the mixture below 20° C. The mixture was agitated for 30 minutes, the phases were separated and the organic layer was washed with an aqueous solution of sodium chloride (25 wt %, 484 Kg). Toluene (400 L) was distilled at atmospheric pressure and at 110° C. After cooling of the solution to 20° C., tetrahydrofuran (500 L) was added and the water content by Karl Fisher was measured to be 0.03 wt %. The product solution was cooled to −10° C. and a solution allyl bromide (66.8 Kg, 552 mol) in tetrahydrofuran (50 L) was added. A lithium hexamethyldisilazide solution in toluene (255 Kg, 26 wt %, 492 mol) was added over the course of 6 h and the mixture was stirred at −10° C. for 1 h. The mixture was warmed to 0° C. and an aqueous solution of orthophosphoric acid (40 wt %, 400 mol) was added over the course of 3 h. The mixture was warmed to 20° C. Water (200 L) and dichloromethane (400 L) were added. The mixture was agitated for 15 minutes and the phases were separated. The solution was distilled at atmospheric pressure and 100° C. to generate a distillate volume of 1350 L and the residual toluene in the mixture was measured to be 9.8 wt %. The mixture was cooled to 70° C. Diisopropyl ether (85 L), water (26 L), and isopropanol (65 L) were added. The mixture was cooled to 35° C., agitated for 9 h, cooled to 30° C., and filtered. The filtered material was washed three times with heptane (80 L). The solids were dried at 55° C. for 48 hours to provide 90.1 Kg of (3S,5R,6R)-3-allyl-5-(3-chlorophenyl)-6-(4-chlorophenyl)-3-methyltetrahydro-2H-pyran-2-one in 63% overall yield. Chiral HPLC indicated an enantiomeric ratio of 99.95:0.05.

Example 2: Differences Between First-in-Human Process and Commercial Process of Making Compound A A gram-scale synthesis of DLAC has previously been reported. See, Sun et al., *J. Med. Chem.* 2014, 57, 1454. Based on this work, Compound A was prepared by the first-in-human (FIH) synthetic process illustrated in Scheme 1. Intermediate OXOS was used as a regulatory starting material for this process. Ring-opening of DLAC using excess L-valinol (3 equivalents) at elevated temperature afforded amide ABA, which was extracted in dichloromethane. Excess L-valinol was removed using aqueous hydrochloric acid washes and the product solution was carried into the subsequent step without purification. Reduction of the amounts of L-valinol used in this transformation was identified as a development objective going forward in view of the high cost of this raw material. Notably, the preparation of ABA analogues ABA1 or ABA2 from the corresponding DLAC analogues DLAC1 or DLAC2, which bear sidechains containing a group of the same oxidation state as the carboxylic acid of Compound A, was not successful due to the formation of the undesired succinimides SUC1 or SUC2. Considering the similar rates observed for the formation of the desired products ABA1-ABA2 and their transformation to the side-products SUC1-SUC2, it was not possible to isolate the amides ABA1-ABA2 in acceptable yields.

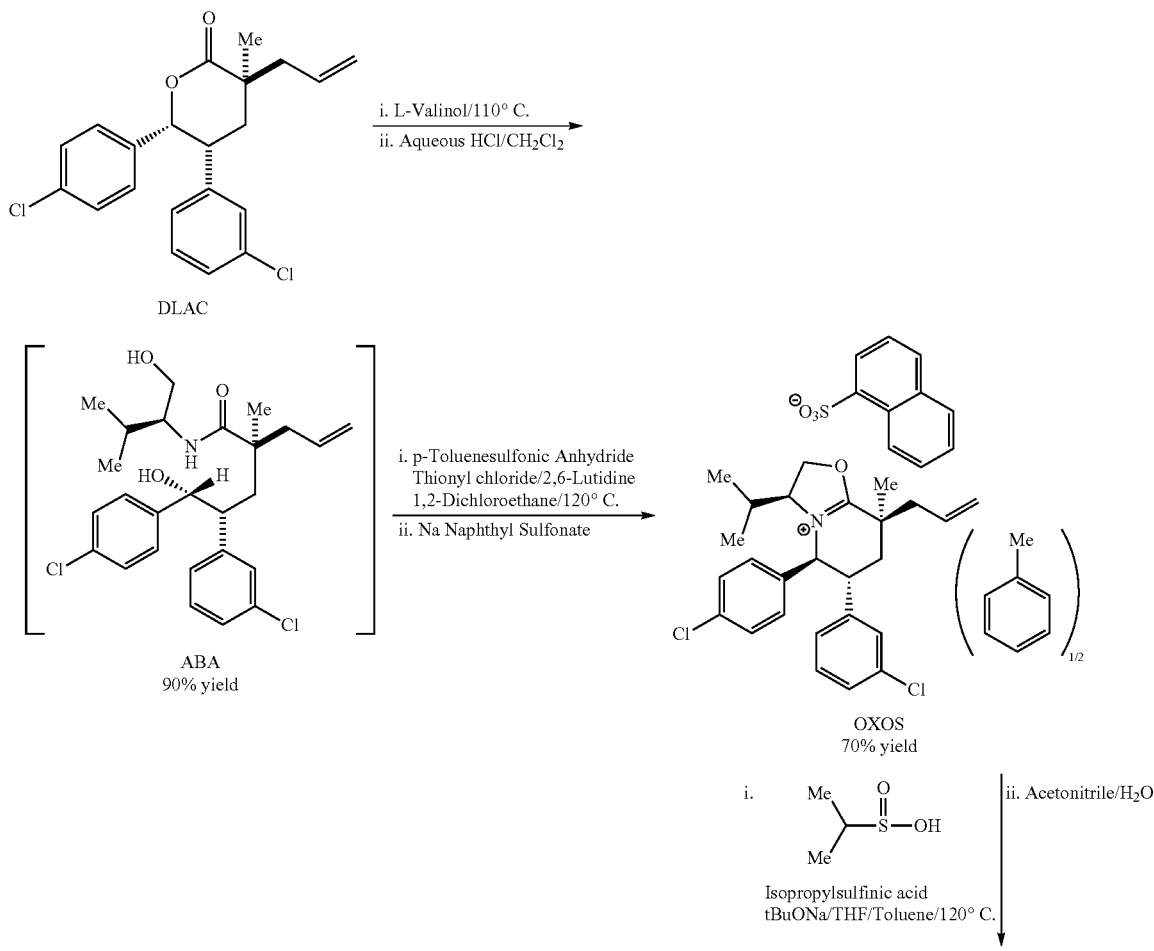

Scheme 1. First-in-human Process to Manufacture Compound A

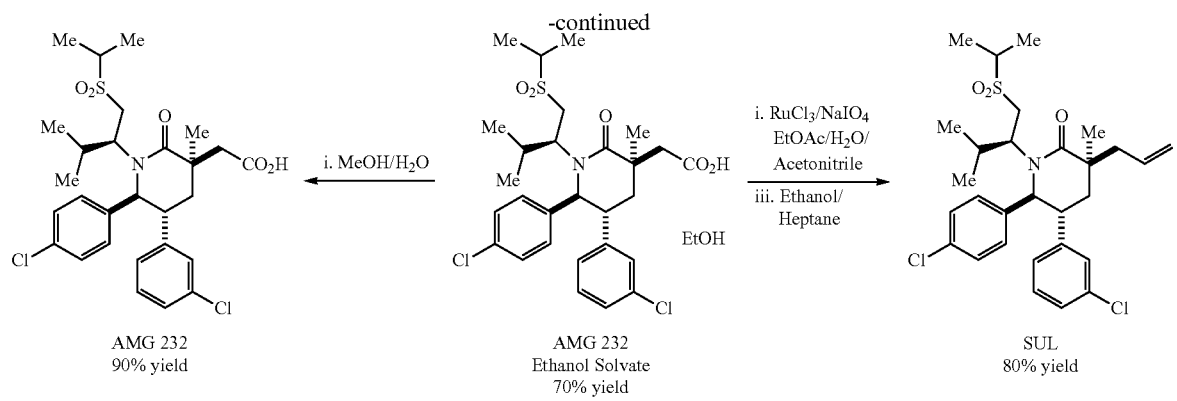
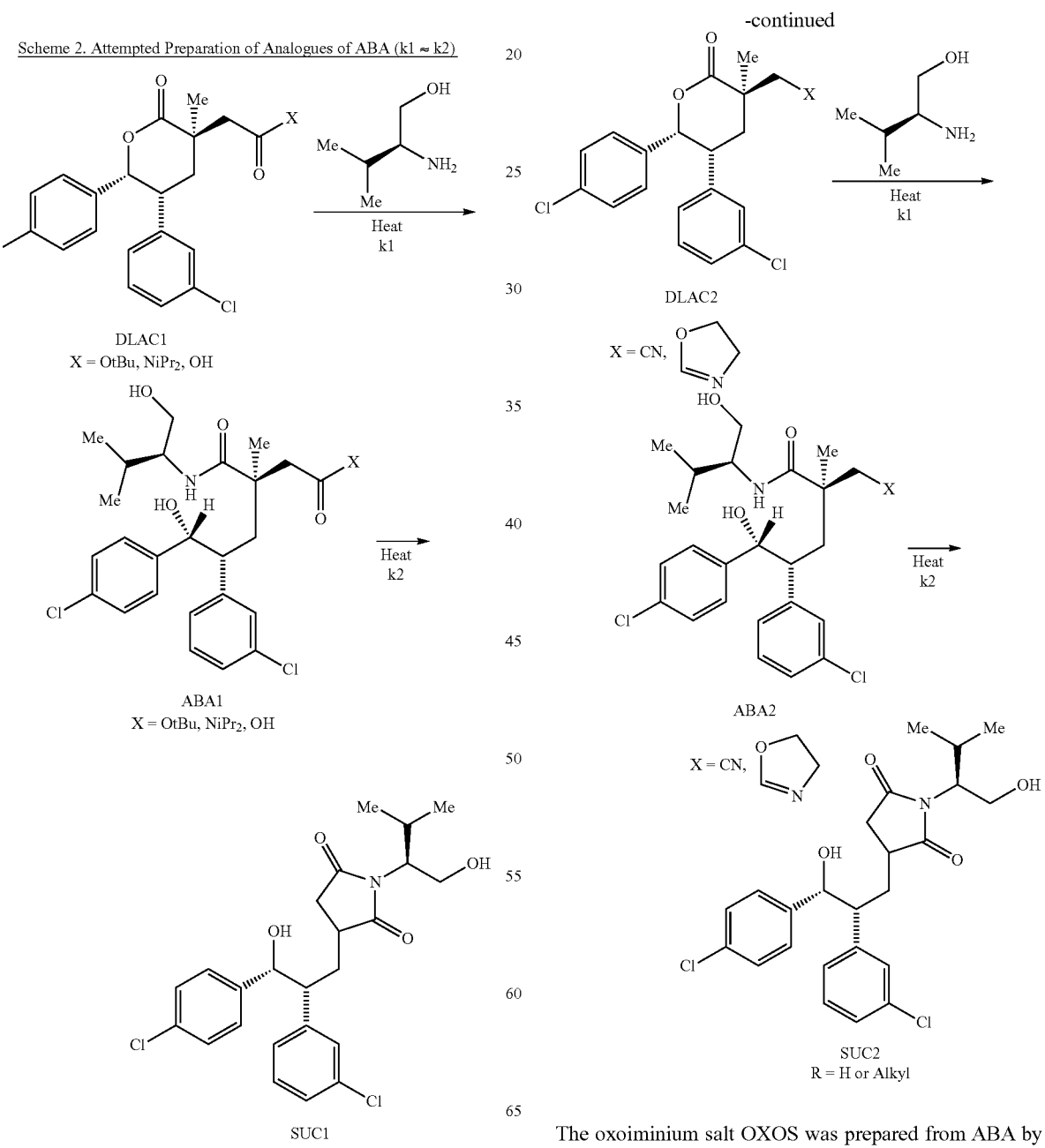
The oxoiminium salt OXOS was prepared from ABA by double activation with two equivalents of toluenesulfonic anhydride and 2,6-lutidine at elevated temperature. The cation thus prepared was isolated as a 2-naphthylsulfonic acid salt, which offered satisfactory impurity removal properties. Identifying an alternative reagent to toluenesulfonic anhydride (TsO₂) was contemplated for multiple reasons, including the need to eliminate the long lasting tosylate intermediate DHO-OTs, which underwent slow transformation to OXOS at elevated temperature (120° C.). This intermediate (DHO-OTs) is an alkylating agent and thus a potentially mutagenic impurity. One possible option considered was to isolate the crystalline intermediate DHO (Scheme 3) to increase control over the effective removal of impurities for a manufacturing sequence. However, this necessitated the use of a reagent which allowed for the selective chemoselective activation of the primary alcohol of ABA in the presence of the secondary benzylic alcohol. Sulfonic anhydrides reagents did not offer this advantage.

Scheme 3.
Intermediates in the Preparation of OXOS from ABA using Ts₂O

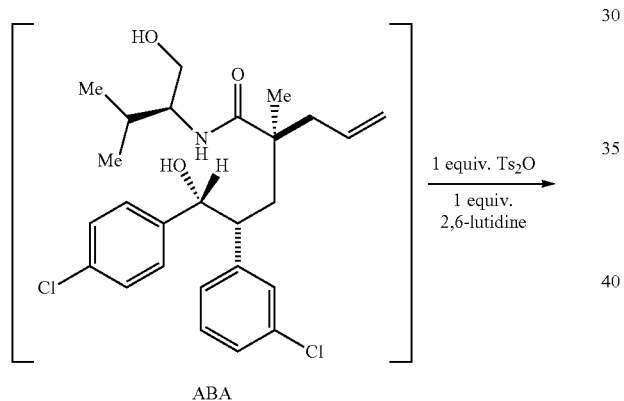

ABA 1 equiv. Ts₂O
1 equiv. 2,6-lutidine

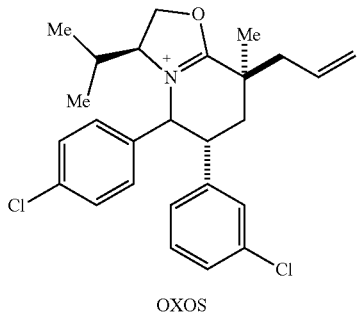

DHO 1 equiv. Ts₂O
1 equiv. 2,6-lutidine

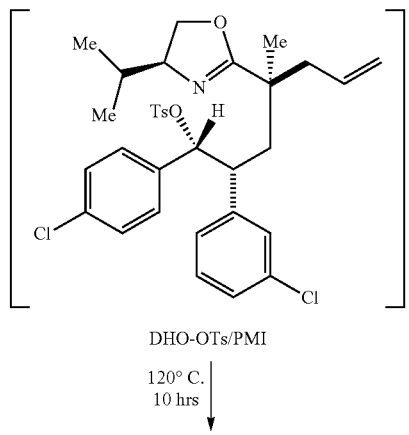

DHO-OTs/PMI

120° C.
10 hrs

OXOS

The preparation of SUL from OXOS was carried out by treatment of the OXOS with isopropylsulfinic acid in the presence of sodium t-butoxide. This transformation proceeds via reversible formation of a diastereomeric pair of sulfinate intermediates (SULFI) and subsequent rearrangement to the thermodynamic product SUL, which is crystallized from acetonitrile and water (Scheme 4). The ALC side product formed irreversibly under these conditions in the presence of water. Isopropylsulfinic acid, an oil at 20° C., was prepared from isopropylmagnesium chloride and isolated after an aqueous work-up. Azeotropic drying of this reagent was necessary prior to use in the formation of SUL to avoid generation of the undesired ALC side-product in large quantities. However, isopropyl sulfinate was observed to decompose via disproportionation upon drying and thus this unit operation was avoided. Consequently, the discovery of a stable crystalline salt of isopropylsulfinic acid which was stable under drying conditions and which may be designated as a commercial regulatory starting material was sought. Alternatively, a process for the in situ preparation of a sulfinic acid salt from isopropyl magnesium chloride without an aqueous work-up and further reaction with OXOS was considered.

Scheme 4. Intermediates and Side-Products Generalted in the Preparation of SUL from OXOS

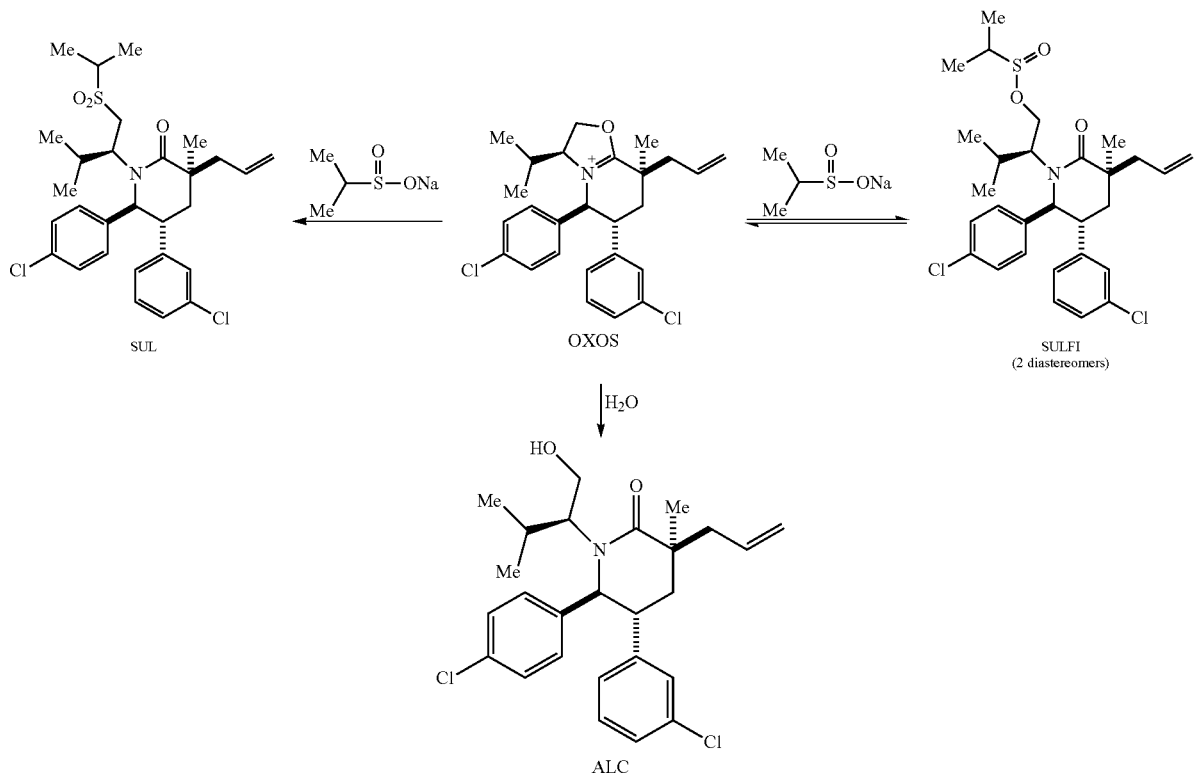

Oxidation of the alkene group of SUL was carried out via treatment with catalytic ruthenium chloride (2 mol %) and excess sodium periodate (5 equivalents). The crude product was isolated as a crystalline ethanol solvate. Several features of this step were observed to be undesirable. First, the heavy metal used in this step had to be scavenged, which was accomplished using a DARCO-G resin for the first-in-human delivery. Additionally, multiple equivalents of sodium periodate were necessary to carry out this process and the reagent had to be charged to the reaction vessel in portions to minimize impurity formation. A complex downstream treatment protocol (extractions and filtrations) was required to remove the large amounts of salts utilized for the transformation. Further, multiple dimeric impurities were generated in this transformation step, which made it challenging to control the purity of the drug substance. The use of an ethanol solvate of Compound A as a crystalline control point was problematic and was only moderately effective at removal of the impurities present in the mixture. In addition, the crystallization process had to be conducted as an evaporative process due to the low ethanol concentration (5% v/v) which was necessary to alleviate high mother liquor losses during filtration. The use of ethanol in the crystallization process was also observed to reduce the robustness of the process due to the undesired formation of the corresponding ethyl ester at temperatures above 30° C. and the difficulty experienced in removal of the ethyl ester from the desired ethanol solvate. Similarly, when methanol was used in the crystallization of Compound A, the formation of the corresponding methyl ester at elevated temperatures, which was also difficult to isolate away from the drug substance, significantly reduced the viability of this route for crystallization, especially when operating on multigram scale. Thus, the development of a more consistent and environmentally friendly oxidation process for the preparation of Compound A from SUL as well as the generation of a robust strategy for isolating the drug substance that exhibits the effective control of critical attributes were sought as part of a commercially viable process.

TABLE 1

Modifications to the FIH Process in the Commercial Process to Prepare Compound A

| CP1 Process Step | FIH Process | Commercial Process Solution |
| --- | --- | --- |
| ABA from DLAC | Three equivalents of L-Valinol used | Reduction of L-Valinol equivalents to two |
| OXOS from ABA | DHO is not isolated | Replacement of $TS_2O$ with a chemoselective reagent enabling isolation of DHO |
| OXOS from ABA | PMI and long-lasting intermediate DHO-OTs are formed | Replacement of $TS_2O$ with a reagent enabling the formation of an intermediate undergoing rapid conversion to OXOS |

TABLE 1-continued

Modifications to the FIH Process in the Commercial Process to Prepare Compound A

| CP1 Process Step | FIH Process | Commercial Process Solution |
|---|---|---|
| SUL from OXOS | Isopropylsulfinic acid is a liquid at 20° C. and is unstable to azeotropic drying conditions | Discovery of a crystalline salt of isopropylsulfinic acid salt that is stable under drying conditions |
| Compound A from SUL | Ruthenium catalyst is used in the last step | Change of reagents for the last step |
| Compound A from SUL | Excess (5 equiv) sodium periodate is used in last step | Change of reagents for the last step |
| Isolation of Compound A as an ethanol solvate | The isolation is only moderately effective at removal of impurities and is not well suited for crystallization design | Discovery of a salt of Compound A well suited to crystallization design and having superior impurity removal properties |
| Isolation of Compound A | The isolation is poorly effective at removal of the undesired corresponding methyl ester which can form in the crystallization system used (MeOH/H$_2$O) | Develop a new crystallization of the drug substance, Compound A, which is free from impurity formation |

Example 3: Development of a Commercial Process to Prepare the Intermediate OXOS

Figure 2:
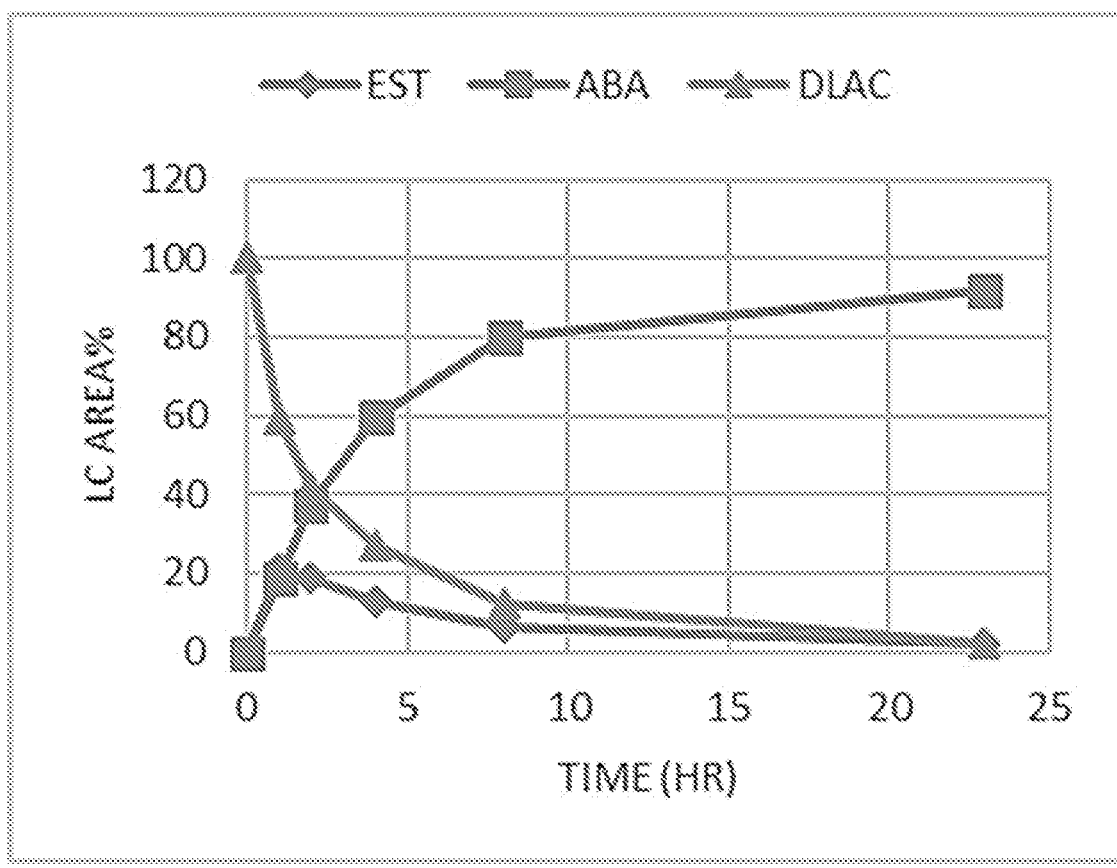
FIG. 2 illustrates the conversion rate of DLAC to ABA over time at 115° C.

The thermal amidation of DLAC to ABA with L-valinol proceeded through a multistep mechanism via intermediate ester EST (Scheme 5). The initial transesterification of DLAC to EST was determined to be a reversible process ($k_1 > k_{-1}$ with 2 equivalents of L-valinol) leading to a build-up of EST prior to rearrangement to the amide product ABA. Upon performing the reaction at 60° C., rapid conversion of DLAC to EST is observed at the start of the reaction followed by slow conversion of EST to ABA over the course of several days ($k_1 > k_2$) (FIG. 1). At elevated temperatures (115° C.) (FIG. 2), the rearrangement of EST to the more stable ABA is faster, resulting in an increase in the overall rate of the reaction by increasing the concentration of EST.

The FIH process utilized a thermal melt with 3 equivalents of L-valinol to ensure rapid conversion of DLAC to ABA at 110° C. Consistent with our mechanistic understanding of this transformation, decreasing L-valinol loading (from 3 equivalents to 2 equivalents) resulted in a decrease in the overall rate of the reaction since the conversion of DLAC to EST ($k_1$) directly impacts the relative concentration of EST. When 2 equivalents of L-valinol was used, the reaction was observed to require 72 hours to reach conversion at 115° C., while employing toluene (1 volume) to ensure reaction homogeneity. This longer processing time, however, may be considered justifiable based on significant cost reductions. Elimination of excess L-valinol was achieved by the addition of toluene (4 volumes) and subsequent washing of the organic mixture with an aqueous hydrochloric acid solution. The resultant organic solution was azeotropically dried and polish filtered to afford ABA in

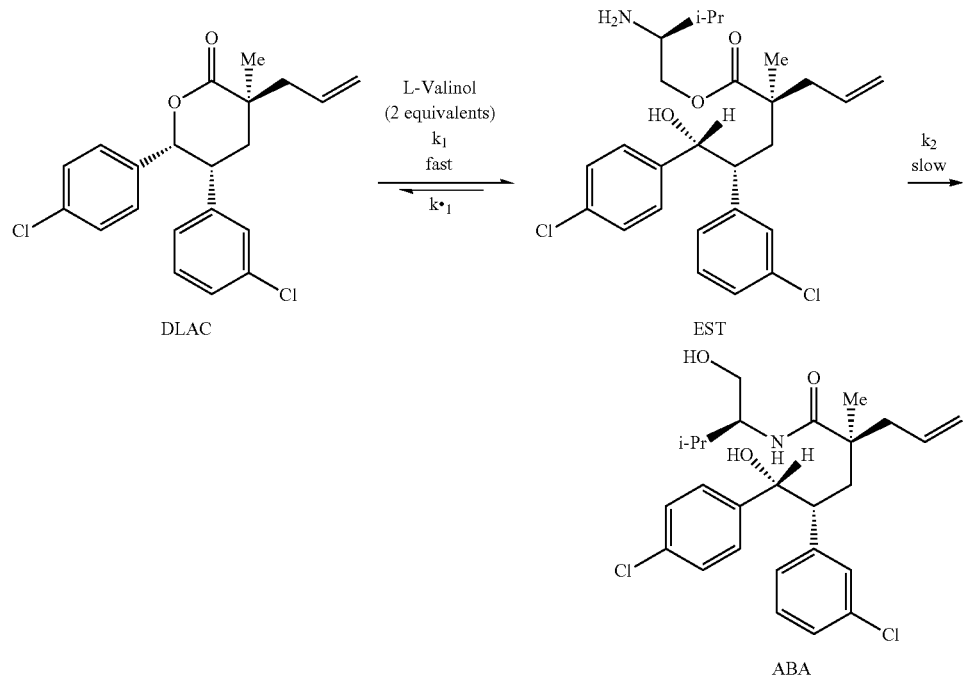

Scheme 5. Kinetics of Thermal Amidation of DLAC to ABA

91% assay yield as a 28 wt % solution in toluene containing 2.7 LC area % of DHO, 1.0 LC area % of starting material DLAC, and 1.0 LC area % of EST. Thermolysis of ABA to prepare directly DHO at higher temperatures led to complex mixtures of products.

The isolation of intermediate DHO provided an additional opportunity to remove impurities from the process stream and to strengthen the overall control strategy to deliver a drug substance for market application. Paramount to this strategy was the identification of conditions that would untether the dehydrative double-cyclization of ABA to OXOS into two distinct mono-cyclization reactions through the development of a chemoselective activation of the primary alcohol of ABA (conditions A) that would enable the isolation of DHO in crystalline form (Scheme 6).

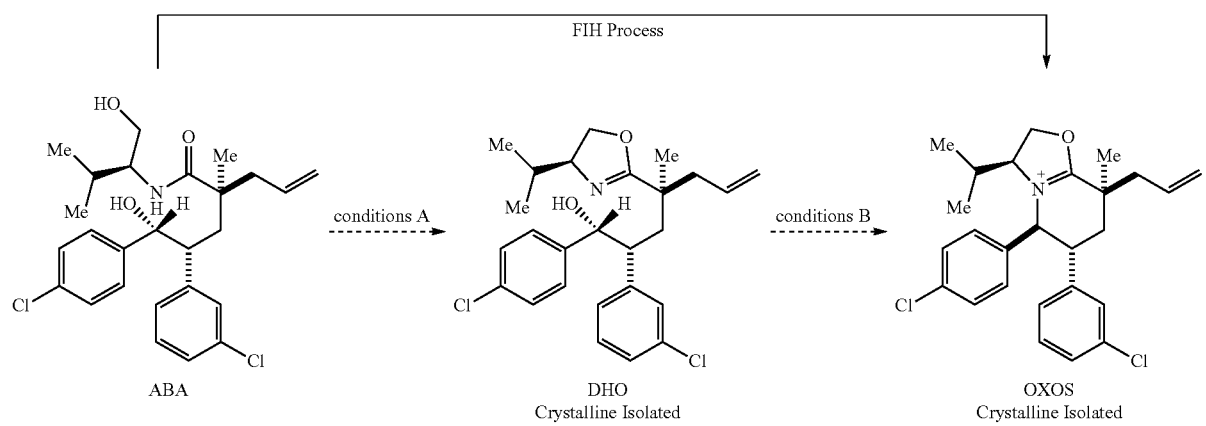

Scheme 6. Sequential Dehydration of ABA to OXOS

Sulfonyl chloride and sulfonic anhydride reagents were found to be unselective in discriminating between the primary and secondary alcohols of ABA and were difficult to procure as anhydrous reagents. Furthermore, the use of acid catalysts also afforded complex mixtures of products. However, a Vilsmeier salt reagent, methoxymethylene-N,N-dimethyliminium methyl sulfate, successfully achieved the desired selectivity. This reagent was easily prepared with no special precautions taken to exclude moisture and it can be stored at 20° C. for several months with no erosion in titer. Additionally, it exhibited milder reactivity and improved chemoselectivity compared to the common halide-derived Vilsmeier salt chloromethyl ene-N,N-dimethyliminium chloride and also avoided the formation of alkyl halide side-products. The formation of DHO from ABA using methoxymethylene-N,N-dimethyliminium methyl sulfate in toluene was evaluated in the presence of various mild inorganic bases at 25° C. and the conversion to DHO was recorded (Scheme 7). The reaction was observed to perform best with KOAc, but NaOAc was preferred, considering its low hygroscopicity and cost.

Scheme 7. Evalution of Various Bases in the Mono-Cyclization of ABA to DHO

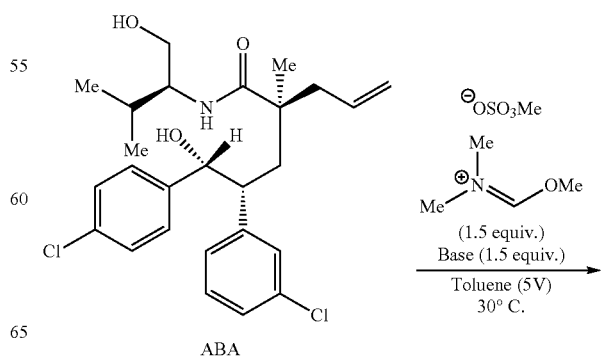

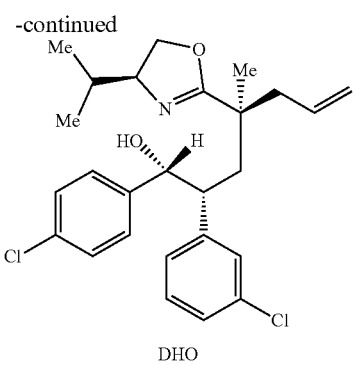

DHO

| Base | DHO assay yield % | Conversion time (hr) |
|---|---|---|
| KOAc | 94.6 | 2 |
| NaOAc | 91.9 | 2 |
| LiOAc | 86.5 | 20 |
| $K_2CO_3$ | 70.4 | 16 |

The desired chemoselectivity of this transformation is achieved through the unique ability of methoxymethylene-N,N-dimethyliminium methyl sulfate to undergo dynamic transesterification with alcohols through the generation of labile imidate intermediates. This reversibility was investigated in the activation of 4-chlorobenzyl alcohol (CHA) with the deuterated reagent DEU to generate imidate IMI, which was found to equilibrate at a 2.5/1 ratio of CHA/IMI (Scheme 8). Based on this observation, it is proposed that the IMABA exists in low concentrations during the reaction and undergoes a rapid intramolecular displacement with the pendant amide to generate oxazoline DHO (Scheme 8). Any imidate formed by derivatization of the secondary alcohol group of the ABA group does not undergo further cyclization to OXOS at the operating reaction temperature (30° C.).

Scheme 8. Reversible Activation of Alcohols with Vilsmeier Reagents

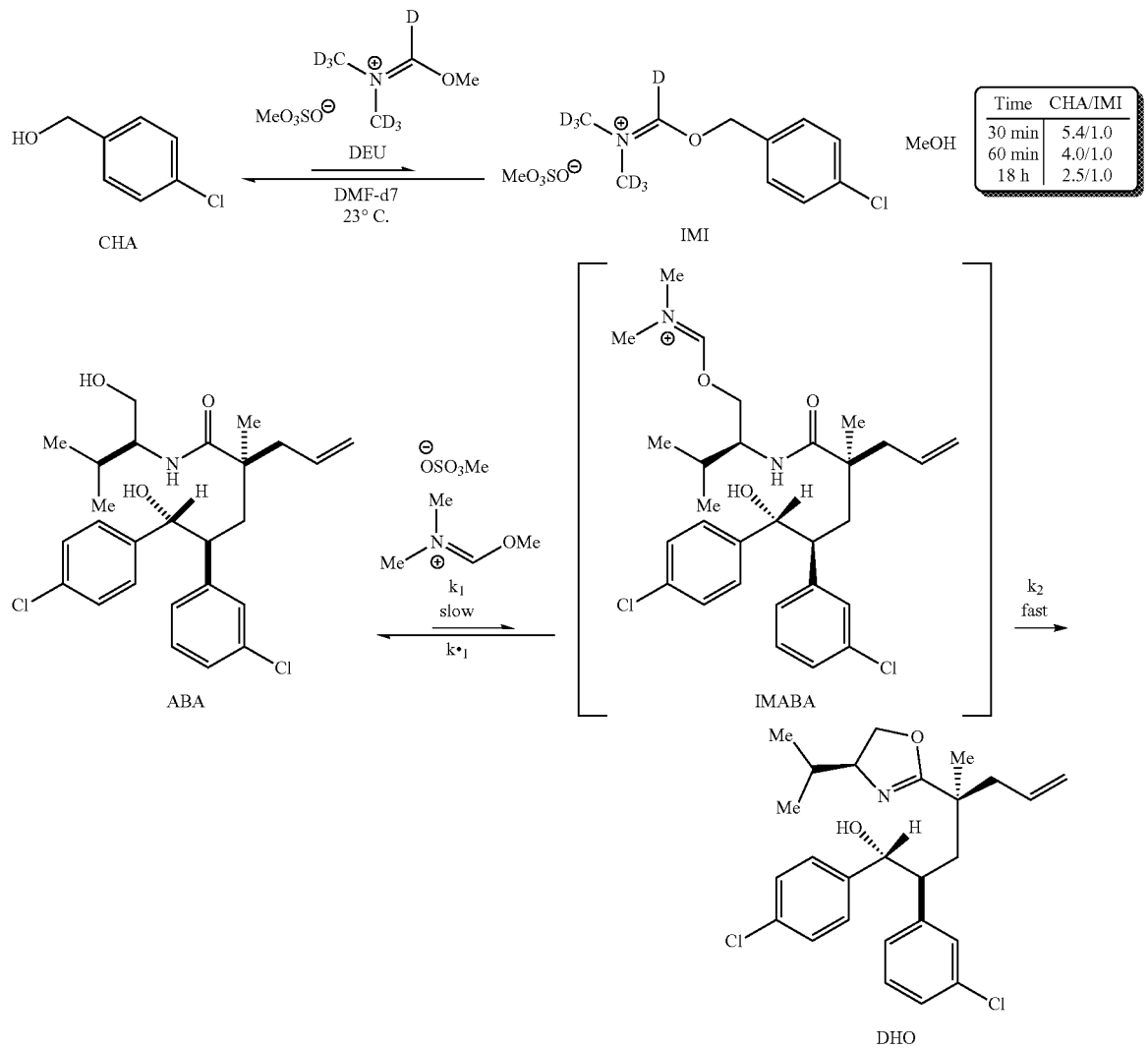

Figure 3:
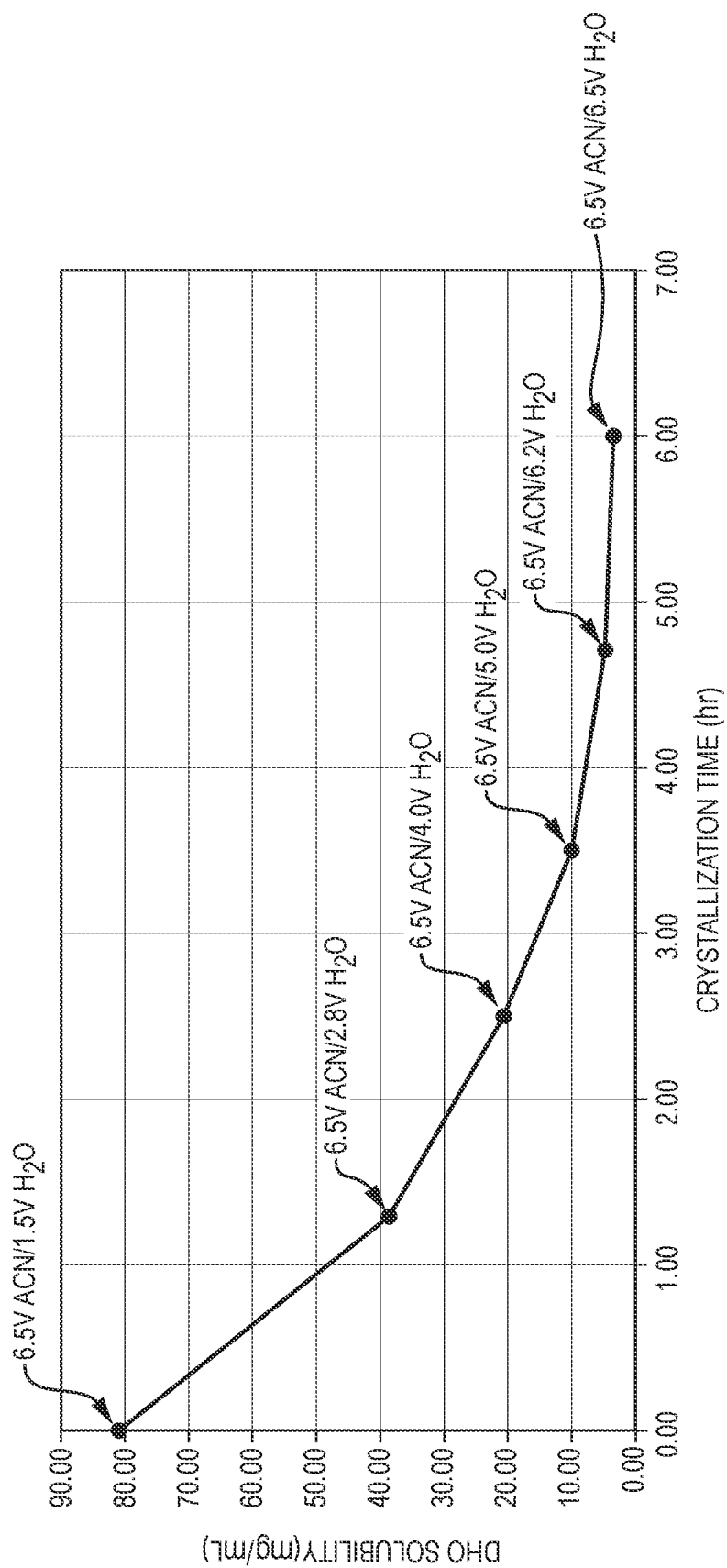
FIG. 3 illustrates the solubility of (1R,2R,4S)-2-(3-chlorophenyl)-1-(4-chlorophenyl)-4-((S)-4-isopropyl-4,5-dihydrooxazol-2-yl)-4-methylhept-6-en-1-ol (DHO) during the crystallization process at 25° C.

Equilibrium solubility measurements were gathered for DHO in various solvents. It was observed that all values obtained were above 20 mg/mL at 20° C. (including heptane) except for water (<0.1 mg/mL), which was thus selected as an anti-solvent. Acetonitrile was selected as a solvent for crystallization as it resulted in the facile removal of impurities when in combination with water. A curve showing solubility values at different time points in the crystallization process is presented in FIG. 3. Using this protocol, crystalline DHO was isolated in 88% yield from DLAC in a >98 LC area % (Scheme 9).

Figure 17:
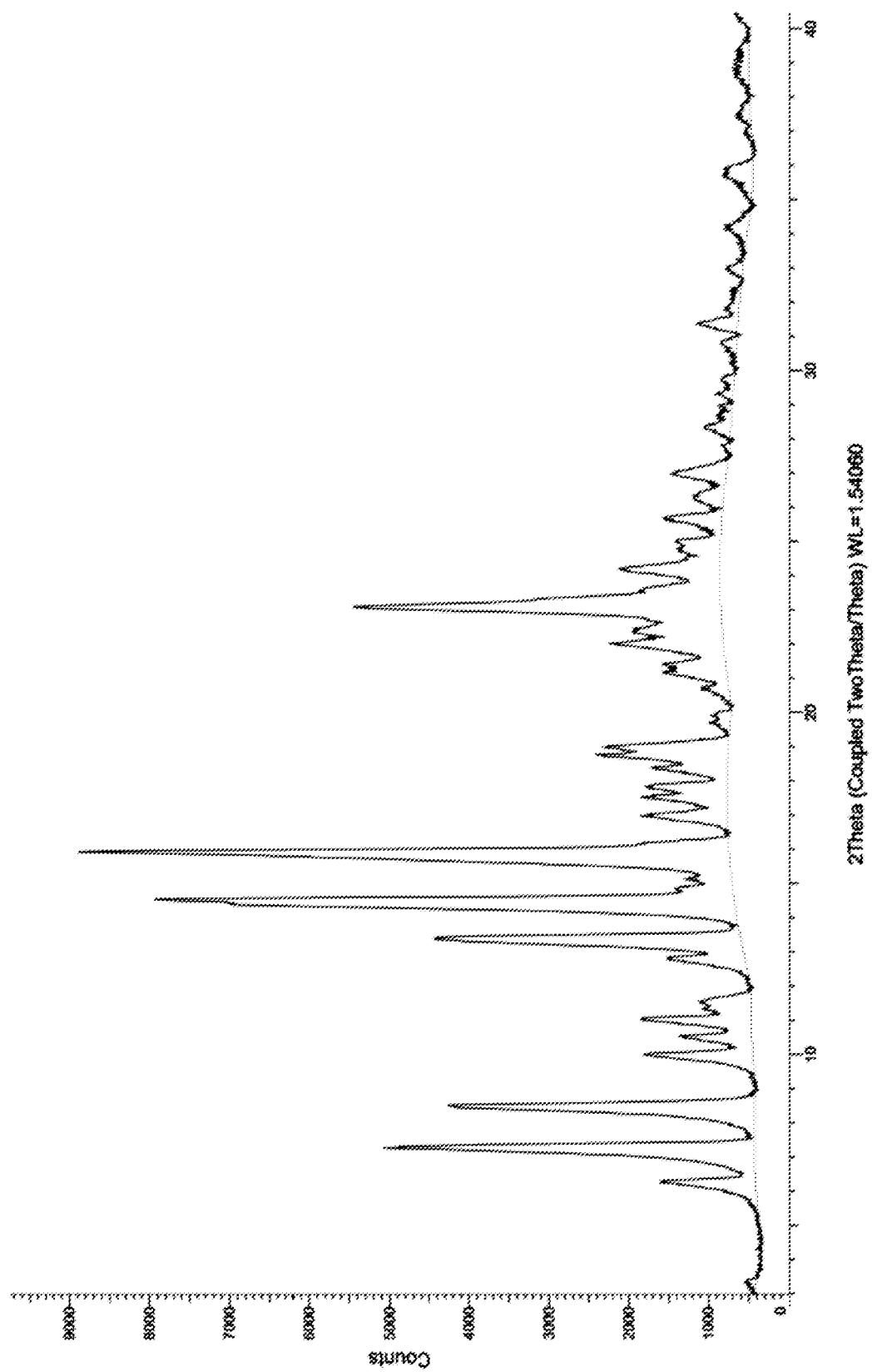
FIG. 17 illustrates a powder X-ray diffraction (PXRD) pattern of crystalline DHO measured in reflection mode.
Figure 18:
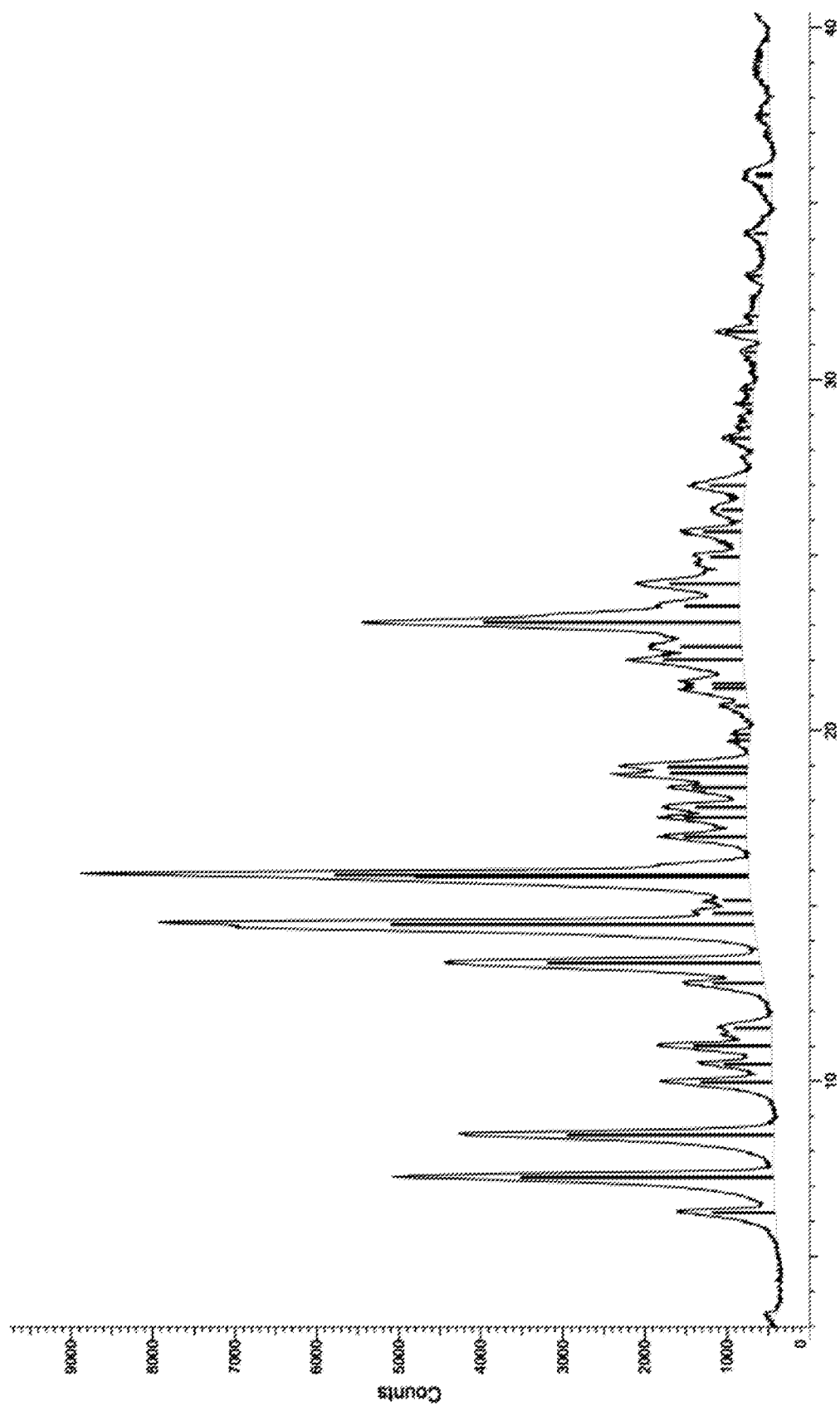
FIG. 18 illustrates a powder X-ray diffraction (PXRD) pattern of crystalline DHO measured in reflection mode with sticks, indicating the peak positions.

A Bruker D8 powder X-ray diffractometer was used to acquire reflection PXRD pattern of the crystalline DHO (FIG. 17) and was equipped with a Braun detector and a Cu—Kα radiation source operating in Bragg-Brentano reflection geometry. The obtained 2-theta (2θ) values were generally accurate to within an error of ±0.2°. The samples were generally prepared without any special treatment other than the application of slight pressure to achieve a flat surface. Samples were measured uncovered unless otherwise noted. Operating conditions included a tube voltage of 40 kV and current of 40 mA. A variable divergence slit was used with a 3° window. The step size was 0.019° 2θ with a step time of 35.2 seconds. The sample was static during the measurement.

The peaks listed in Table 2 were identified in the PXRD pattern of crystalline DHO.

TABLE 2

PXRD peaks for crystalline DHO

| Peak | Angle | d Value | Intensity | Rel. Intensity |
|---|---|---|---|---|
| 1 | 6.3 | 14.12344 | 753 | 14.90% |
| 2 | 7.3 | 12.15811 | 3080 | 61.10% |
| 3 | 8.5 | 10.43913 | 2521 | 50.00% |
| 4 | 10.0 | 8.86434 | 871 | 17.30% |
| 5 | 10.5 | 8.42517 | 569 | 11.30% |
| 6 | 11.0 | 8.03156 | 934 | 18.50% |
| 7 | 11.5 | 7.6782 | 448 | 8.90% |
| 8 | 12.8 | 6.9125 | 618 | 12.30% |
| 9 | 13.4 | 6.61879 | 2598 | 51.50% |
| 10 | 14.5 | 6.11557 | 4427 | 87.80% |
| 11 | 14.8 | 5.98483 | 474 | 9.40% |
| 12 | 15.2 | 5.84027 | 331 | 6.60% |
| 13 | 15.9 | 5.57383 | 5042 | 100.00% |
| 14 | 15.8 | 5.59708 | 4060 | 80.50% |
| 15 | 17.0 | 5.22058 | 757 | 15.00% |
| 16 | 17.5 | 5.0574 | 749 | 14.80% |
| 17 | 17.8 | 4.97509 | 613 | 12.20% |
| 18 | 18.4 | 4.82391 | 662 | 13.10% |
| 19 | 18.8 | 4.72167 | 937 | 18.60% |
| 20 | 19.0 | 4.67741 | 969 | 19.20% |
| 21 | 19.7 | 4.49805 | 165 | 3.30% |
| 22 | 19.9 | 4.46033 | 169 | 3.30% |
| 23 | 20.7 | 4.28732 | 168 | 3.30% |
| 24 | 21.2 | 4.18605 | 394 | 7.80% |
| 25 | 21.3 | 4.16028 | 399 | 7.90% |
| 26 | 22.0 | 4.03425 | 963 | 19.10% |
| 27 | 22.4 | 3.96797 | 741 | 14.70% |
| 28 | 23.1 | 3.84953 | 3121 | 61.90% |
| 29 | 23.6 | 3.77436 | 665 | 13.20% |
| 30 | 24.2 | 3.67661 | 840 | 16.70% |
| 31 | 24.9 | 3.56615 | 357 | 7.10% |
| 32 | 25.7 | 3.46767 | 455 | 9.00% |
| 33 | 26.3 | 3.38729 | 262 | 5.20% |
| 34 | 27.0 | 3.30081 | 434 | 8.60% |
| 35 | 28.3 | 3.1469 | 248 | 4.90% |
| 36 | 28.7 | 3.11305 | 62.8 | 1.20% |
| 37 | 29.3 | 3.04435 | 167 | 3.30% |
| 38 | 29.7 | 3.00202 | 118 | 2.30% |
| 39 | 30.8 | 2.9015 | 135 | 2.70% |
| 40 | 31.4 | 2.84914 | 381 | 7.50% |
| 41 | 31.8 | 2.80958 | 113 | 2.20% |

TABLE 2-continued

PXRD peaks for crystalline DHO

| Peak | Angle | d Value | Intensity | Rel. Intensity |
|---|---|---|---|---|
| 42 | 33.0 | 2.71451 | 159 | 3.20% |
| 43 | 34.2 | 2.62156 | 161 | 3.20% |
| 44 | 35.8 | 2.50313 | 201 | 4.00% |
| 45 | 37.0 | 2.42816 | 39.5 | 0.80% |
| 46 | 37.5 | 2.39507 | 112 | 2.20% |

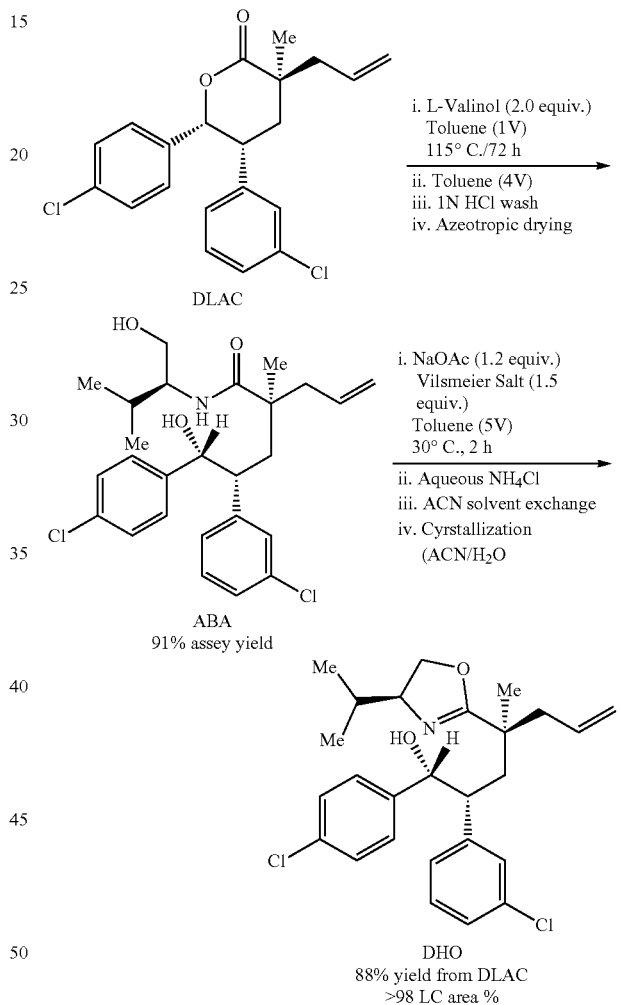

Scheme 9. Commerical Process to Prepare DHO and DLAC

Having untethered the double dehydrative cyclization of ABA to OXOS, development of a method to convert DHO to OXOS was needed. Methanesulfonic anhydride (Ms$_2$O) was found to provide a faster conversion to OXOS compared to Ts$_2$O, as potentially mutagenic mesylate intermediate DHO-OMs is completely consumed at 75° C. in 10 hours. This improvement is likely due to the reduced steric hindrance experienced in the transition state leading from DHO-OMs to OXOS compared to that involved in the cyclization of DHO-OTs to OXOS. The transformation was found to proceed well with 2,6-lutidine as a base in toluene. Nucleophilic organic bases and inorganic bases undesirably afforded complex mixtures of products. The mesylate salt of OXOS generated during the transformation is poorly soluble in toluene and forms a separate liquid layer as the reaction progresses. To enable further processing, it is necessary to dilute the reaction mixture with dichloromethane (8V) prior to removal of the mesylate salts using aqueous sulfuric acid washes. Salt metathesis with aqueous sodium 1-naphthalenesulfonate was followed by distillation of dichloromethane, leading to the crystallization of a 1-naphthalenesulfonate toluene hemi-solvate OXOS salt in 90% yield, 99.5 LC area %, and 99.7 wt % from DHO (Scheme 10).

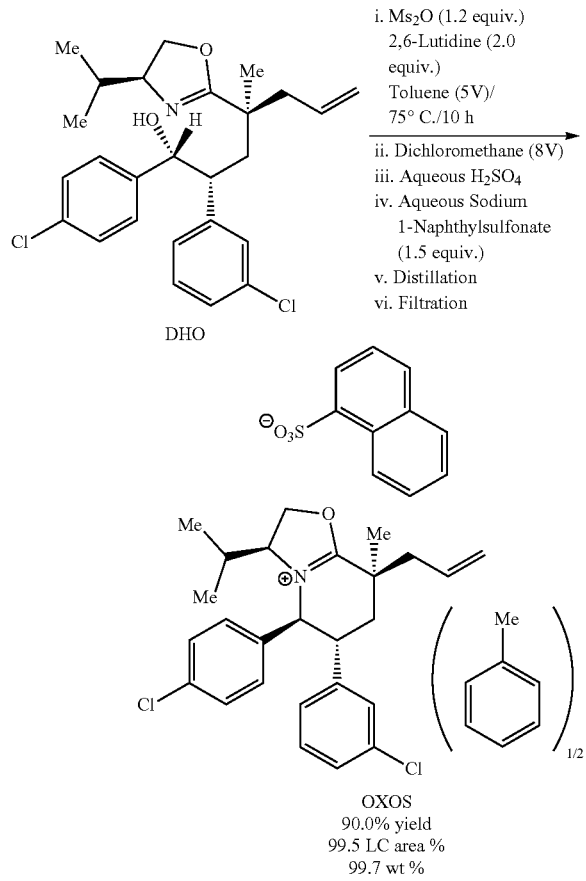

The following experimental procedures illustrate the preparation of OXOS.

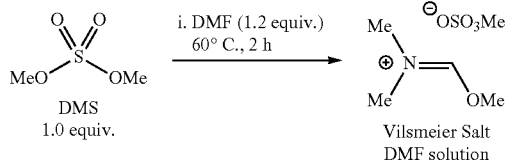 [SMILES: COS(=O)(=O)OC ; COC=[N+](C)C]

N,N-Dimethylformamide dimethyl sulfate adduct: A 500-mL Atlas reactor affixed with a reflux condenser and overhead stirring shaft was charged with dimethyl sulfate (200.0 mL, 2.11 mol, 1.0 equiv.) under a nitrogen atmosphere. The contents of the reactor were warmed to 60° C. DMF (200.0 mL, 2.56 mol, 1.2 equiv.) was added dropwise over 60 minutes (3.3 mL/min). Upon completion of addition, the reaction was stirred for 2 hours at 60° C. Upon completion of the reaction, the reaction was cooled to room temperature to afford the N,N-dimethylformamide dimethyl sulfate adduct as a solution in residual DMF (402.6 g, 2.02 mol, 95.8% assay yield, 82.8 wt % in DMF).

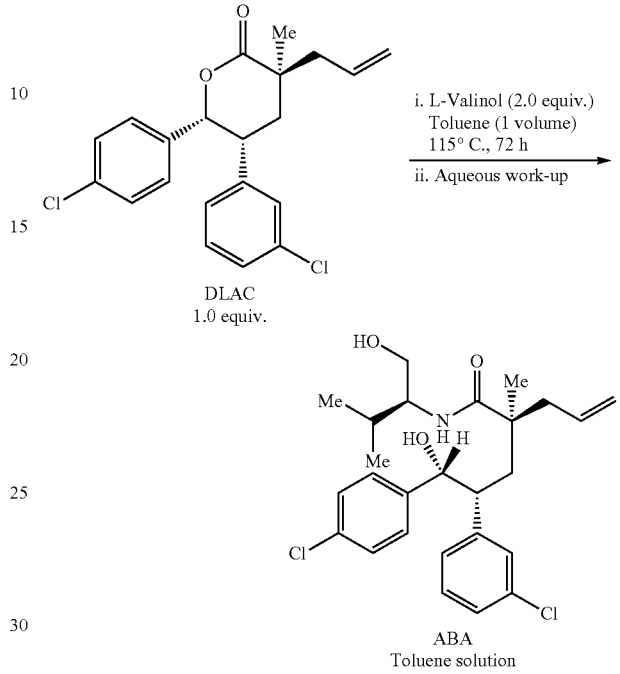

(S)-2-((2R,3R)-2-(3-chlorophenyl)-3-(4-chlorophenyl)-3-hydroxypropyl)-N—((S)-1-hydroxy-3-methylbutan-2-yl)-2-methylpent-4-enamide (ABA): A 5-L ChemGlass reactor affixed with a reflux condenser and overhead stirring shaft was charged with (3S,5R,6R)-3-allyl-5-(3-chlorophenyl)-6-(4-chlorophenyl)-3-methyltetrahydro-2H-pyran-2-one (DLAC) (201.8 g, 0.53 mol, 98.6 wt %, 1.0 equiv.), L-valinol (110.8 g, 1.06 mol, 2.0 equiv.), and toluene (205 mL, 1 mL/g) under a nitrogen atmosphere. The contents of the reactor were heated under reflux (115° C.) with constant stirring for 72 hours. Upon completion of the reaction, the reaction was cooled to room temperature and diluted with toluene (800 mL, 5 mL/g). The reaction was quenched by portion wise addition of 1N HCl (1000 mL, 5 mL/g). The phases were split and the organic layer was subsequently washed twice with brine (2×400 mL, 2 mL/g). The organic phase was dried over magnesium sulfate, filtered through a polish filter (coarse porosity) while rinsing with toluene, and concentrated to a volume of approximately 800 mL to afford ABA as a solution in toluene (229.4 g, 0.48 mol, 90.5% assay yield, 27.9 wt % in toluene). $^1$H NMR (400 MHz, CHLOROFORM-d) δ ppm: 7.05-7.19 (m, 5H), 6.95 (d, J=8.50 Hz, 2H), 6.84 (d, J=7.67 Hz, 1H), 5.85 (d, J=8.09 Hz, 1H), 5.57 (ddt, J=17.13, 9.98, 7.28, 7.28 Hz, 1H), 4.91-5.03 (m, 2H), 4.71 (d, J=4.77 Hz, 1H), 3.66 (br s, 1H), 3.57-3.63 (m, 1H), 3.51-3.53 (m, 1H), 3.42-3.46 (m, 1H), 3.19 (br s, 1H), 2.97 (dt, J=7.93, 4.95 Hz, 1H), 2.36 (dd, J=13.89, 7.05 Hz, 1H), 2.13 (dd, J=14.62, 4.87 Hz, 1H), 1.96-2.01 (m, 1H), 1.87-1.92 (m, 1H), 1.71-1.82 (m, 1H), 1.10 (s, 3H), 0.88 (d, J=7.05 Hz, 3H), 0.86 (d, J=7.05 Hz, 3H). $^{13}$C NMR (101 MHz, CHLOROFORM-d) δ ppm: 177.47, 142.83, 140.46, 133.79, 133.67, 133.00, 129.49, 129.12, 127.96, 127.93, 127.68, 126.88, 118.64, 75.91, 63.44, 56.94, 49.51, 45.17, 42.13, 39.59, 29.06, 24.07, 19.40, 18.72.

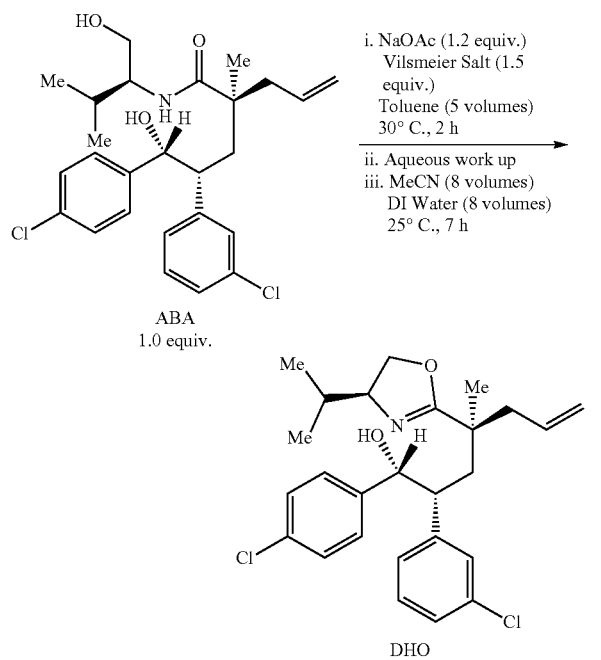

ABA
1.0 equiv.

DHO

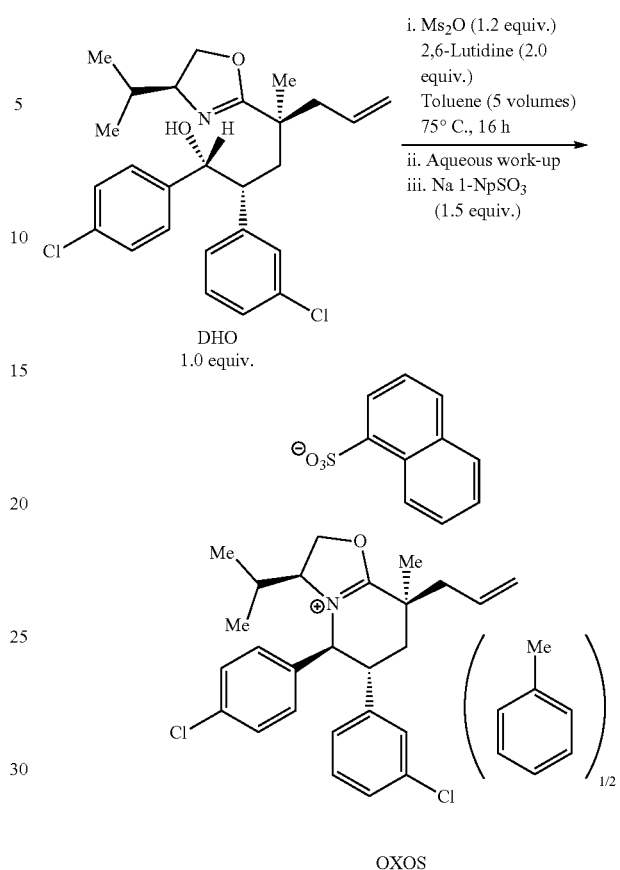

DHO
1.0 equiv.

OXOS (1R,2R,4S)-2-(3-chlorophenyl)-1-(4-chlorophenyl)-4-((S)-4-isopropyl-4,5-dihydrooxazol-2-yl)-4-methylhept-6-en-1-ol (DHO): A 5-L ChemGlass reactor affixed with a reflux condenser and overhead stirring shaft was charged with (S)-2-((2R,3R)-2-(3-chlorophenyl)-3-(4-chlorophenyl)-3-hydroxypropyl)-N—((S)-1-hydroxy-3-methylbutan-2-yl)-2-methylpent-4-enamide (ABA) (229.4 g, 0.48 mol, 27.9 wt % in toluene, 1.0 equiv.) and toluene (1145 mL, 5 mL/g) under a nitrogen atmosphere. (Note: since ABA is obtained as a stock solution in toluene containing 685 mL of residual toluene, the amount of additional toluene needed is 460 mL). The contents of the reactor were warmed to 30° C. NaOAc (48.3 g, 0.59 mol, 1.2 equiv.) and N,N-dimethylformamide dimethyl sulfate adduct (174.1 g, 0.72 mol, 82.8 wt %, 1.5 equiv.) were sequentially added to the reaction. After stirring at 30° C. for 2 hours, the reaction was cooled to room temperature. The reaction was quenched with sat. aq. $NH_4Cl$ (750 mL, 3 mL/g) and $H_2O$ (500 mL, 2 mL/g). The phases were split and the organic layer was subsequently washed twice with brine (2×750 mL, 3 mL/g). The organic phase was dried over magnesium sulfate, filtered through a polish filter (coarse porosity) while rinsing with toluene, and concentrated in vacuo. The crude residue was recrystallized from MeCN:$H_2O$ (50:50) to afford DHO as a white crystalline solid (206.5 g, 0.45 mol, 87.7% yield over 2 steps corrected by wt %). $^1H$ NMR (400 MHz, CHLOROFORM-d) δ ppm: 7.07-7.21 (m, 5H), 6.99 (d, J=8.29 Hz, 2H), 6.88 (d, J=7.10 Hz, 1H), 5.44-5.55 (m, 1H), 4.83-4.97 (m, 2H), 4.73 (d, J=5.60 Hz, 1H), 4.42 (br s, 1H), 4.03 (dd, J=8.91, 7.67 Hz, 1H), 3.63-3.76 (m, 2H), 3.15-3.21 (m, 1H), 2.35 (dd, J=13.89, 7.26 Hz, 1H), 2.13-2.18 (m, 1H), 2.07-2.12 (m, 1H), 1.84 (dd, J=14.72, 8.09 Hz, 1H), 1.48-1.60 (m, 1H), 1.09 (s, 3H), 0.94 (d, J=6.63 Hz, 3H), 0.82 (d, J=6.63 Hz, 3H). $^{13}C$ NMR (101 MHz, CHLOROFORM-d) δ ppm: 171.99, 143.48, 140.41, 133.74, 133.35, 132.92, 129.55, 129.09, 128.24, 127.84, 127.75, 126.75, 118.33, 76.63, 71.80, 69.84, 49.36, 42.13, 39.72, 38.61, 32.48, 24.20, 19.10, 18.26.

(3S,5S,6R,8S)-8-allyl-6-(3-chlorophenyl)-5-(4-chlorophenyl)-3-isopropyl-8-methyl-2,3,5,6,7,8-hexahydrooxazolo[3,2-c]pyridin-4-ium naphthalene-1-sulfonate toluene hemisolvate (OXOS): A 5-L ChemGlass reactor affixed with a reflux condenser and overhead stirring shaft was charged with (1R,2R,4S)-2-(3-chlorophenyl)-1-(4-chlorophenyl)-4-((S)-4-isopropyl-4,5-dihydrooxazol-2-yl)-4-methylhept-6-en-1-ol (DHO) (199.3 g, 0.40 mol, 93.5 wt %, 1.0 equiv.) and toluene (1000 mL, 5 mL/g) under a nitrogen atmosphere. Methanesulfonic anhydride (88.2 g, 0.49 mol, 1.2 equiv.) and 2,6-lutidine (95.0 mL, 0.82 mol, 2.0 equiv.) were sequentially added to the reaction. The contents of the reactor were heated to 75° C. with constant stirring for 16 hours. Upon completion of the reaction, the reaction was cooled to room temperature and diluted with dichloromethane (1600 mL, 8 mL/g). The reaction was quenched with a solution of conc. $H_2SO_4$ (45.0 mL, 0.82 mol, 2.0 equiv.) in $H_2O$ (955 mL, 5 mL/g). The phases were split and the organic layer was subsequently washed twice with an aqueous solution of sodium 1-naphthalenesulfonate (2×72.5 g, 0.31 mol, 0.75 equiv.) in $H_2O$ (2×800 mL, 4 mL/g). The organic phase was dried over sodium 1-naphthalenesulfonate (10.0 g, 0.04 mol, 0.1 equiv.), filtered through a polish filter (coarse porosity) while rinsing with dichloromethane, and concentrated in vacuo. The crude residue was recrystallized from toluene to afford OXOS as an off-white crystalline solid (260.1 g, 0.37 mol, 90.0% yield corrected by wt %). $^1H$ NMR (400 MHz, CHLOROFORM-d) δ ppm: 9.14 (d, J=8.50 Hz, 1H), 8.35 (dd, J=7.26, 1.24 Hz, 1H), 7.86 (t, J=8.71 Hz, 2H), 7.57 (t, J=7.70 Hz, 1H), 7.43-7.50 (m, 2H), 7.13-7.39 (m, 7.5H), 7.03-7.10 (m, 3H), 6.07 (d, J=11.20 Hz, 1H), 5.80 (ddt, J=17.00, 9.90, 7.39, 7.39 Hz, 1H), 5.51 (t, J=9.74 Hz, 1H), 5.26-5.34 (m, 2H), 4.76 (ddd, J=10.37, 4.66, 2.18 Hz, 1H), 4.62 (dd, J=9.12, 4.77 Hz, 1H), 3.51-3.60 (m, 1H), 2.86 (t, J=13.68 Hz, 1H), 2.65-2.71 (m, 1H), 2.55-2.60 (m, 1H), 2.35 (s, 1.5H), 1.95 (dd, J=13.89, 3.52 Hz, 1H), 1.52 (s, 3H), 0.54-0.67 (m, 7H). $^{13}$C NMR (101 MHz, CHLOROFORM-d) δ ppm: 183.28, 142.16, 140.01, 137.71, 135.89, 134.15, 134.12, 133.28, 132.15, 130.38, 130.30, 129.95, 129.62, 129.43, 129.06, 128.90, 128.34, 128.09, 127.92, 127.66, 127.41, 127.18, 126.44, 125.88, 125.63, 125.48, 125.16, 124.28, 121.20, 73.14, 67.27, 67.06, 43.64, 43.01, 38.67, 38.56, 26.64, 22.13, 21.32, 18.08, 13.74.

Alternatively, the intermediate DHO-OMs can be separated and purified before conversion to OXOS.

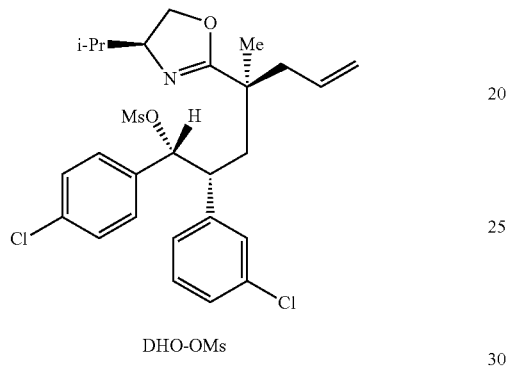

DHO-OMs $^1$H NMR (400 MHz, CHLOROFORM-d) δ ppm: 7.31 (d, J=8.4 Hz, 2H), 7.24-7.18 (m, 2H), 7.16 (s, 1H), 7.08 (d, J=8.2 Hz, 2H), 7.07-7.01 (m, 1H), 5.59-5.43 (m, 2H), 5.01-4.83 (m, 2H), 3.84 (dd, J=8.1, 9.5 Hz, 1H), 3.55-3.45 (m, 1H), 3.42-3.34 (m, 1H), 3.24-3.13 (m, 1H), 2.46 (s, 3H), 2.39-2.28 (m, 1H), 2.28-2.14 (m, 1H), 1.98 (br dd, J=7.8, 13.6 Hz, 1H), 1.72 (dd, J=2.4, 14.3 Hz, 1H), 1.26 (br s, 1H), 1.06 (s, 3H), 0.88 (d, J=6.7 Hz, 3H), 0.71 (d, J=6.7 Hz, 3H). $^{13}$C NMR (101 MHz, CHLOROFORM-d) δ ppm: 169.69, 141.54, 135.61, 134.98, 133.92, 133.43, 129.82, 129.30, 128.81, 128.47, 127.82, 127.34, 118.21, 87.02, 77.22, 69.78, 47.99, 44.57, 39.96, 39.31, 38.46, 32.80, 21.85, 19.40, 18.26.

Example 4: Development of a Commercial Process to Prepare Penultimate Intermediate SUL The treatment of OXOS with an isopropylsulfinate salt at elevated temperatures lead to the formation of the diastereomeric pair of sulfinate esters SULFI (Scheme 4) which rearranged to the more thermodynamically stable product SUL. This type of sulfinate-sulfone rearrangement has been described in conventional processes to occur via an ion pair formation and a recombination mechanism for benzhydryl sulfinate esters. However, in present process, the results of a cross-over experiment, shown in Scheme 11, reveals that the rearrangement involves dissociated ions. Considering that OXOS reacts quantitatively with water at temperatures above 70° C., there is ample opportunity for the alcohol ALC to be generated. Unless OXOS can be re-generated from ALC, water must be rigorously excluded from the reaction mixture. One path for achieving this objective is to prepare a salt of isopropylsulfinic acid which is stable to azeotropic drying conditions, can be isolated in high purity, and efficiently reacts with OXOS to generate SUL.

Scheme 11. Intermediates and Side-Products Generated in the Preparation of SUL from OXOS

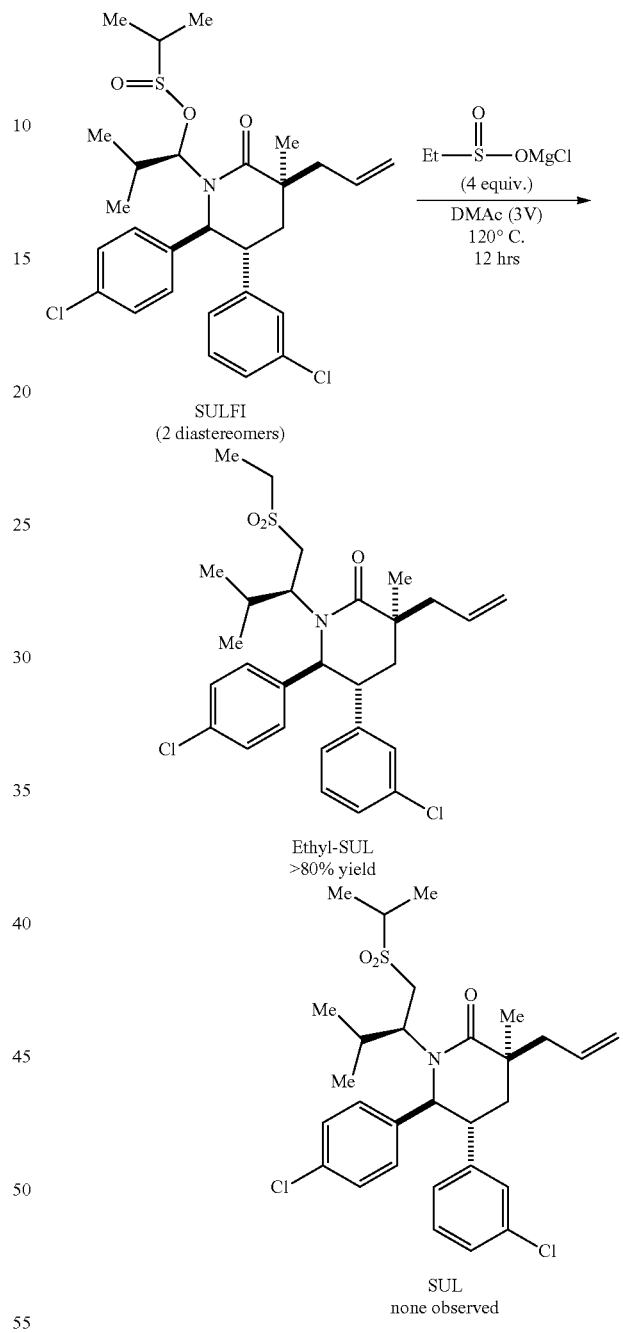

After the evaluation of several isopropylsufinic acid salt candidates to achieve this objective, including the lithium, sodium, potassium, magnesium and ammonium salts, the calcium sulfinate dihydrate salt stood out as a stable and crystalline species. This salt was prepared from the reaction of isopropyl magnesium chloride with sulfur dioxide (Scheme 12), leading to the formation of isopropylsulfinic acid after an aqueous hydrochloric acid quench. This material was treated with calcium acetate, which allowed for the isolation of the calcium isopropylsulfinate dihydrate (CALID) via a reactive crystallization. While a hydrate is not the ideal species for use in the preparation of SUL considering the water sensitivity of the process described above, the calcium salt was chemically stable (i.e., no disproportionation product observed in 48 hours) upon azeotropic drying in toluene at elevated temperature (up to 110° C.). Thus, drying of the reagent suspension can be included as part of the process prior to the addition of OXOS and the preparation of SUL. By employing X-ray powder diffraction analyses of oven-dehydrated samples, it was observed that CALID underwent a polymorphic change upon complete drying (<100 ppm water) at <15% RH. However, CALID is stable as a dehydrated material and converts back to the original dihydrate form upon water re-adsorption at >20% relative humidity. The process for manufacturing SUL includes the drying of CALID and OXOS toluene suspensions by azeotropic distillation under reduced pressure to prepare mixtures containing less than 100 ppm of water. The dry suspensions are then combined and a solvent exchange to dimethylacetamide is conducted (Scheme 13). The resultant solution is heated to 120° C. and agitated for up to 20 hours. During this time, the sulfinate esters, generated within the first hour at 120° C., rearrange to form SUL. The typical levels of the ALC impurity formed under these conditions are 3 LC area %. SUL is isolated in 82% yield and >99.5 LC area % after an aqueous work-up and crystallization from acetonitrile and water (up to 23.3 kg scale).

Scheme 12. Preparation of Calcium Isopropylsulfinate Dihydrate (CALID)

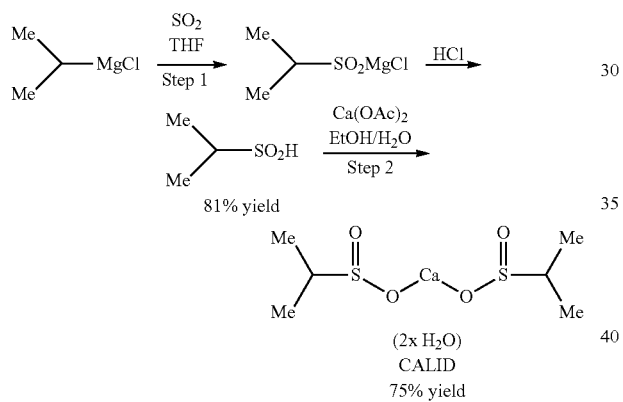

Scheme 13. Preparation of SUL using CALID

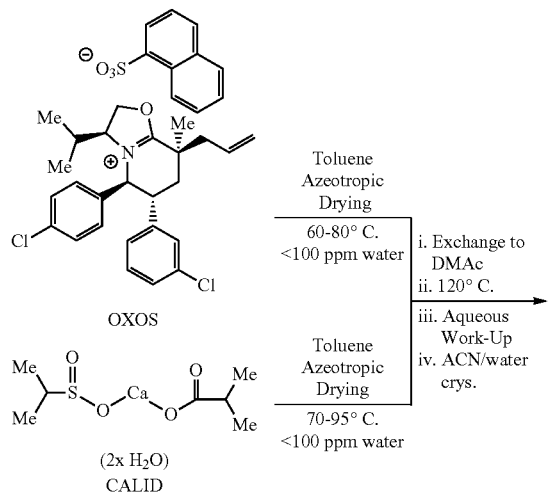

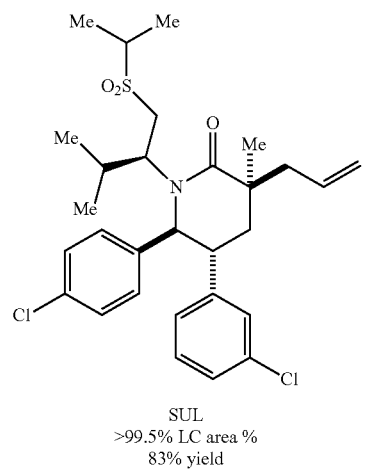

SUL
>99.5% LC area %
83% yield

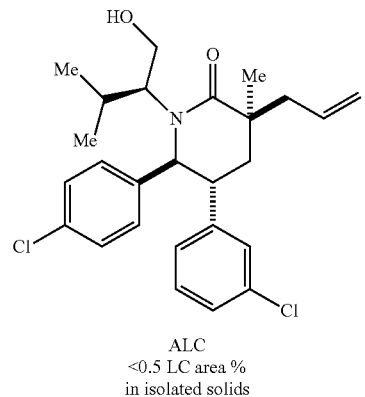

ALC
<0.5 LC area %
in isolated solids

Isopropyl magnesium chloride was prepared in situ as a dry reagent and employed directly in the manufacture of SUL, offering an alternative strategy for the manufacture of SUL from OXOS. As shown in Scheme 14, a tetrahydrofuran solution of isopropyl magnesium chloride was treated with sulfur dioxide to prepare isopropylsulfinate magnesium chloride. In-situ FTIR (with a peak at 1325 cm$^{-1}$) was used to verify complete consumption of the sulfur dioxide. A phenanthroline test was employed to confirm the absence of alkyl Grignard prior to subsequent processing. Solvent exchange to N-methylpyrrolidinone (NMP) was followed by the addition of OXOS to afford SUL at 120° C. or 180° C. (Scheme 14). Elimination of undesired moisture and/or magnesium chloride hydroxide from the reaction mixture thus prepared is challenging. For instance, when three equivalents of isopropylsulfinate magnesium chloride are employed relative to OXOS, approximately 5 mol % of magnesium chloride hydroxide (relative to OXOS) is present in the starting Grignard solution. NMP (5 volumes) and OXOS incorporate 5-10 mol % of water (relative to OXOS). It is thus difficult to avoid the formation of a minimum of 15 mol % of ALC using this reagent. Interestingly, the levels of ALC observed during the formation of SUL under these conditions exceed the measured amount of water or hydroxide contained in the reaction mixture by a margin that depends on the operating temperature. A second mechanism, in addition to the direct opening of OXOS with water or a hydroxide salt (Scheme 4), must be invoked to account for the formation of ALC. This postulated mechanism involves the reaction of SULFI with isopropylsulfinate magnesium chloride to afford ALC (Scheme 15).

Figure 4:
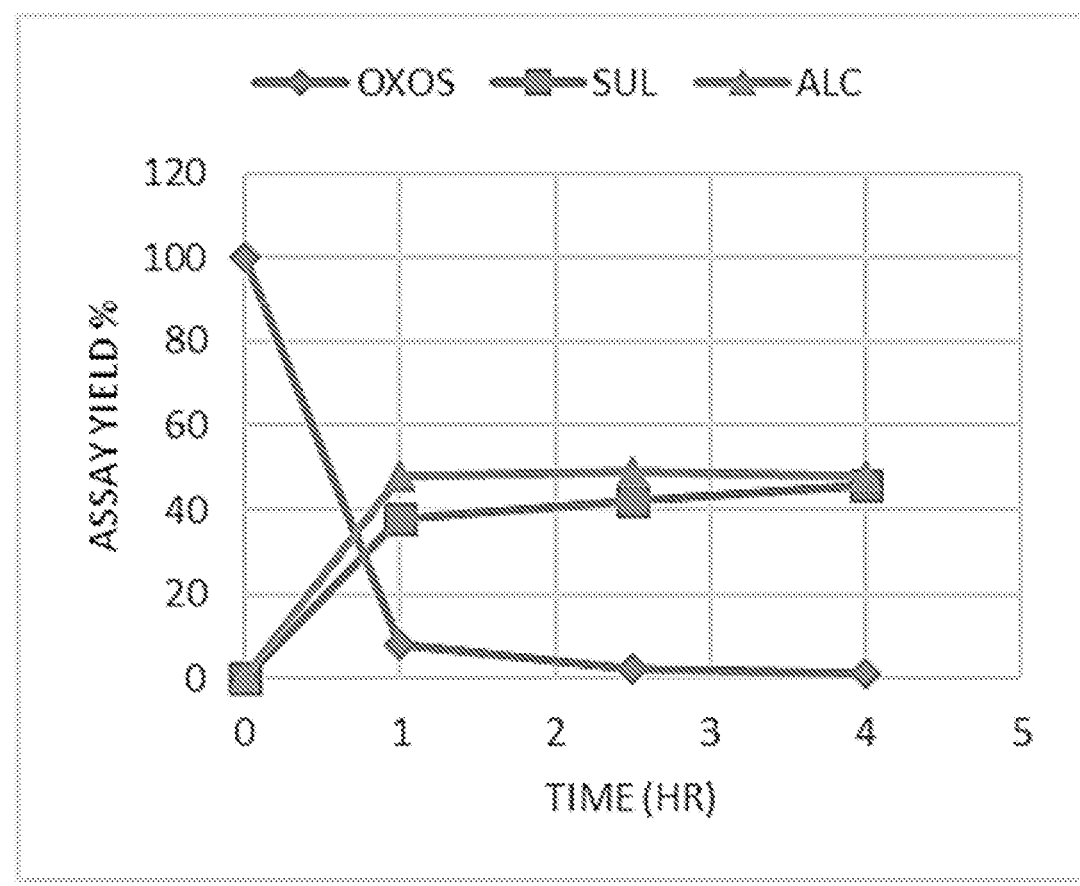
FIG. 4 illustrates the yield of (3S,5R,6S)-3-allyl-5-(3-chlorophenyl)-6-(4-chlorophenyl)-1-((S)-1-(isopropylsulfonyl)-3-methylbutan-2-yl)-3-methylpiperidin-2-one (SUL) over time using isopropylsulfinate magnesium chloride at 120° C. (14 mol % of water (vs (3S,5S,6R,8S)-8-allyl-6-(3-chlorophenyl)-5-(4-chlorophenyl)-3-isopropyl-8-methyl-2,3,5,6,7,8-hexahydrooxazolo[3,2-a]pyridin-4-ium naphthalene-1-sulfonate, hemi toluene solvate (OXOS)) in the reaction mixture).
Figure 5:
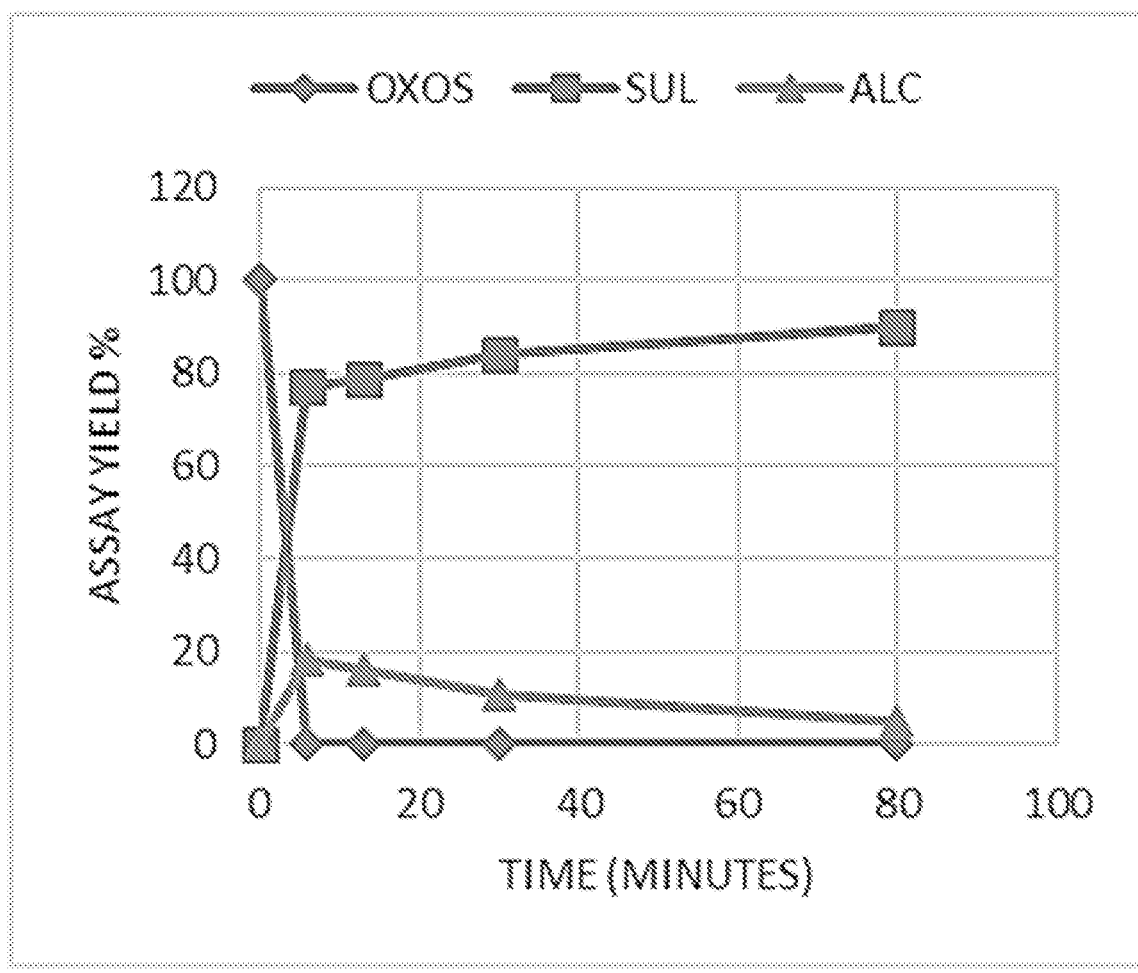
FIG. 5 illustrates the yield of SUL over time using isopropylsulfinate magnesium chloride at 180° C. (11 mol % of water (vs OXOS) in the reaction mixture).

There is an operative mechanism that explains the conversion of ALC to SUL at elevated temperatures (e.g., 180° C.), but it does not occur at a commercially suitable rate at 120° C. (FIG. 4). Treatment of OXOS with isopropylsulfi-nate magnesium chloride (3 equivalents) in NMP (5 volumes) at 180° C. allows the formation of SUL and ALC in 77% and 18% assay yields, respectively, after 6 minutes. After 80 minutes, the assay yields of SUL and ALC are 90% and 5%, respectively (FIG. 5). It is proposed that the magnesium salts act as Lewis acids, facilitating the formation of OXOS from ALC (Scheme 15). Isopropylsulfinate magnesium chloride has poor stability at elevated temperatures and has been observed by $^1$H NMR to experience 85% degradation over 1 hour at 200° C. as a 1 M solution in NMP. Consequently, three equivalents of isopropylsulfinate magnesium chloride were utilized to carry out the transformation.

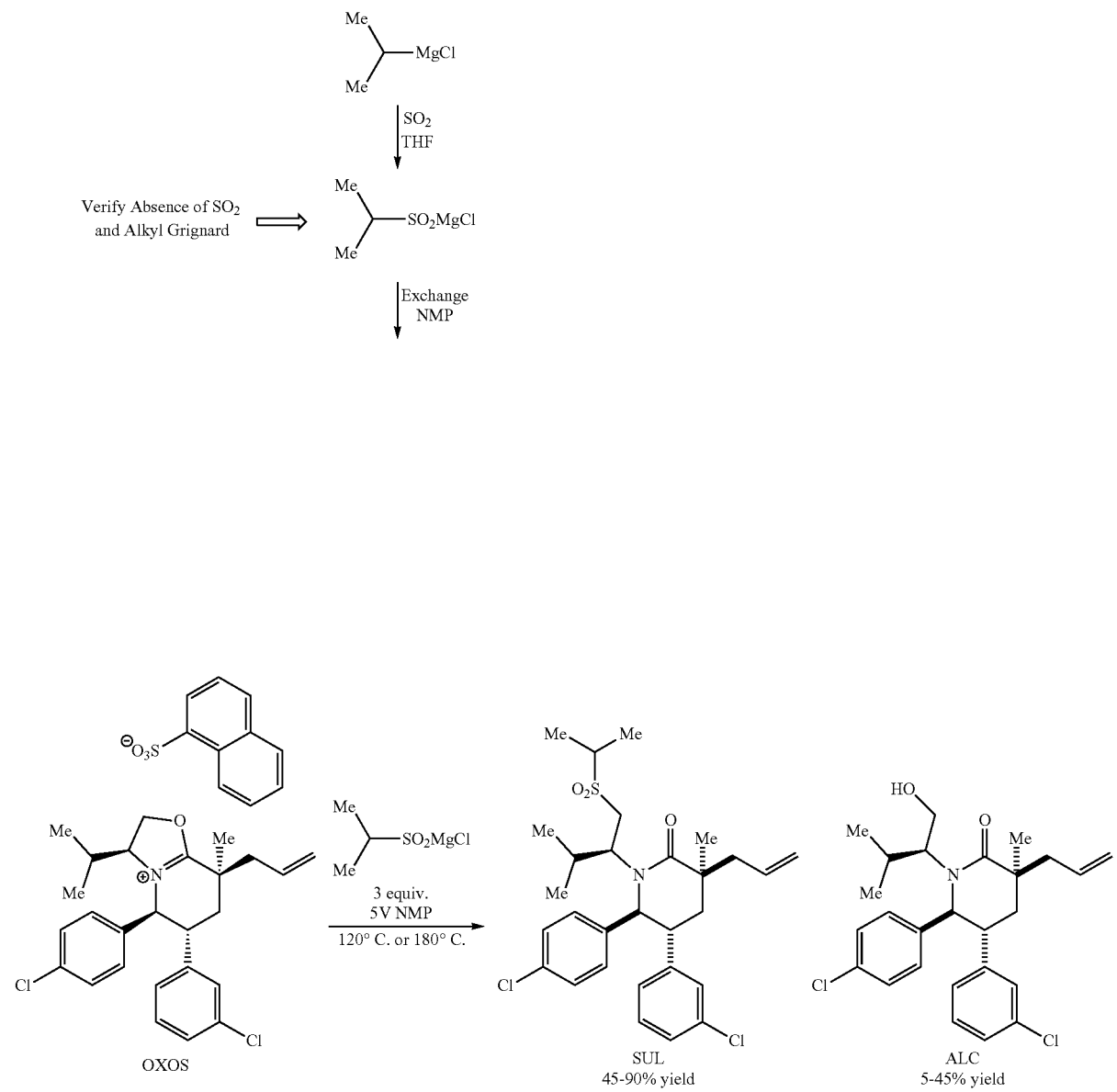

Scheme 15. Possible Mechanisms for Generation of ALC and Conversion of ALC to SUL

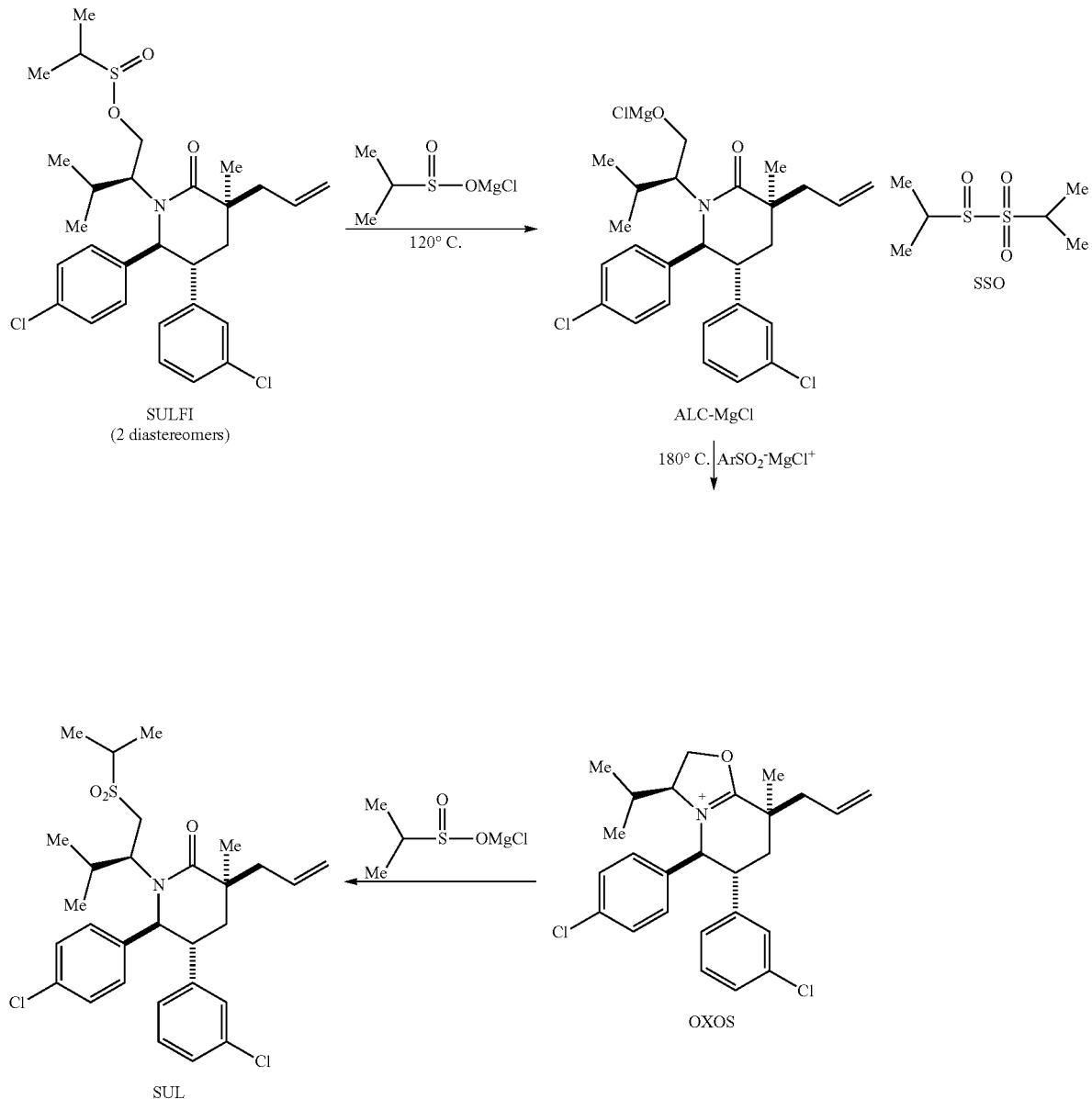

Figure 6:
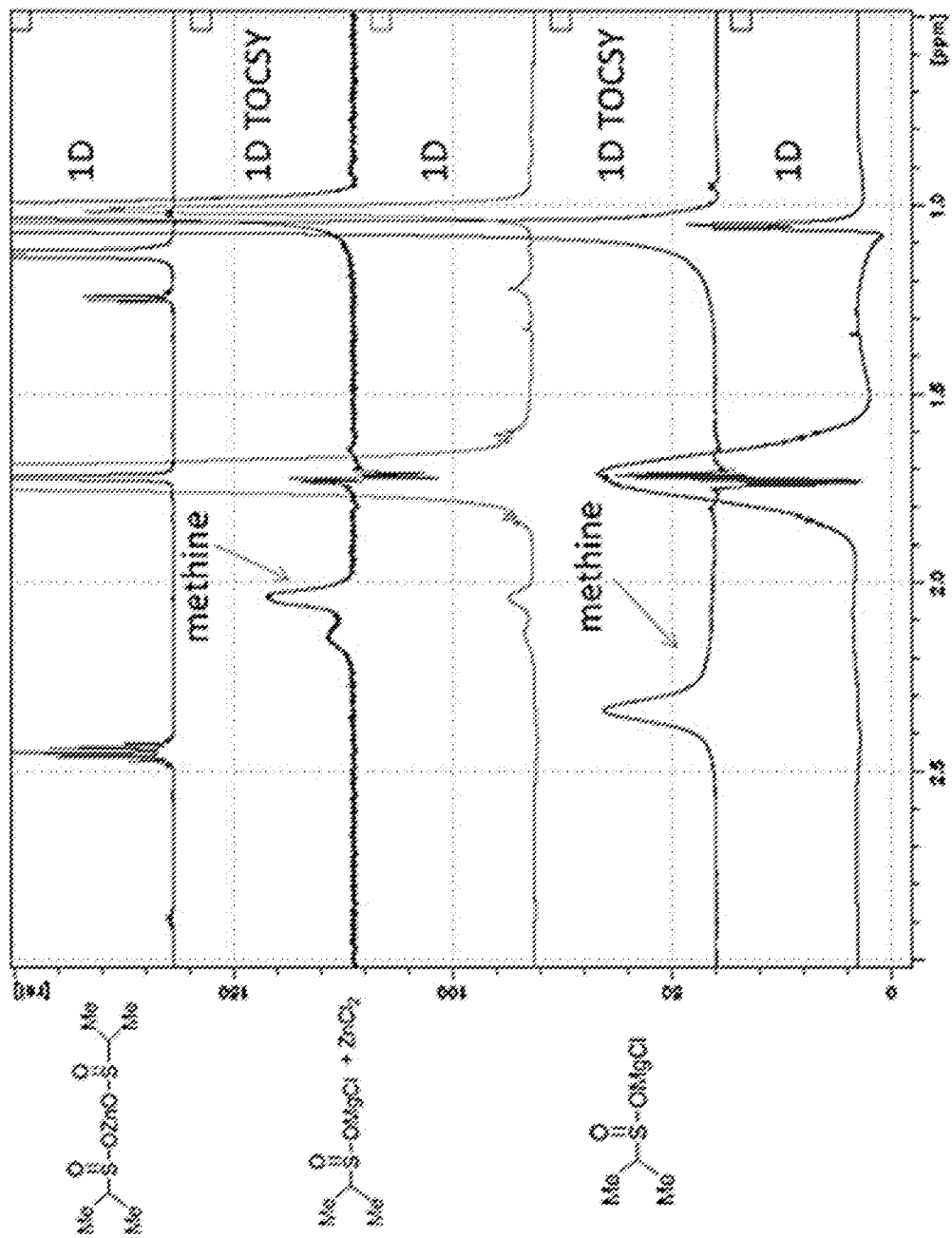
FIG. 6 illustrates $^1$H NMR analyses of different isopropyl sulfinate species in THF-$d_8$.
Figure 7:
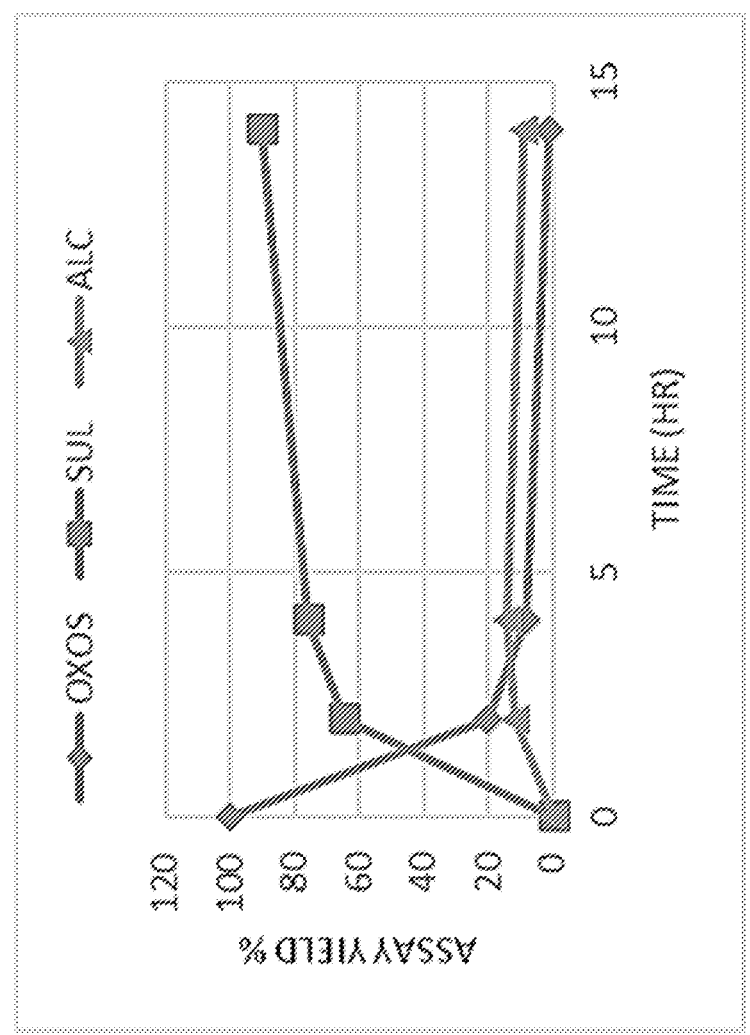
FIG. 7 illustrates the yield of SUL over time using Mg sulfinate-$ZnCl_2$ at 120° C. (17 mol % of water (vs OXOS) in the reaction mixture).
Figure 8:
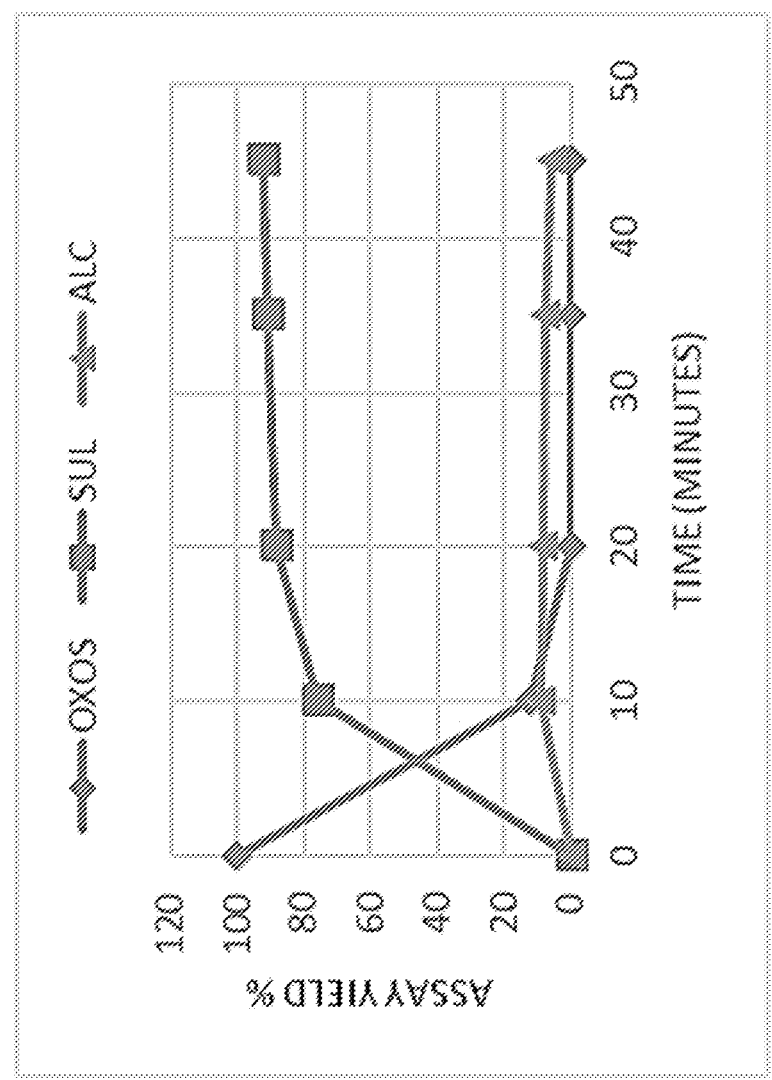
FIG. 8 illustrates the yield of SUL over time using Mg sulfinate-$ZnCl_2$ at 180° C. (17 mol % of water (vs OXOS) in the reaction mixture).

Use of alternative isopropylsulfinate salts to modify the reactivity and to increase the stability of isopropylsulfinate magnesium chloride was evaluated. Treatment of one equivalent of the in-situ prepared reagent with one equivalent of zinc chloride afforded promising results. A commercially available zinc chloride tetrahydrofuran solution (0.5 M) was added to the solution of isopropylsulfinate magnesium chloride prepared as previously described (Scheme 12). The new species formed was observed to be distinct from isopropylsulfinate magnesium chloride and zinc isopropylsulfinate by $^1$H NMR (FIG. 6) and its structure was postulated to be that of isopropylsulfinate zinc chloride, with magnesium chloride generated as a by-product. A solvent exchange to NMP (5 volumes) was performed and OXOS was added to the reaction mixture (Scheme 16). Using this mixed reagent, the conversion of ALC to SUL was operative at a productive rate at 120° C. Thus, the conversion can be performed at 120° C. while avoiding decomposition of reagents and reaction intermediates (FIG. 7) and very rigorous moisture-free conditions. Moreover, there is no evidence of an alternative mechanism affording ALC without the involvement of water with this mixed magnesium-zinc reagent, all the ALC generated during the process can be accounted for from the incoming reagents or solvent. This is not to say that this mixed salt cannot be used at 180° C. (FIG. 8), but a temperature of 140° C. was selected to carry out the process, allowing a good reaction rate while using limited equivalents (1.5 equivalents) of the magnesium-zinc species and affording a 90% yield of SUL with 7% ALC in 7 hours. The magnesium-zinc mixed species was shown to stable at 150° C. for 16 hrs by $^1$H NMR experiments.

Scheme 15. Preparation of SUL from OXOS using Isopropylsulfinate Magnesium Chloride-Zinc Chloride

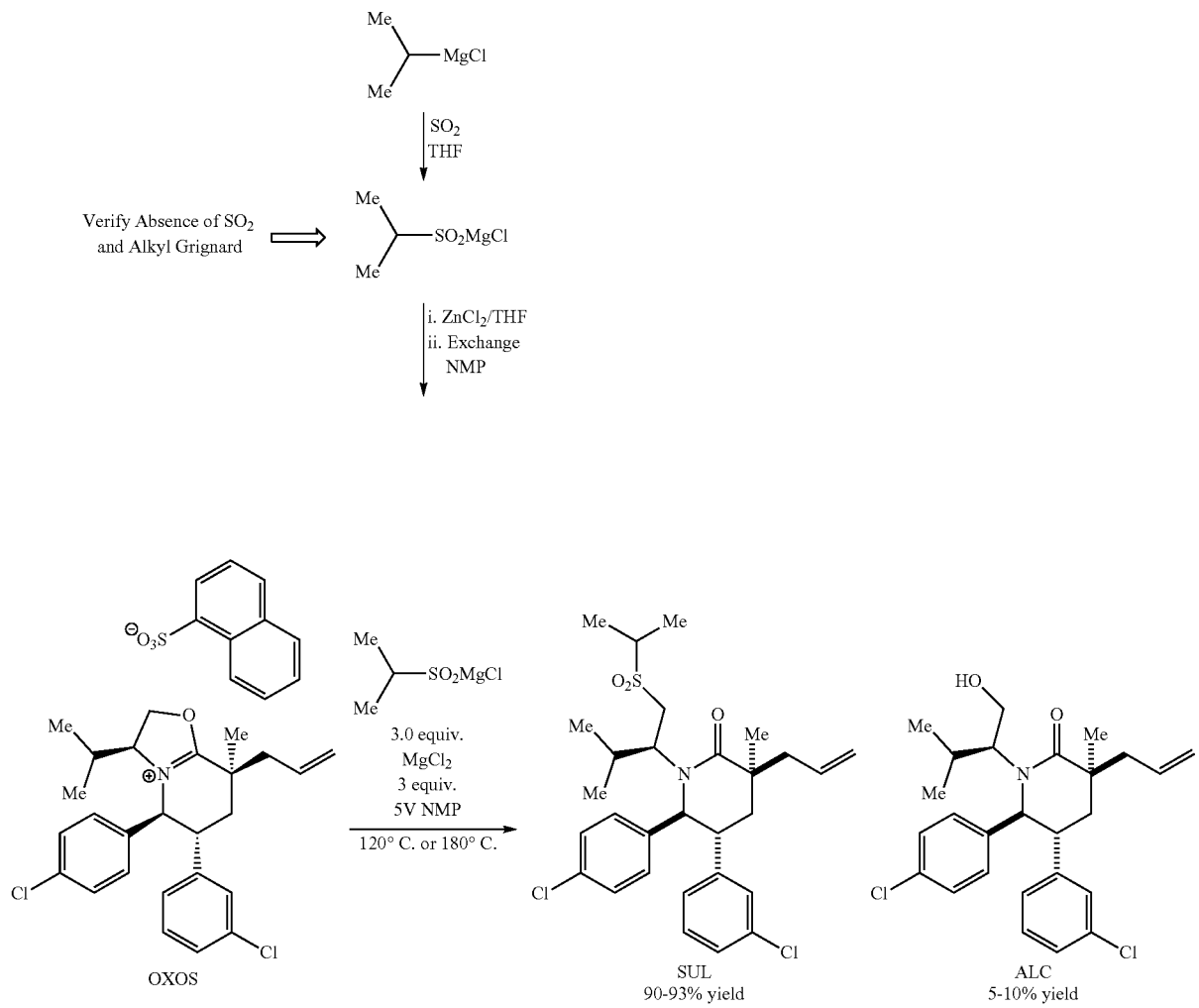

The robustness of this process was evaluated using a 20% excess of sulfur dioxide during the formation of the isopropylsulfinate magnesium chloride and performing the solvent exchange to NMP after 24 hrs of agitation of the mixed salt at 20° C. It was observed that only 40% (by $^1$H NMR) of the sulfinate reagent remained and that 60% of the material had disproportionated to form sulfone SSO (Scheme 15). Using this mixture to convert OXOS to SUL with 1.5 equivalents of the reagent resulted in the formation of SUL in only 62 LC area % and left 33 LC area % of OXOS unreacted, thus demonstrating a lack of robustness for this process since it may prove problematic to control the sulfur dioxide dosing during plant operations. The use of CALID to prepare SUL therefore represents an advantageous aspect of the commercial process to manufacture Compound A.

Example 5: Development of a Commercial Process to Prepare Compound A

Ozonolysis of the alkene group of SUL followed by oxidation of the resulting aldehyde to the corresponding carboxylic acid group of Compound A with sodium chlorite presents a greener alternative to the ruthenium oxide/sodium periodate method used for the initial manufacture of Compound A. In addition, the ozonolysis route would likely eliminate the formation of several undesired dimeric impurities that are difficult to remove via crystallization and thus simplify isolation of the product.

Figure 9:
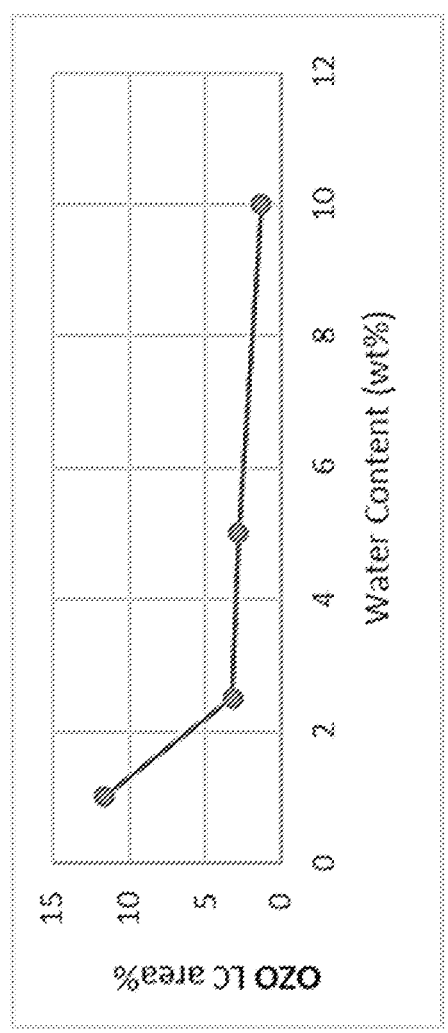
FIG. 9 illustrates the (3R,5R,6S)-3-(1,2,4-trioxolan-3-yl)methyl)-5-(3-chlorophenyl)-6-(4-chlorophenyl)-1-((S)-1-(isopropylsulfonyl)-3-methylbutan-2-yl)-3-methylpiperidin-2-one (OZO) LC area % relative to water wt % in the reaction mixture at 20° C.

In developing safe reaction conditions for the ozonolysis, an aqueous mixture was utilized (Scheme 17). Under these conditions, the high energy ozonide intermediate (OZO) is hydrolyzed, thus avoiding its accumulation and making the process safe. The LC area % of accumulated OZO was measured relative to the volumetric percentage of water used in the acetonitrile/water reaction mixture with the results being reported in FIG. 9. With 10% water, the total energy release for the ozonolysis mixture (20 volumes of solvent) is 92 J/g with a decomposition temperature of 240° C., which does not represent a safety concern. Another parameter requiring control to ensure safety during the ozonolysis is the gas phase concentration of oxygen in the vessel during the reaction. The limiting oxygen concentration (LOC) for combustion of the mixture was measured at 10.75 vol % and the ozonolysis process was conducted at half the LOC (~5 vol % oxygen) to ensure a comfortable margin of safety to avoid possible combustion.

Scheme 17. Preparation of Compound A from SUL using an Ozonolysis-Pinnick Tandem Process

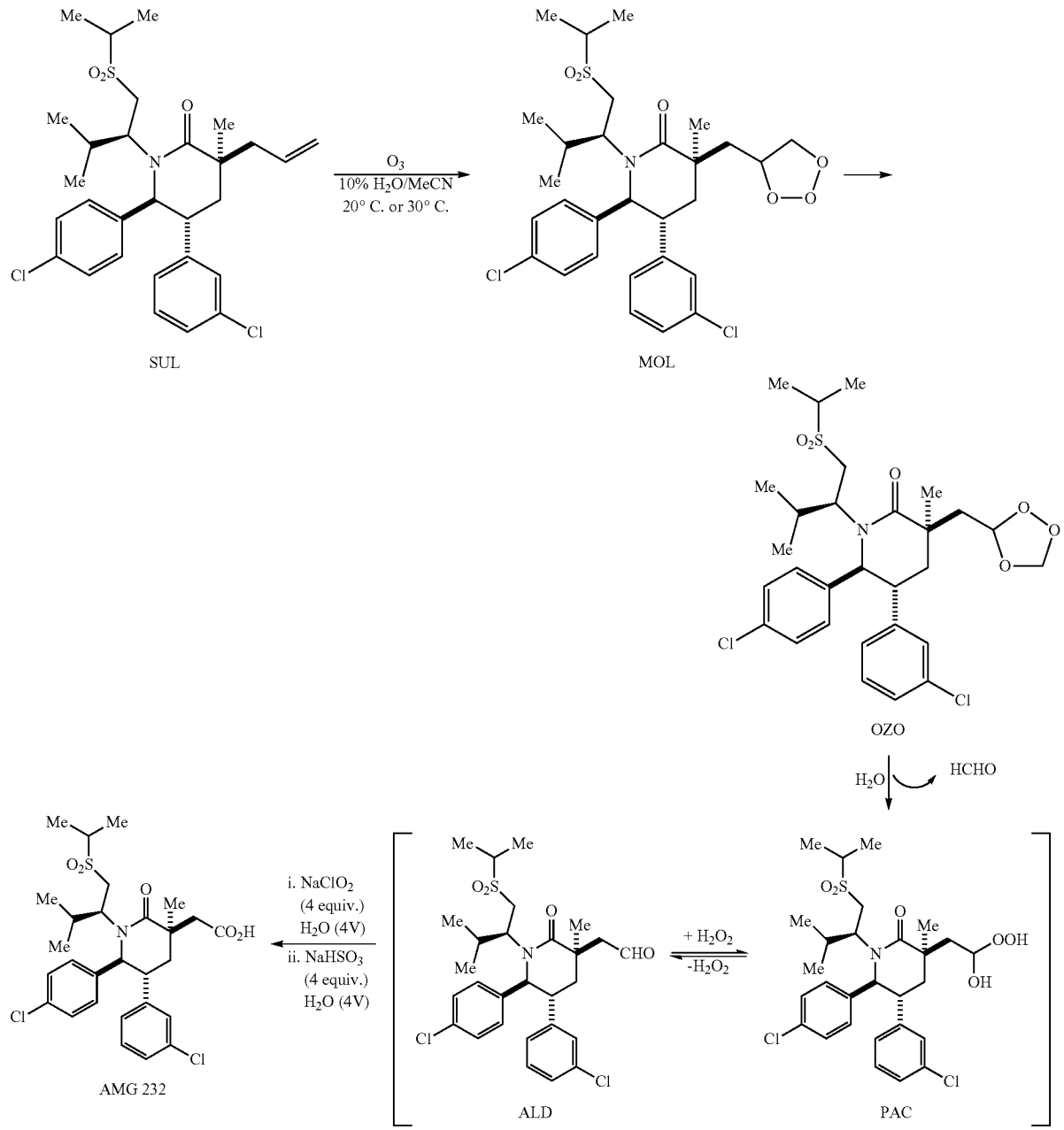

Figure 10:
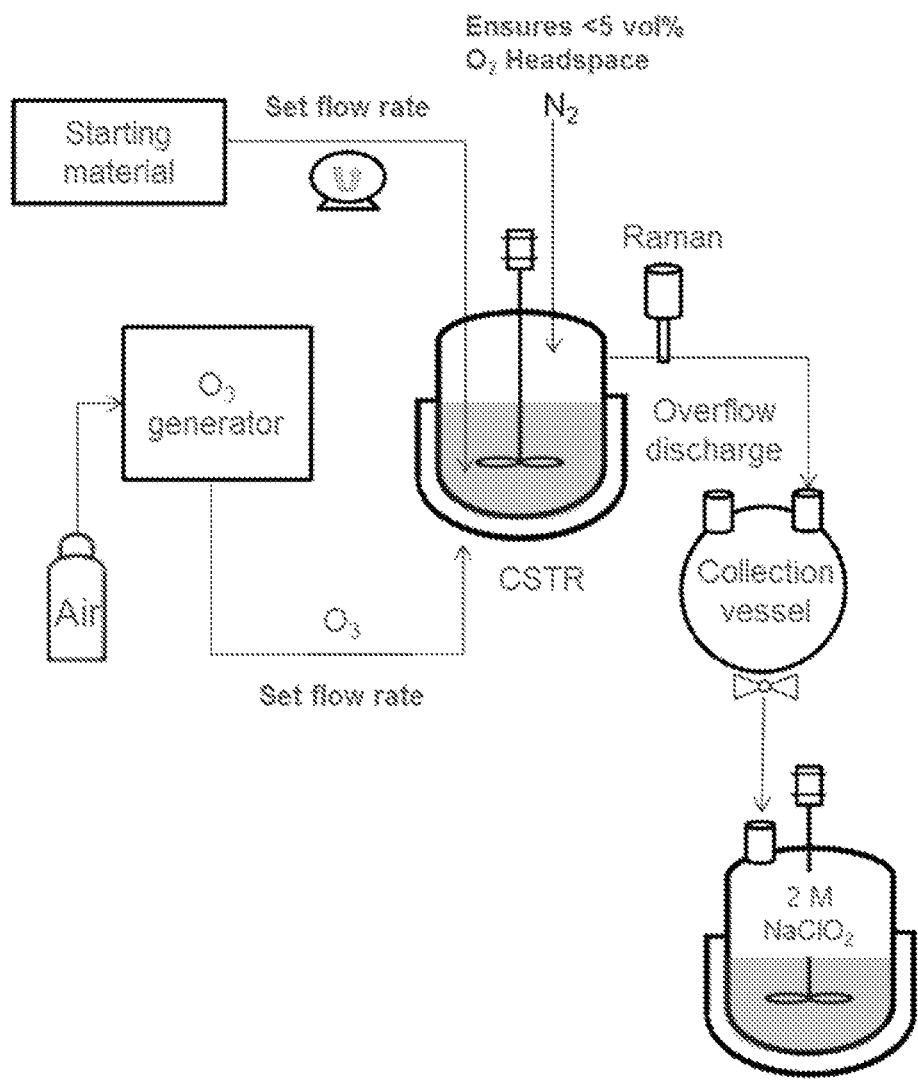
FIG. 10 illustrates a schematic of an apparatus for continuous mode ozonolysis and Pinnick oxidation.
Figure 11:
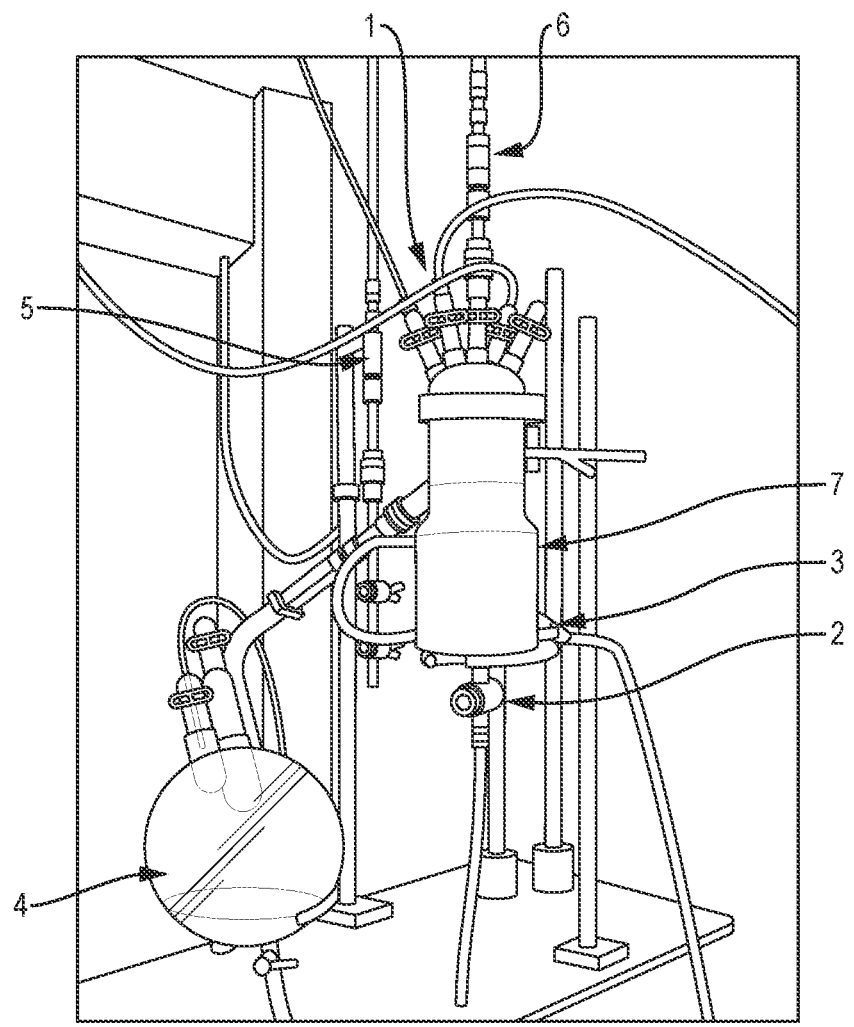
FIG. 11 illustrates a picture of the continuous ozonolysis processing apparatus.

Two different modes of processing have been practiced in the GMP setting for this transformation: (i) a semi-batch ozonolysis using ozone sparging in a batch vessel; and (ii) a continuous stirred-tank reactor process. At the outset, a continuous process appears attractive to alleviate the general safety concerns associated with employing an ozonolysis reaction in a commercial process. A schematic and a picture of the continuous ozonolysis apparatus utilized in one embodiment are presented in FIGS. 10 and 11, respectively. A CFS-3 ozone generator model marketed by Ozonia was utilized to process 4.8 kg of SUL while producing approximately 0.9 mol of ozone per hour. The ozone is generated from an air supply and introduced via a valve located at the bottom of a continuous stirred-tank reactor (CSTR), as shown in FIG. 10. The starting material solution is introduced at a flow rate of 60 mL/minute using a dip tube with an outlet above the glass frit located at the bottom of the vessel (0.9 L capacity). Vigorous agitation of the mixture is important for proper gas dispersion and an example can be seen in FIG. 11. A nitrogen headspace purge having 3× the flow rate of the air flow introduced at bottom is maintained, thus ensuring that less than 5 vol % of oxygen/ozone is present in the gas phase. The reaction mixture is maintained at 20° C. using jacket control. A Raman probe is used at the CSTR outlet to measure the levels of residual SUL.

To minimize the risk in using continuous ozonolysis, accumulated reaction mixture portions were sampled and reaction completion was verified by HPLC. The portions were charged to a 2M aqueous solution of sodium chlorite (4 equivalents) and the resultant mixture agitated for 16 hours at 20° C. Due to the low solubility of the process intermediates (ALD, PAC) in aqueous solutions, addition of the aqueous solution of sodium chlorite to the ozonolysis reaction stream is preferable to the option used to avoid initial precipitation of those intermediates and represents the mode of addition used for the semi-batch ozonolysis process described below.

Figure 12:
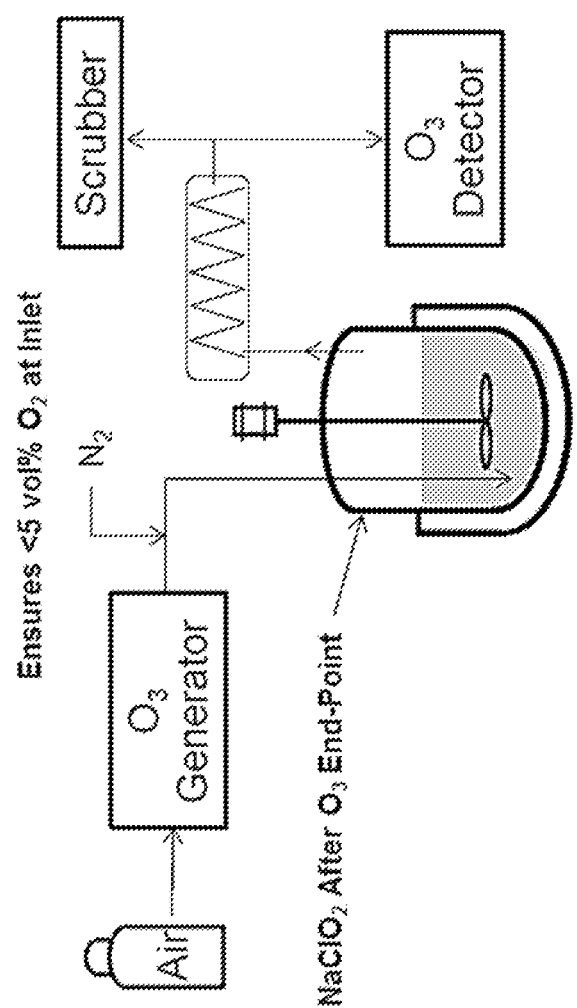
FIG. 12 illustrates a schematic of an apparatus for semi-batch mode ozonolysis and Pinnick oxidation.
Figure 13:
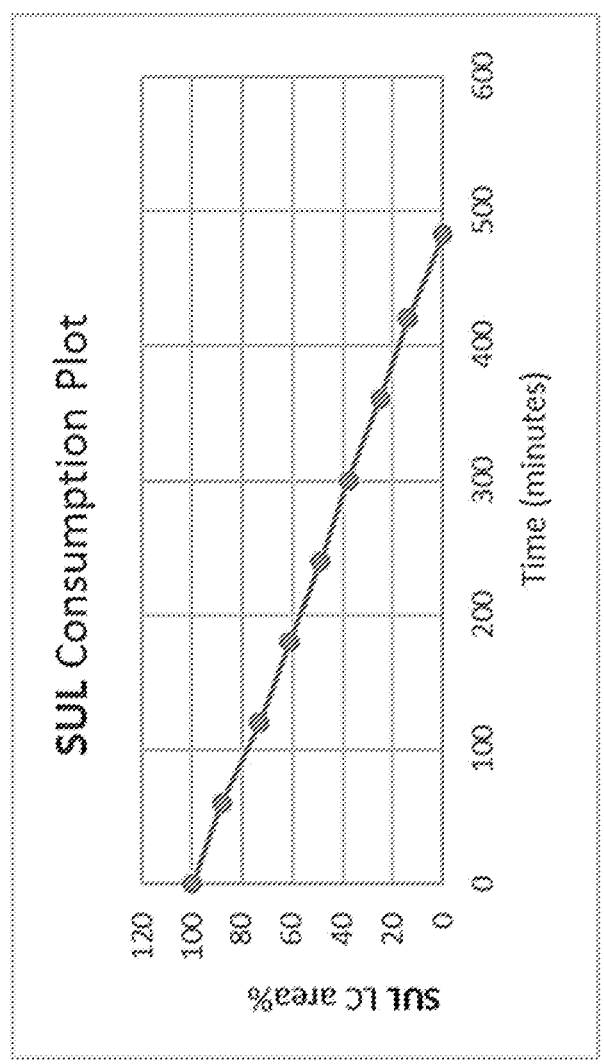
FIG. 13 illustrates the consumption rate of SUL for semi-batch mode ozonolysis.

A semi-batch approach for performing the ozonolysis of SUL has the advantages of processing with an excess of the alkene starting material for most of the transformation and employing a simpler manufacturing footprint. A maximum of 0.4 LC area % of impurity DHCA was observed to be formed using this process mode but a dependable approach is required to monitor reaction completion and safe processing conditions. As described above, safe processing conditions for this reaction manifold are provided by employing an aqueous medium and by maintaining the oxygen concentration below 5 vol %. The air/ozone gas stream is diluted with nitrogen downstream of the ozone generator but upstream of the introduction of the reacting gas through a dip tube in the reaction vessel, as seen in FIG. 12. A gas flow of nitrogen was used four times compared to the air flow, ensuring that gas entering the vessel contains no more than 5 vol % of oxygen/ozone. A headspace ozone detector can be utilized to monitor reaction completion for ozonolysis by measuring an increase in outlet gas concentration. However, this technique was found to be difficult to implement considering that measured changes in the outlet ozone concentration can be subtle. On the other hand, starting material consumption has been found to be linear for this transformation (FIG. 13), thus enabling HPLC analysis of a few samples during the transformation coupled with the knowledge of the ozone generator output to accurately predict the time for reaction completion. A CFS-14 ozone generator model marketed by Ozonia, allowing a maximum output of approximately 540 g of ozone/hour was utilized to process a 23 kg batch of SUL. However, a stable ozone output is easier to maintain with the instrument at less than maximum capacity, and thus an output of 285 g of ozone/hour was utilized for manufacturing and achieved 6080 W power (80% of capacity) and 3.1 SCFM (30% of maximum air flow). The concentration of ozone in the generator output gas was approximately 4.3 wt % using these settings and this gas stream was mixed with nitrogen (12.5 SCFM) prior to entering the processing vessel. The predicted time to reaction completion using the ozone gas output (7.4 hours) was exceeded by 10% (8.2 hours actual). Ozone is known to react with water to generate hydroxy radical and a portion of the ozone is consumed in this manner, which explains the excess ozone that must be utilized.

Figure 14:
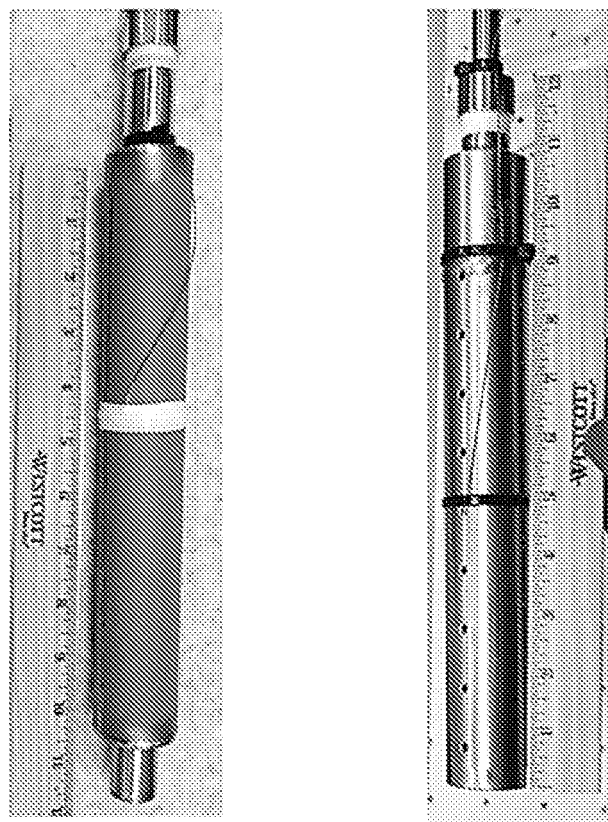
FIG. 14 illustrates sparger evolution for ozonolysis manufacturing development.

For this semi-batch processing, ozone is introduced near the bottom of the reaction vessel via a dip tube. The first device evaluated to deliver gas to the reaction system was a standard ozone sparging unit with 100 μm pore size and a 0.32 square feet total surface. Upon using this sparger to deliver 15.6 SCFM of combined gas flow (air, ozone, and nitrogen), a pressure drop occurred causing cooling of the sparger surface. This decrease in temperature was accompanied by crystallization of the starting material SUL and product ALD, followed by obstruction of the sparger pores by the crystallized material. The solubility of SUL and ALD at 10° C. in acetonitrile/water (9/1 volume ratio) is 25 mg/mL and 21 mg/mL, respectively, and thus only about 50% of either material can be solubilized at that temperature in 20 volumes of the solvent mixture used. Once the sparger is obstructed by starting material or product crystals, the available surface for gas transfer decreases, and the situation is exacerbated, requiring interruption of the process and repair of the sparger. A different ozone sparger was engineering to address this problem. The alternative sparger incorporated ⅛-inch diameter holes pierced in a C22 Hastelloy tube (37 holes). Both spargers are shown in FIG. 14. The impact of using either spargers on reaction mixture and sparger surface temperatures at typical gas flow (15 SFCM) was measured and the results are shown in Table 3. As detailed in the table, there was a significant difference (30° C. vs 11° C. for example) between the sparger surface and the reaction mixture temperatures for the 100 μm pore sparger, causing the problems detailed above. The alternative sparger alleviates these concerns. To avoid any precipitation of SUL and ALD during the ozonolysis process, the transformation was conducted at 30° C.

TABLE 3

Sparger Surface Temperature Control using Different Spargers

| Gas Flow (SFCM) | Sparger pore-size | Reaction mixture temp (° C.) | Sparger surface temp (° C.) |
|---|---|---|---|
| 15 | 100 | 12 | 2 |
| 15 | 100 | 30 | 11 |
| 15 | ⅛-inch | 13 | 11 |
| 15 | ⅛-inch | 25 | 22 |

After completion of the ozonolysis process, addition of the 2M aqueous sodium chlorite solution was observed to enable the formation of Compound A. The mixture is treated with 2M aqueous sodium bisulfite to eliminate all oxidants for further processing. Phase separation was followed by addition of isopropyl acetate, and two washings of the organic layer with 2M aqueous sodium phosphate (pH 6) were conducted. Finally, the organic phase was washed with 1.1 M aqueous sodium chloride to prepare a solution of Compound A in >95% assay yield and >98 LC area % purity.

Example 6: Isolation of Compound a as a DABCO Salt

Considering that a drug substance control point enabling a robust removal of impurities was not available for the free-acid, several salts of Compound A were prepared and tested to discover an effective candidate to allow for the facile removal of impurities. Over thirty organic salts and five inorganic salts of Compound A were evaluated for that purpose, facilitating the identification of a hemi-DABCO salt and a hemi-calcium salt as promising contenders. However, the hemi-calcium salt displayed only a moderate removal of the starting material SUL or the impurity HAC whereas use of the hemi-DABCO isopropyl acetate salt (232-DAB) allowed for the efficient removal of both species (IPAC=isopropyl acetate).

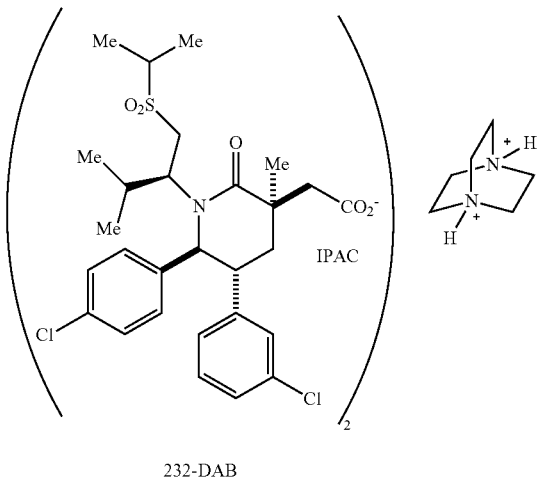

232-DAB

Five (5) LC area % of SUL and 1 LC area % of HAC could be completely removed during the isolation of the latter salt, levels which are significantly higher than observed in a typical ozonolysis-Pinnick oxidation reaction mixture. 232-DAB has been observed to be a stable crystalline mono-solvate (isopropyl acetate) hemi-DABCO salt by TGA and $^1$H NMR. A single polymorph of the material has been identified. The polymorphic form and the isopropyl acetate level of the material was unchanged by a dynamic vapor sorption experiment conducted from 0 to 90% relative humidity. In addition, a robust crystallization protocol based on temperature and the use of an anti-solvent could be designed for the hemi-DABCO isopropyl acetate salt using isopropyl acetate and heptane.

Figure 15:
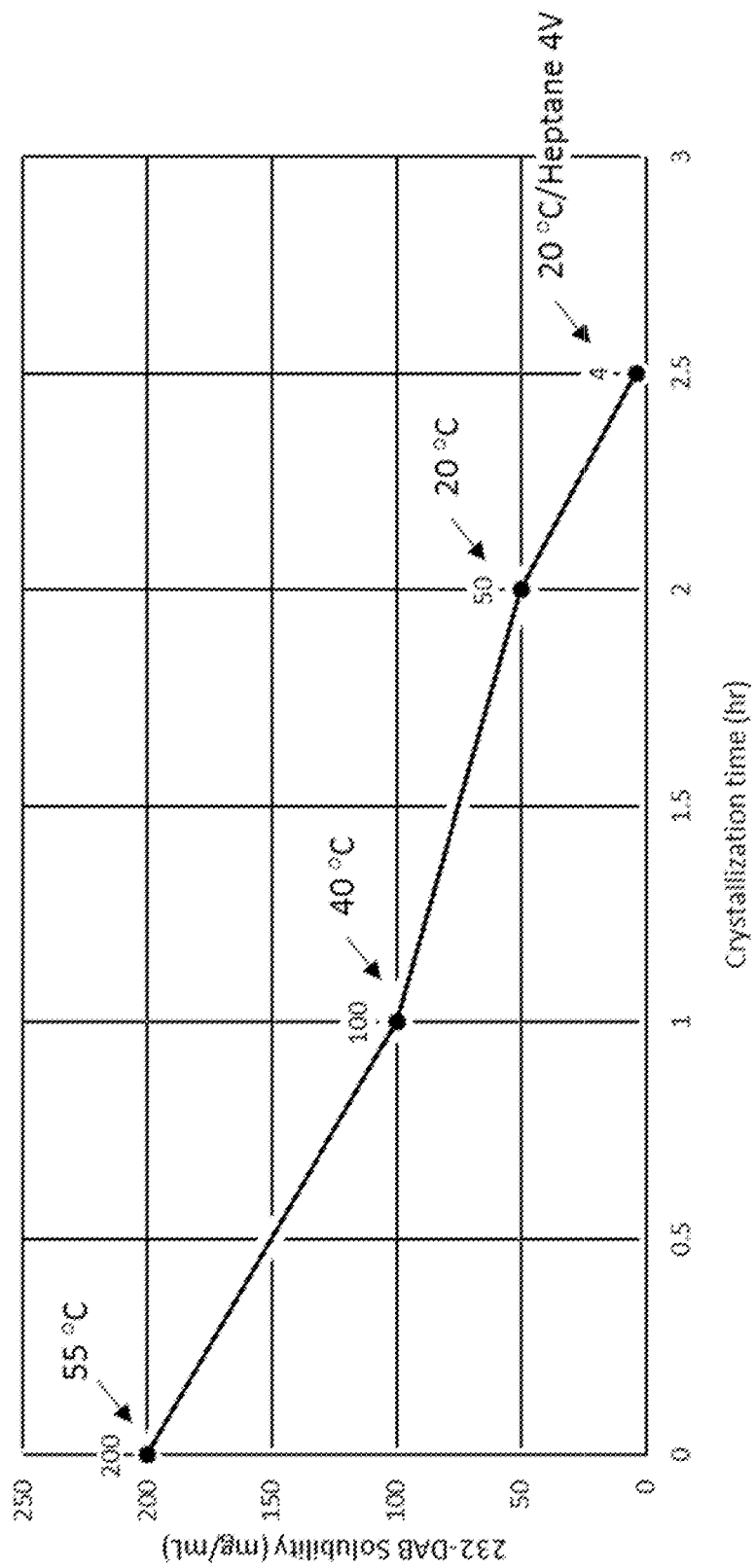
FIG. 15 illustrates the solubility of 232-DAB during the crystallization process.

A solubility curve displaying values at different time intervals in the crystallization process is shown in FIG. 15. Upon the addition of DABCO (0.5 equivalents) to a solution of Compound A in four volumes of isopropyl acetate at 55° C., the solution is seeded with 232-DAB, allowing supersaturation release and crystallization of approximately 20% of the material. Cooling to 20° C. in 2 hours prompts another 60% of the material to crystallize. Four volumes of heptane are subsequently added to lower the supernatant concentration to approximately 5 mg/mL in preparation for batch filtration. Using this crystallization procedure allows for the isolation of 232-DAB in 83% yield and >99.9 LC area % purity (up to 23.2 kg scale).

Example 7: Isolation of Compound A

An aqueous crystallization protocol was desired to isolate Compound A via an orthogonal purification process considering that the crystallization 232-DAB was performed in organic solvents. Alcohol-water solvent mixtures could not be utilized for the crystallization considering the general instability of Compound A in alcohol solvents above 20-30° C. due to Fischer esterification and the inability to remove the ester impurities via crystallization. Other aqueous mixtures with water-miscible solvents showed steep solubility curves that were not conducive to crystallization design. In contrast, acetic acid and water was suitable to crystallize the material without the drawbacks detailed above and with good growth characteristics. A robust temperature and anti-solvent based crystallization was designed using this solvent mixture and operated after a salt break in an aqueous hydrochloric acid (2 equivalents)/isopropyl acetate mixture, two subsequent washings of the organic layer with 2M aqueous sodium phosphate (pH 6), a washing with 1.1 M aqueous sodium chloride, and a solvent exchange from isopropyl acetate to acetic acid.

Figure 16:
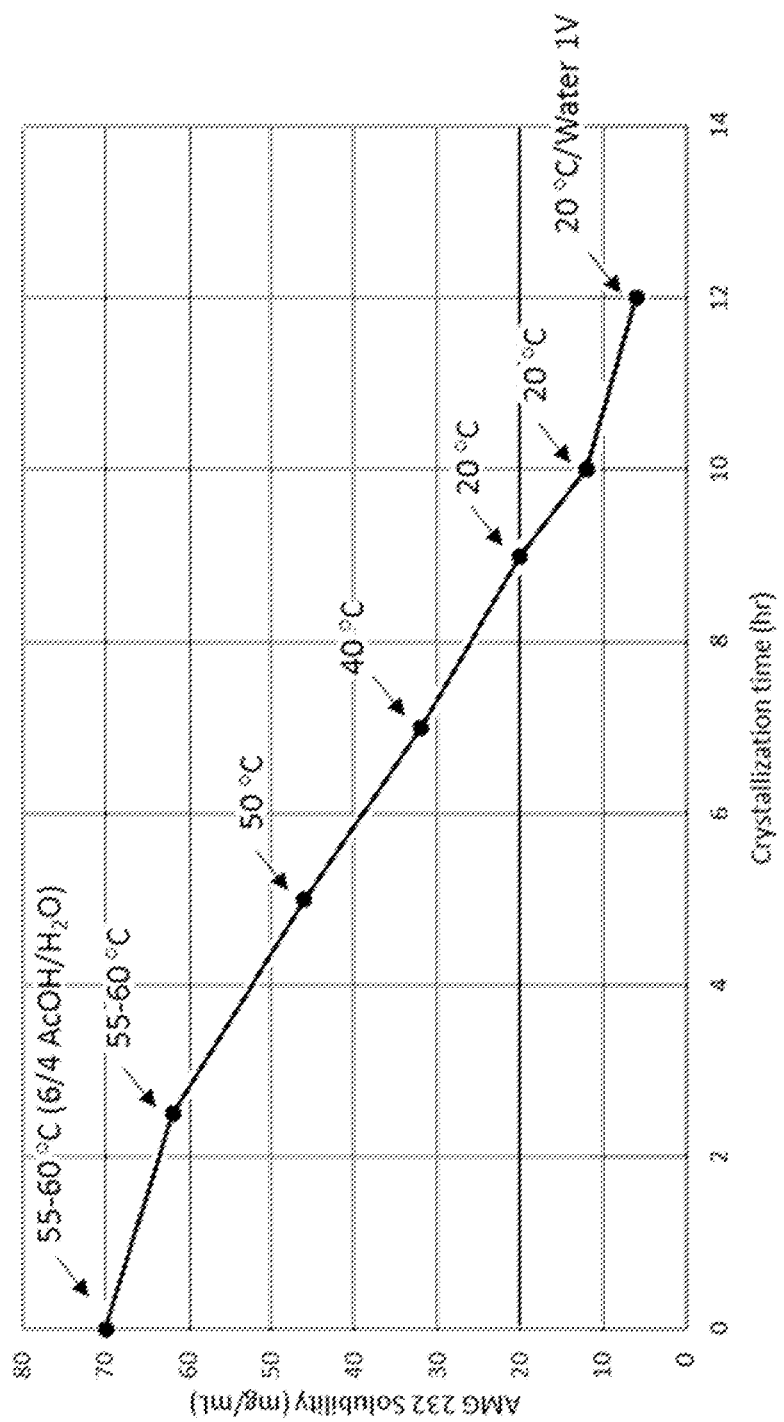
FIG. 16 illustrates the solubility of Compound A during the crystallization process.

A curve showing solubility values at different time points in the crystallization process is represented in FIG. 16. An acetic acid solution (6.6 volumes of acetic acid) of Compound A is warmed to 55-60° C. and 4.4 volumes of water are added. The solution is seeded with Compound A, allowing supersaturation release and crystallization of approximately 30% of Compound A. The crystallization is cooled to 20° C. in 10 hours, resulting in the crystallization of another 55% of the material. One volume of water is subsequently added to lower the supernatant concentration to approximately 5 mg/mL in preparation for a rapid batch filtration. Three water washings (3×10 volumes) were conducted to minimize the presence of residual acetic acid in the isolated material. Compound A (up to 18.0 kg) was isolated using this protocol in >92% isolated yield (100 wt %) and >99.9 LC area % purity with <200 ppm of residual water and <200 ppm of residual acetic acid.

The material was milled using a Pallman Universal Mill (wing beater, up to 16 kg scale) and the results are summarized in Table 4. The target d50 for Compound A was set at <35 μm based on oral absorption modeling (GastroPlus v 9.0) for the range of doses evaluated (60 to 480 mg) to provide complete absorption at fasted gastric pH of 1.3.

TABLE 4

Compound A Particle Size Distribution Pre and Post Dry-Milling

| Material | d10 (μm) | d50 (μm) | d90 (μm) |
|---|---|---|---|
| Compound A unmilled | 14.6 | 42.5 | 102 |
| Compound A milled | 3.2 | 19.1 | 43.7 |

A robust and efficient process suitable for the commercial manufacture of a drug substance (Compound A) in high purity has been developed. Significant aspects of the process include: (i) the use of a bench-stable Vilsmeier reagent, methoxymethylene-N,N-dimethyliminium methyl sulfate, for selective in situ activation of a primary alcohol intermediate; (ii) the isolation of intermediate DHO in crystalline form, which enhances the capacity of the process capacity to remove impurities; (iii) the use of a new and stable isopropyl calcium sulfinate reagent in crystalline form to ensure the robust preparation of a sulfone intermediate; (iv) the development of a safe ozonolysis protocol conducted in an aqueous solvent mixture that is suitable for either a batch or continuous manufacturing mode; (v) enhanced purity control of Compound A by formation of a salt of Compound A that allows for effective removal of impurities. The new process was demonstrated to provide 18 kg of pure Compound A (99.9 LC area %) in 49.8% overall yield from DLAC, representing a significant improvement over the described FIE process which only resulted in a 32% overall yield.

What is claimed is:
1. A process of preparing compound

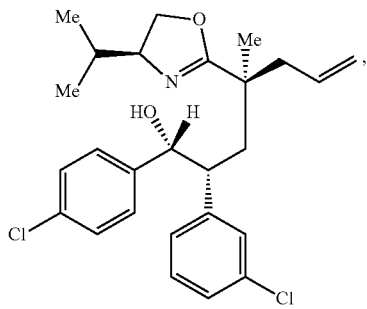 [SMILES: C=CC[C@@](C)(C[C@H](c1cccc(Cl)c1)[C@@H](O)c1ccc(Cl)cc1)C1=N[C@@H](C(C)C)CO1]

the process comprising reacting

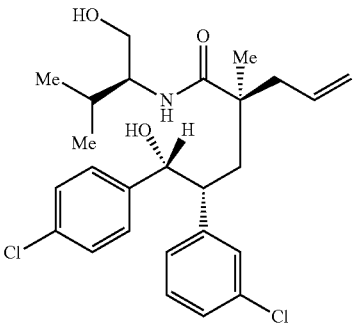 [SMILES: C=CC[C@@](C)(C[C@H](c1cccc(Cl)c1)[C@@H](O)c1ccc(Cl)cc1)C(=O)N[C@H](CO)C(C)C]

with methoxymethylene-N,N-dimethyliminium methyl sulfate.

2. The process of claim 1, wherein the reaction is carried out in the presence of a base.
3. The process of claim 2, wherein the base is KOAc, NaOAc, LiOAc, or $K_2CO_3$.
4. The process of claim 2, wherein the base is NaOAc.
5. The process of claim 1, wherein the reaction is carried out in a solvent.
6. The process of claim 5, wherein the solvent is toluene.

* * * * *